United States Patent
Arora et al.

(10) Patent No.: US 11,723,966 B2
(45) Date of Patent: Aug. 15, 2023

(54) METHODS OF BOOSTING IMMUNE RESPONSES

(71) Applicant: GLAXOSMITHKLINE BIOLOGICALS SA, Rixensart (BE)

(72) Inventors: Ashwani Kumar Arora, Siena (IT); Vincent Weynants, Wavre (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 228 days.

(21) Appl. No.: 16/638,595

(22) PCT Filed: Aug. 13, 2018

(86) PCT No.: PCT/EP2018/071860
§ 371 (c)(1),
(2) Date: Feb. 12, 2020

(87) PCT Pub. No.: WO2019/034575
PCT Pub. Date: Feb. 21, 2019

(65) Prior Publication Data
US 2020/0197504 A1    Jun. 25, 2020

Related U.S. Application Data

(60) Provisional application No. 62/545,010, filed on Aug. 14, 2017, provisional application No. 62/633,263, filed on Feb. 21, 2018.

(51) Int. Cl.
| | | |
|---|---|---|
| *A61K 39/00* | (2006.01) | |
| *A61K 39/102* | (2006.01) | |
| *A61P 31/04* | (2006.01) | |
| *A61K 39/104* | (2006.01) | |

(52) U.S. Cl.
CPC ........ *A61K 39/102* (2013.01); *A61K 39/1045* (2013.01); *A61P 31/04* (2018.01); *A61K 2039/545* (2013.01); *A61K 2039/55555* (2013.01)

(58) Field of Classification Search
None
See application file for complete search history.

(56) References Cited

U.S. PATENT DOCUMENTS

2007/0071774 A1 * 3/2007 Forsgren ............ C07K 16/1242
435/488

FOREIGN PATENT DOCUMENTS

| JP | 2017-507181 A | 3/2017 | |
|---|---|---|---|
| WO | 98/28333 A2 | 7/1998 | |
| WO | 2007/018463 A2 | 2/2007 | |
| WO | 2007/084053 A1 | 7/2007 | |
| WO | 2012/139225 A1 | 10/2012 | |
| WO | 2015/125118 A1 | 8/2015 | |
| WO | WO-2015125118 A1 * | 8/2015 | ............. A61K 39/00 |

OTHER PUBLICATIONS

Silfverdal et al. The Pediatric Infectious Disease Journal , vol. 28, Issue 10, pp. 276-282, Oct. 2009. (Year: 2009).*
Leroux_Roels Geert et al. Vaccine vol. 34, No. 27, pp. 3156-3163, Apr. 29, 2016. (Year: 2016).*
Leroux-Roels Geert et al. Vaccine vol. 34, No. 27, pp. 3156-3163, Apr. 2016 (Year: 2016).*
Silverdal , infectious disease journal vol. 28 , 2009 (Year: 2009).*
Leroux-Roels Geert, et al., "Phase I, randomized, observer-blind, placebo-controlled studies to evaluate the safety, reactogenicity and immunogenicity of an investigational non-typableHaemophilus influenzae (NTHi) protein vaccine in adults." Vaccine; 2016; pp. 3156-3163; vol. 34(27).
Immunology-Illustrated, 1990, pp. 99-103 (Japanese counterpart of "Immunology" Second Edition, edited by I. Roitt et al. Mosby, 1989, Section 8) (includes English translation) (15 pages).
Bio pharmaceuticals and Regenerative Medicine, 2016, pp. 86-87 (includes English translation) (6 pages).
Sunagawa, et al., Journal of the Japanese Association for Ii ifectious Diseases, 2011, vol. 85, No. 3, pp. 227-237 (includes English abstract).

* cited by examiner

*Primary Examiner* — Jana A Hines
*Assistant Examiner* — Khatol S Shahnan Shah

(57) ABSTRACT

The present invention relates to immunogenic compositions, such as vaccines, comprising immunogenic polypeptides from *Haemophilus influenzae* and *Moraxella catarrhalis*, for use in methods of boosting an immune response and methods of treatment using same. More particularly, the invention relates to use of such immunogenic compositions in methods of treating or preventing exacerbation of chronic obstructive pulmonary disease.

13 Claims, 18 Drawing Sheets

Specification includes a Sequence Listing.

SEQUENCE LISTING

```
<160> NUMBER OF SEQ ID NOS: 73

<210> SEQ ID NO 1
<211> LENGTH: 360
<212> TYPE: PRT
<213> ORGANISM: Haemophilus influenzae

<400> SEQUENCE: 1

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110
```

```
Leu Lys Glu Ile Gln Ser Leu Glu Met Thr Glu Asn Phe Glu Thr Lys
            115                 120                 125
Asp Gly Lys Gln Ala Gln Val Tyr Pro Asn Arg Phe Pro Leu Trp Lys
        130                 135                 140
Ser His Phe Arg Ile His Thr Phe Glu Asp Glu Ile Glu Phe Ile Gln
145                 150                 155                 160
Gly Leu Glu Lys Ser Thr Gly Lys Lys Val Gly Ile Tyr Pro Glu Ile
                165                 170                 175
Lys Ala Pro Trp Phe His His Gln Asn Gly Lys Asp Ile Ala Ala Glu
            180                 185                 190
Thr Leu Lys Val Leu Lys Lys Tyr Gly Tyr Asp Lys Lys Thr Asp Met
        195                 200                 205
Val Tyr Leu Gln Thr Phe Asp Phe Asn Glu Leu Lys Arg Ile Lys Thr
    210                 215                 220
Glu Leu Leu Pro Gln Met Gly Met Asp Leu Lys Leu Val Gln Leu Ile
225                 230                 235                 240
Ala Tyr Thr Asp Trp Lys Glu Thr Gln Glu Lys Asp Pro Lys Gly Tyr
                245                 250                 255
Trp Val Asn Tyr Asn Tyr Asp Trp Met Phe Lys Pro Gly Ala Met Ala
            260                 265                 270
Glu Val Val Lys Tyr Ala Asp Gly Val Gly Pro Gly Trp Tyr Met Leu
        275                 280                 285
Val Asn Lys Glu Glu Ser Lys Pro Asp Asn Ile Val Tyr Thr Pro Leu
    290                 295                 300
Val Lys Glu Leu Ala Gln Tyr Asn Val Glu Val His Pro Tyr Thr Val
305                 310                 315                 320
Arg Lys Asp Ala Leu Pro Glu Phe Phe Thr Asp Val Asn Gln Met Tyr
                325                 330                 335
Asp Ala Leu Leu Asn Lys Ser Gly Ala Thr Gly Val Phe Thr Asp Phe
            340                 345                 350
Pro Asp Thr Gly Val Glu Phe Leu
        355                 360

<210> SEQ ID NO 2
<211> LENGTH: 348
<212> TYPE: PRT
<213> ORGANISM: Artificial
<220> FEATURE:
<223> OTHER INFORMATION: Protein D fragment with MDP tripeptide from NS1

<400> SEQUENCE: 2

Met Asp Pro Ser Ser His Ser Ser Asn Met Ala Asn Thr Gln Met Lys
1               5                   10                  15
Ser Asp Lys Ile Ile Ile Ala His Arg Gly Ala Ser Gly Tyr Leu Pro
                20                  25                  30
Glu His Thr Leu Glu Ser L

```
Asp Gly Lys Gln Ala Gln Val Tyr Pro Asn Arg Phe Pro Leu Trp Lys
        115                 120                 125

Ser His Phe Arg Ile His Thr Phe Glu Asp Glu Ile Glu Phe Ile Gln
    130                 135                 140

Gly Leu Glu Lys Ser Thr Gly Lys Lys Val Gly Ile Tyr Pro Glu Ile
145                 150                 155                 160

Lys Ala Pro Trp Phe His His Gln Asn Gly Lys Asp Ile Ala Ala Glu
                165                 170                 175

Thr Leu Lys Val Leu Lys Lys Tyr Gly Tyr Asp Lys Lys Thr Asp Met
            180                 185                 190

Val Tyr Leu Gln Thr Phe Asp Phe Asn Glu Leu Lys Arg Ile Lys Thr
        195                 200                 205

Glu Leu Leu Pro Gln Met Gly Met Asp Leu Lys Leu Val Gln Leu Ile
    210                 215                 220

Ala Tyr Thr Asp Trp Lys Glu Thr Gln Glu Lys Asp Pro Lys Gly Tyr
225                 230                 235                 240

Trp Val Asn Tyr Asn Tyr Asp Trp Met Phe Lys Pro Gly Ala Met Ala
                245                 250                 255

Glu Val Val Lys Tyr Ala Asp Gly Val Gly Pro Gly Trp Tyr Met Leu
            260                 265                 270

Val Asn Lys Glu Glu Ser Lys Pro Asp Asn Ile Val Tyr Thr Pro Leu
        275                 280                 285

Val Lys Glu Leu Ala Gln Tyr Asn Val Glu Val His Pro Tyr Thr Val
    290                 295                 300

Arg Lys Asp Ala Leu Pro Glu Phe Phe Thr Asp Val Asn Gln Met Tyr
305                 310                 315                 320

Asp Ala Leu Leu Asn Lys Ser Gly Ala Thr Gly Val Phe Thr Asp Phe
                325                 330                 335

Pro Asp Thr Gly Val Glu Phe Leu Lys Gly Ile Lys
            340                 345

<210> SEQ ID NO 3
<211> LENGTH: 989
<212> TYPE: DNA
<213> ORGANISM: Haemophilus influenzae

<400> SEQUENCE: 3
gcgaataccc aaatgaaatc agacaaaatc attattgctc accgtggtgc tagcggttat      60
ttaccagagc atacgttaga atctaaagca cttgcgtttg cacaaacacgc agattattta   120 gagcaagatt tagcaatgac taaggatggt cgtttagtgg ttattcacga tcactttta    180 gatggcttga ctgatgttgc gaaaaaattc ccacatcgtc accgtaaaga tggtcgttac   240
tatgtcatcg actttacctt aaaagaaatt caaagtttag aaatgactga aactttgaa    300 accaaagacg caaacaagc gcaagtttat cctaatcgtt cccactttg gaaatcacat    360 tttagaattc acacctttga gatgaaatt gagtttatcc aaggcttaga aaaatcgact   420
ggcagaaaag tagggattta ccagaaatc aaagcacctt ggttccacca tcaaaatggc   480
aaagatattg cagctgaaac gctcaaagtg ttaaaaaaat atggctatga taagaaaacc   540
gatatggttt acttacaaac tttcgatttt aatgaattaa aacgtatcaa aacggaatta   600
cttccacaaa tgggaatgga tttaaaatta gttcaattaa ttgcttatac agattggaaa   660
gaaacacaag aaaaagaccc aaagggttat tgggtaaact ataattacga ttggatgttt   720
aaacctggtg caatggcaga agtggttaaa tatgccgatg gtgttggccc aggttggtat   780
```

| | |
|---|---|
| atgttagtta ataaagaaga atccaaacct gataatattg tgtacactcc gttggtaaaa | 840 |
| gaacttgcac aatataatgt ggaagtgcat ccttacaccg tgcgtaaaga tgcactgccc | 900 |
| gagttttca cagacgtaaa tcaaatgtat gatgccttat tgaataaatc aggggcaaca | 960 |
| ggtgtattta ctgatttccc agatactgg | 989 |

<210> SEQ ID NO 4
<211> LENGTH: 989
<212> TYPE: DNA
<213> ORGANISM: Haemophilus influenzae

<400> SEQUENCE: 4

| | |
|---|---|
| gcgaataccc aaatgaaatc agacaaaatc attattgctc accgtggtgc tagcggttat | 60 |
| ttaccagagc atacgttaga atctaaagca cttgcgtttg cacaacacgc agattattta | 120 |
| gagcaagatt tagcaatgac taaggatggt cgtttagtgg ttattcacga tcacttttta | 180 |
| gatggcttga ctgatgttgc gaaaaaattc ccacatcgtc accgtaaaga tggtcgttac | 240 |
| tatgtcatcg actttacctt aaaagaaatt caaagtttag aaatgactga aactttgaa | 300 |
| accaaagacg gcaaacaagc gcaagtttat cctaatcgtt tcccactttg gaaatcacat | 360 |
| tttagaattc acacctttga agatgaaatt gagtttatcc aaggcttaga aaaatcgact | 420 |
| ggcagaaaag tagggattta ccagaaaatc aaagcaccct tggttccacca tcaaaatggc | 480 |
| aaagatattg cagctgaaac gctcaaagtg ttaaaaaaat atggctatga taagaaaacc | 540 |
| gatatggttt acttacaaac tttcgatttt aatgaattaa aacgtatcaa aacggaatta | 600 |
| cttccacaaa tgggaatgga tttaaaatta gttcaattaa ttgcttatac agattggaaa | 660 |
| gaaacacaag aaaagaccc aaaggggttat tgggtaaact ataattacga ttggatgttt | 720 |
| aaacctggtg caatggcaga agtggttaaa tatgccgatg gtgttggccc aggttggtat | 780 |
| atgttagtta ataaagaaga atccaaacct gataatattg tgtacactcc gttggtaaaa | 840 |
| gaacttgcac aatataatgt ggaagtgcat ccttacaccg tgcgtaaaga tgcactgccc | 900 |
| gagttttca cagacgtaaa tcaaatgtat gatgccttat tgaataaatc aggggcaaca | 960 |
| ggtgtattta ctgatttccc agatactgg | 989 |

<210> SEQ ID NO 5
<211> LENGTH: 989
<212> TYPE: DNA
<213> ORGANISM: Haemophilus influenzae

<400> SEQUENCE: 5

| | |
|---|---|
| gcaaataccc aaatgaaatc tgacaaaatc atcattgctc atcgtggtgc tagcggttat | 60 |
| ttaccagagc atacgttaga atctaaagca cttgcgtttg cacagcacgc tgattactta | 120 |
| gagcaagatt tagcaatgac taaggatggt cgtttagtgg ttattcacga tcacttttta | 180 |
| gatggcttga ctgatgttgc gaaaaaattc ccacatcgtc accgtaaaga tggtcgttac | 240 |
| tatgtcatcg actttacctt aaaagaaatt caaagtttag aaatgacaga aactttgaa | 300 |
| accaaagatg gcaaacagac acaagtttat cctaatcgtt tccccctttg gcaatcccat | 360 |
| ttccgtattc acacctttga agatgaaatt gaatttattc aaggtttaga aaaatcgacg | 420 |
| ggcaaaaaag tagggattta ccagaaaatc aaagcaccct tggttccacca tcaaaatggc | 480 |
| aaagatattg ctgctgaaac gctcaaagtg ttaaaaaaat atggctatga taagaaaacc | 540 |
| gatatggttt acttacaaac tttcgatttt aatgaattaa aacgtatcaa aacggaatta | 600 |

```
cttccacaaa tgggtatgga tttgaaatta gttcaattaa ttgcttatac agattggaaa      660
gaaacacaag aaaaagattc aaggggttat tgggtaaact ataattacga ttggatgttt      720
aaacctggtg caatggcaga agtggttaaa tatgccgatg gtgttggccc aggttggtat     780
atgttagtta ataaagaaga atccaaacct gataatattg tgtacactcc gttggtaaaa     840
gaacttgcac aatataatgt ggaagtgcat ccttacaccg tgcgtaaaga tgcactacct     900 gcgttttca cagacgtaaa tcaaatgtat gatgccttat tgaataaatc aggggcaaca      960
ggtgtattta ctgatttccc agatactgg                                       989
```

<210> SEQ ID NO 6
<211> LENGTH: 1259
<212> TYPE: DNA
<213> ORGANISM: H.influenzae

<400> SEQUENCE: 6

```
acctacggta ctaaataatt agcttaaaaa aggcggcggg caaattgctt agtcgccttt     60
tttgtaacta aaatctaaaa aaaaccataa aaatttaccg cactcttaag gagaaaatac    120
ttatgaaact taaaacttta gcccctttctt tattagcagc tggcgtacta gcaggttgta   180
gcagccattc atcaaatatg gcgaataccc aaatgaaatc agacaaaatc attattgctc    240
accgtggtgc tagcggttat ttaccagagc atacgttaga atctaaagca cttgcgtttg    300
cacaacaggc tgattattta gagcaagatt tagcaatgac taaggatggt cgtttagtgg   360
ttattcacga tcacttttta gatggcttga ctgatgttgc gaaaaaattc ccacatcgtc   420
accgtaaaga tggccgttac tatgtcatcg actttacctt aaaagaaatt caaagtttag    480
aaatgacaga aaactttgaa accaagatg gcaaacaagc gcaagtttat cctaatcgtt    540
tcccactttg gaaatcacat tttagaattc acacctttga agatgaaatt gaattatcc    600 aaggcttaga aaatccact ggcaaaaaag tagggattta tccagaaatc aaagcacctt    660
ggttccacca tcaaatggt aaagatattg ctgctgaaaac gctcaaagtg ttaaaaaaat  720
atggctatga taagaaaacc gatatggttt acttacaaac tttcgatttt aatgaattaa    780
aacgtatcaa aacggaatta cttccacaaa tgggtatgga tttgaaatta gttcaattaa   840
ttgcttatac agattggaaa gaaacacaag aaaaagatcc aaggggttat tgggtaaact  900
ataattacga ttggatgttt aaacctggag caatggcaga agtggttaaa tatgccgatg   960
gtgttggtcc aggttggtat atgttagtta ataaagaaga atccaaacct gataatattg    1020
tgtacactcc gttggtaaaa gaacttgcac aatataatgt ggaagtgcat ccttacaccg    1080
tgcgtaaaga tgcactaccc gcgttttca cagatgtaaa tcaaatgtat gatgccttat    1140
tgaataaatc aggggcaaca ggtgtattta ctgatttccc agatactggc gtggaattct    1200
taaaaggaat aaaataatat ccctcacaac cgtgggtaaa catacccacg ttaactagg     1259
```

<210> SEQ ID NO 7
<211> LENGTH: 1258
<212> TYPE: DNA
<213> ORGANISM: H.influenzae

<400> SEQUENCE: 7

```
acttacggta ctaaataatt agcttaaaaa aggcggtggg taaattgctt agtcgccttt    60
tttgtaacta aaatctaaaa aaaccataaa aatttaccgc actcttaagg agaaaatact   120
tatgaaactt aaaactttag ccctttcttt attagcagct ggcgtactag caggttgtag    180
cagccattca tcaaatatgg cgaataccca aatgaaatca gacaaaatca ttattgctca    240
```

-continued

```
ccgtggtgct agcggttatt taccagagca tacgttagaa tctaaagcac ttgcgtttgc      300
acaacaggct gattatttag agcaagattt agcaatgact aaggatggtc gtttagtggt      360
tattcacgat cacttttag atggcttgac tgatgttgcg aaaaaattcc cacatcgtca       420
ccgtaaagat ggtcgttact atgtcatcga ctttacctta aaagaaattc aaagtttaga      480
aatgacagaa aactttgaaa ccaaagacgg caaacaagcg caagtttatc ctaatcgttt      540
cccactttgg aaatcacatt ttagaattca tacctttgaa gatgaaattg aatttatcca      600
aggcttagaa aaatccactg gcaaaaaagt agggatttat ccagaaatca agcaccttg       660
gttccaccat caaaatggta aagatattgc tgctgaaacg ctcaaagtgt aaaaaaata      720
tggctatgat aagaaaaccg atatggttta cttacaaact ttcgatttta atgaattaaa      780
acgtatcaaa acggaattac ttccacaaat gggatggat ttgaaattag ttcaattaat      840
tgcttataca gattggaaag aaacacaaga aaagaccca aagggttatt gggtaaacta      900
taattacgat tggatgttta aacctggagc aatggcagaa gtggttaaat atgccgatgg      960
tgttggtcca ggttggtata tgttagttaa taaagaagaa tccaaacctg ataatattgt     1020
gtacactccg ttggtaaaag aacttgcaca atataatgtg gaagtgcatc cttacaccgt     1080
gcgtaaagat gcactgcccg agttttcac agacgtaaat caaatgtatg atgtcttatt      1140
gaataaatca ggggcaacag gtgtatttac tgatttccca gatactggcg tggaattctt     1200
aaaaggaata aaataatatc cctcacaacc gtgggtaaac atcccacgt taactagg       1258

<210> SEQ ID NO 8
<211> LENGTH: 1252
<212> TYPE: DNA
<213> ORGANISM: H.influenzae

<400> SEQUENCE: 8
acttacggta ctaaataatt agcttaaaaa aggcggtggg caaattgctt agtcgccttt       60
tttgtaacta aaatctaaaa aaaccataaa aatttaccgc actttcaagg agaaaatact      120
tatgaaactt aaaactttag cccttttcttt attagcagct ggcgtactag caggttgtag      180
cagccattca tcaaatatgg cgaaaaccca aatgaaatca gacaaaatca ttattgctca      240
ccgtggtgct agcggttatt taccagagca tacgttagaa tctaaagcac ttgcgtttgc      300
acaacaggct gattatttag agcaagattt agcaatgact aaggatggtc gtttagtggt      360
tattcacgat cacttttag atggcttgac tgatgttgcg aaaaaattcc cacatcgtca       420
ccgtaaagat ggtcgttact atgtcatcga ctttacctta aaagaaattc aaagtttaga      480
aatgacagaa aactttgaaa ccaaagacgg caaacaagcg caagtttatc ctaatcgttt      540
cccccttggg caatcccatt tccgtattca caccttgaa gatgaaattg aatttatcca      600
aggcttagaa aaatcgactg gcagaaaagt agggatttat ccagaaatca agcaccttg       660
gttccaccat caaaatggta aagatattgc tgctgaaacg ctcaaagtgt tgaaaaaata     720
tggctatgat aagaaaaccg atatggttta cttacaaact ttcgacttta atgaattaaa      780
acgtatcaaa acggaattac ttccacaaat gggtatggat ttgaaattag ttcaattaat     840
tgcttataca gattggaaag aaacacaaga aaagattca aagggttatt gggtaaacta      900
taattacgat tggatgttta aacctggtgc aatggcagaa gtggttaaat atgccgatgg      960
tgttggccca ggttggtata tgttagttaa taaagaagaa tccaaacctg ataatattgt     1020
gtacactccg ttggtaaaag aacttgcaaa atataatgtg gaagtgcatc cttacaccgt     1080
```

```
gcgtaaagat gcactgcctg cgttttcac agacgtaaat caaatgtatg atgctttatt    1140
gaataaatca ggggcaacag gtgtatttac tgatttccca gatactggcg tggaattctt    1200
aaaaggaata gaataatatc cctcacaacc gtgggtaaac atacccacgg tt            1252
```

<210> SEQ ID NO 9
<211> LENGTH: 1864
<212> TYPE: DNA
<213> ORGANISM: Haemophilus influenzae

<400> SEQUENCE: 9

```
gatcggcggt ggcgtattag cggtgttatt actcttaatc gtaatggttg aagaaggaaa      60
acacaaagcg aaattaggcg atacttacgg tactaaataa ttagcttaaa aaaggcggtg     120
ggcaaattgc ttagtcgcct tttttgtaac taaaatctaa aaactctata aaaatttacc     180
gcactcttaa ggagaaaata cttatgaaac ttaaaacttt agcccttct ttattagcag      240 ctggcgtact agcaggttgt agcagccatt catcaaatat ggcgaatacc caaatgaaat     300
cagacaaaat cattattgct caccgtggtg ctagcggtta tttaccagag catacgttag     360
aatctaaagc acttgcgttt gcacaacagg ctgattattt agagcaagat ttagcaatga     420
ctaaggatgg tcgtttagtg gttattcacg atcacttttt agatggcttg actgatgttg     480
cgaaaaaatt cccacatcgt catcgtaaag atggccgtta ctatgtcatc gactttacct     540
taaaagaaat tcaagtttta gaatgacag aaaactttga aaccaaagat ggcaaacaag      600
cgcaagttta tcctaatcgt ttccctcttt ggaaatcaca ttttagaatt catacctttg     660
aagatgaaat tgaatttatc caaggcttag aaaaatccac tggcaaaaaa gtagggattt     720
atccagaaat caaagcacct tggttccacc atcaaaatgg taaagatatt gctgctgaaa     780
cgctcaaagt gttaaaaaaa tatggctatg ataagaaaac cgatatggtt tacttacaaa     840
ctttcgattt taatgaatta aaacgtatca aaacggaatt acttccacaa atgggaatgg     900
atttgaaatt agttcaatta attgcttata cagattggaa agaaacacaa gaaaaagacc     960
caaagggtta ttgggtaaac tataattacg attggatgtt taaacctggt gcaatggcag    1020
aagtggttaa atatgccgat ggtgttggcc caggttggta tatgttagtt aataaagaag    1080
aatccaaacc tgataatatt gtgtacactc cgttggtaaa agaacttgca caatataatg    1140
tggaagtgca tccttacacc gtgcgtaaag atgcactgcc cgagttttc acagacgtaa     1200 atcaaatgta tgatgcctta ttgaataaat caggggcaac aggtgtattt actgatttcc    1260
cagatactgg cgtggaattc ttaaaaggaa taaaataata tccctcacaa ccgtgggtaa    1320
acatacccac ggttaactag gtttctatat cgtagaaact aaaaatctac tctaacagag    1380
taacatcata atcaatctag gtgttctaac ctagaattca ataaggagg ctatttcaaa     1440 acactccgta ttcttttta ataaattctc ttcccttac ttagggaaaa cactcttcat       1500
ttcaaccgca cttctaagga gtgctctatg gataaatcat taaaagcgaa ctgtattggc    1560 gagttttag gtacagcctt attgattttc tttggtgtgg gctgcgttgc agcactaaaa      1620
gtagcaggcg ctagttttgg cttgtgggaa atcagcatta tgtggggat gggcgttgca     1680 cttgcagtat atgcaacagc gggtttatct ggcgcacatt taaaccctgc agtaaccatt    1740 gcccttttgga aatttgcttg ctttgatggc aaaaagtaa ttccttacat catttcacaa    1800
atgctcggcg cattctttgc tgccgcatta gtttatgcct tataccgcaa tgttttatc     1860 gatc                                                                 1864
```

```
<210> SEQ ID NO 10
<211> LENGTH: 25
<212> TYPE: PRT
<213> ORGANISM: H. influenzae

<400> SEQUENCE: 10

Pro Lys Arg Tyr Ala Arg Ser Val Arg Gln Tyr Lys Ile Leu Asn Cys
1               5                   10                  15

Ala Asn Tyr His Leu Thr Gln Val Arg
            20                  25

<210> SEQ ID NO 11
<211> LENGTH: 160
<212> TYPE: PRT
<213> ORGANISM: H. influenzae

<400> SEQUENCE: 11

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 12
<211> LENGTH: 149
<212> TYPE: PRT
<213> ORGANISM: H. influenzae

<400> SEQUENCE: 12

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110
```

```
Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 13
<211> LENGTH: 630
<212> TYPE: PRT
<213> ORGANISM: Moraxella catarrhalis

<400> SEQUENCE: 13

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Leu Asp Glu Asp Val Gly Trp Asn Gln Asn
                85                  90                  95

Asp Ile Ala Asn Leu Glu Asp Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Gly Lys Ile Leu Gln Asn Glu
    130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
    210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Ile
                245                 250                 255

Tyr Glu Leu Ala Gln Gln Gln Asp Gln His Ser Ser Asp Ile Lys Thr
            260                 265                 270

Leu Lys Lys Asn Val Glu Glu Gly Leu Leu Glu Leu Ser Gly His Leu
        275                 280                 285

Ile Asp Gln Lys Thr Asp Ile Ala Gln Asn Ala Asn Ile Gln Asp
    290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
```

```
                    325                 330                 335
Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

Thr Gln Asn Ile Glu Asp Leu Ala Ala Tyr Asn Glu Leu Gln Asp Ala
    370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
                405                 410                 415

Asn Ile Asn Asn Ile Tyr Glu Leu Ala Gln Gln Gln Asp Gln His Ser
            420                 425                 430

Ser Asp Ile Lys Thr Leu Ala Lys Ala Ser Ala Ala Asn Thr Asp Arg
        435                 440                 445

Ile Ala Lys Asn Lys Ala Asp Ala Asp Ala Ser Phe Glu Thr Leu Thr
    450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
                485                 490                 495

Thr Lys Phe Ala Ala Thr Ala Asp Ala Ile Thr Lys Asn Gly Asn Ala
            500                 505                 510

Ile Thr Lys Asn Ala Lys Ser Ile Thr Asp Leu Gly Thr Lys Val Asp
        515                 520                 525

Gly Phe Asp Ser Arg Val Thr Ala Leu Asp Thr Lys Val Asn Ala Phe
    530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
                565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
        595                 600                 605

Gly Ala Ala Ile Asn Thr Ser Gly Asn Lys Lys Gly Ser Tyr Asn Ile
    610                 615                 620

Gly Val Asn Tyr Glu Phe
625                 630

<210> SEQ ID NO 14
<211> LENGTH: 29
<212> TYPE: PRT
<213> ORGANISM: Moraxella catarrhali

<400> SEQUENCE: 14

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala
            20                  25

<210> SEQ ID NO 15
<211> LENGTH: 148
<212> TYPE: PRT
<213> ORGANISM: Moraxella catarrhalis
```

```
<400> SEQUENCE: 15

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
130                 135                 140

Ser Ile Glu Asp
145

<210> SEQ ID NO 16
<211> LENGTH: 154
<212> TYPE: PRT
<213> ORGANISM: Moraxella catarrhalis

<400> SEQUENCE: 16

Lys Asp Ala Ile Ala Lys Asn Asn Glu Ser Ile Glu Asp Leu Tyr Asp
1               5                   10                  15

Phe Gly His Glu Val Ala Glu Ser Ile Gly Glu Ile His Ala His Asn
            20                  25                  30

Glu Ala Gln Asn Glu Thr Leu Lys Gly Leu Ile Thr Asn Ser Ile Glu
        35                  40                  45

Asn Thr Asn Asn Ile Thr Lys Asn Lys Ala Asp Ile Gln Ala Leu Glu
50                  55                  60

Asn Asn Val Val Glu Glu Leu Phe Asn Leu Ser Gly Arg Leu Ile Asp
65                  70                  75                  80

Gln Lys Ala Asp Ile Asp Asn Asn Ile Asn Asn Ile Tyr Glu Leu Ala
                85                  90                  95

Gln Gln Gln Asp Gln His Ser Ser Asp Ile Lys Thr Leu Lys Lys Asn
            100                 105                 110

Val Glu Glu Gly Leu Leu Glu Leu Ser Gly His Leu Ile Asp Gln Lys
        115                 120                 125

Thr Asp Ile Ala Gln Asn Gln Ala Asn Ile Gln Asp Leu Ala Thr Tyr
130                 135                 140

Asn Glu Leu Gln Asp Gln Tyr Ala Gln Lys
145                 150

<210> SEQ ID NO 17
<211> LENGTH: 510
<212> TYPE: PRT
<213> ORGANISM: Moraxella catarrhalis

<400> SEQUENCE: 17

Gln Ala Lys Asn Asp Ile Thr Leu Glu Asp Leu Pro Tyr Leu Ile Lys
```

-continued

```
1               5                   10                  15
Lys Ile Asp Gln Asn Glu Leu Glu Ala Asp Ile Gly Asp Ile Thr Ala
            20                  25                  30
Leu Glu Lys Tyr Leu Ala Leu Ser Gln Tyr Gly Asn Ile Leu Ala Leu
            35                  40                  45
Glu Glu Leu Asn Lys Ala Leu Glu Glu Leu Asp Glu Asp Val Gly Trp
 50                  55                  60
Asn Gln Asn Asp Ile Ala Asn Leu Glu Asp Asp Val Glu Thr Leu Thr
 65                  70                  75                  80
Lys Asn Gln Asn Ala Leu Ala Glu Gln Gly Glu Ala Ile Lys Glu Asp
                85                  90                  95
Leu Gln Gly Leu Ala Asp Phe Val Glu Gly Gln Glu Gly Lys Ile Leu
            100                 105                 110
Gln Asn Glu Thr Ser Ile Lys Lys Asn Thr Gln Arg Asn Leu Val Asn
            115                 120                 125
Gly Phe Glu Ile Glu Lys Asn Lys Asp Ala Ile Ala Lys Asn Asn Glu
            130                 135                 140
Ser Ile Glu Asp Leu Tyr Asp Phe Gly His Glu Val Ala Glu Ser Ile
145                 150                 155                 160
Gly Glu Ile His Ala His Asn Glu Ala Gln Asn Glu Thr Leu Lys Gly
                165                 170                 175
Leu Ile Thr Asn Ser Ile Glu Asn Thr Asn Ile Thr Lys Asn Lys
            180                 185                 190
Ala Asp Ile Gln Ala Leu Glu Asn Asn Val Val Glu Glu Leu Phe Asn
            195                 200                 205
Leu Ser Gly Arg Leu Ile Asp Gln Lys Ala Asp Ile Asp Asn Asn Ile
 210                 215                 220
Asn Asn Ile Tyr Glu Leu Ala Gln Gln Gln Asp Gln His Ser Ser Asp
225                 230                 235                 240
Ile Lys Thr Leu Lys Lys Asn Val Glu Glu Gly Leu Leu Glu Leu Ser
                245                 250                 255
Gly His Leu Ile Asp Gln Lys Thr Asp Ile Ala Gln Asn Gln Ala Asn
            260                 265                 270
Ile Gln Asp Leu Ala Thr Tyr Asn Glu Leu Gln Asp Gln Tyr Ala Gln
            275                 280                 285
Lys Gln Thr Glu Ala Ile Asp Ala Leu Asn Lys Ala Ser Ser Glu Asn
            290                 295                 300
Thr Gln Asn Ile Glu Asp Leu Ala Ala Tyr Asn Glu Leu Gln Asp Ala
305                 310                 315                 320
Tyr Ala Lys Gln Gln Thr Glu Ala Ile Asp Ala Leu Asn Lys Ala Ser
                325                 330                 335
Ser Glu Asn Thr Gln Asn Ile Glu Asp Leu Ala Ala Tyr Asn Glu Leu
            340                 345                 350
Gln Asp Ala Tyr Ala Lys Gln Gln Thr Glu Ala Ile Asp Ala Leu Asn
            355                 360                 365
Lys Ala Ser Ser Glu Asn Thr Gln Asn Ile Ala Lys Asn Gln Ala Asp
            370                 375                 380
Ile Ala Asn Asn Ile Asn Asn Ile Tyr Glu Leu Ala Gln Gln Gln Asp
385                 390                 395                 400
Gln His Ser Ser Asp Ile Lys Thr Leu Ala Lys Ala Ser Ala Ala Asn
                405                 410                 415
Thr Asp Arg Ile Ala Lys Asn Lys Ala Asp Ala Asp Ala Ser Phe Glu
            420                 425                 430
```

```
Thr Leu Thr Lys Asn Gln Asn Thr Leu Ile Glu Lys Asp Lys Glu His
        435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr
                500                 505                 510

<210> SEQ ID NO 18
<211> LENGTH: 46
<212> TYPE: PRT
<213> ORGANISM: Moraxella catarrhalis

<400> SEQUENCE: 18

Ser Ile Thr Asp Leu Gly Thr Lys Val Asp Gly Phe Asp Ser Arg Val
1               5                   10                  15

Thr Ala Leu Asp Thr Lys Val Asn Ala Phe Asp Gly Arg Ile Thr Ala
                20                  25                  30

Leu Asp Ser Lys Val Glu Asn Gly Met Ala Ala Gln Ala Ala
            35                  40                  45

<210> SEQ ID NO 19
<211> LENGTH: 40
<212> TYPE: PRT
<213> ORGANISM: Moraxella catarrhalis

<400> SEQUENCE: 19

Ile Thr Asp Leu Gly Thr Lys Val Asp Gly Phe Asp Ser Arg Val Thr
1               5                   10                  15

Ala Leu Asp Thr Lys Val Asn Ala Phe Asp Gly Arg Ile Thr Ala Leu
                20                  25                  30

Asp Ser Lys Val Glu Asn Gly Met
            35                  40

<210> SEQ ID NO 20
<211> LENGTH: 55
<212> TYPE: PRT
<213> ORGANISM: Moraxella catarrhalis

<400> SEQUENCE: 20

Lys Phe Asn Ala Thr Ala Ala Leu Gly Gly Tyr Gly Ser Lys Ser Ala
1               5                   10                  15

Val Ala Ile Gly Ala Gly Tyr Arg Val Asn Pro Asn Leu Ala Phe Lys
                20                  25                  30

Ala Gly Ala Ala Ile Asn Thr Ser Gly Asn Lys Lys Gly Ser Tyr Asn
            35                  40                  45

Ile Gly Val Asn Tyr Glu Phe
        50                  55

<210> SEQ ID NO 21
<211> LENGTH: 613
<212> TYPE: PRT
<213> ORGANISM: Moraxella catarrhalis

<400> SEQUENCE: 21

Met Lys Thr Met Lys Leu Leu Pro Leu Lys Ile Ala Val Thr Ser Ala
```

-continued

```
1               5                   10                  15
Met Ile Ile Gly Leu Gly Ala Ala Ser Thr Ala Asn Ala Gln Ser Arg
            20                  25                  30
Asp Arg Ser Leu Glu Asp Ile Gln Asp Ser Ile Ser Lys Leu Val Gln
            35                  40                  45
Asp Asp Ile Asn Thr Leu Lys Gln Asp Gln Gln Lys Met Asn Lys Tyr
            50                  55                  60
Leu Leu Leu Asn Gln Leu Ala Asn Thr Leu Ile Thr Asp Glu Leu Asn
65                  70                  75                  80
Asn Asn Val Ile Lys Asn Thr Asn Ser Ile Glu Ala Leu Gly Asp Glu
                85                  90                  95
Ile Gly Trp Leu Glu Asn Asp Ile Ala Asp Leu Glu Glu Gly Val Glu
            100                 105                 110
Glu Leu Thr Lys Asn Gln Asn Thr Leu Ile Glu Lys Asp Glu Glu His
            115                 120                 125
Asp Arg Leu Ile Ala Gln Asn Gln Ala Asp Ile Gln Thr Leu Glu Asn
            130                 135                 140
Asn Val Val Glu Glu Leu Phe Asn Leu Ser Gly Arg Leu Ile Asp Gln
145                 150                 155                 160
Glu Ala Asp Ile Ala Lys Asn Asn Ala Ser Ile Glu Glu Leu Tyr Asp
                165                 170                 175
Phe Asp Asn Glu Val Ala Glu Arg Ile Gly Glu Ile His Ala Tyr Thr
            180                 185                 190
Glu Glu Val Asn Lys Thr Leu Glu Asn Leu Ile Thr Asn Ser Val Lys
                195                 200                 205
Asn Thr Asp Asn Ile Asp Lys Asn Lys Ala Asp Ile Asp Asn Asn Ile
210                 215                 220
Asn His Ile Tyr Glu Leu Ala Gln Gln Asp Gln His Ser Ser Asp
225                 230                 235                 240
Ile Lys Thr Leu Lys Asn Asn Val Glu Glu Gly Leu Leu Glu Leu Ser
                245                 250                 255
Gly His Leu Ile Asp Gln Lys Ala Asp Leu Thr Lys Asp Ile Lys Ala
            260                 265                 270
Leu Glu Ser Asn Val Glu Glu Gly Leu Leu Asp Leu Ser Gly Arg Leu
            275                 280                 285
Leu Asp Gln Lys Ala Asp Leu Thr Lys Asp Ile Lys Ala Leu Glu Ser
            290                 295                 300
Asn Val Glu Glu Gly Leu Leu Asp Leu Ser Gly Arg Leu Leu Asp Gln
305                 310                 315                 320
Lys Ala Asp Ile Ala Gln Asn Gln Thr Asp Ile Gln Asp Leu Ala Ala
                325                 330                 335
Tyr Asn Glu Leu Gln Asp Gln Tyr Ala Gln Lys Gln Thr Glu Ala Ile
            340                 345                 350
Asp Ala Leu Asn Lys Ala Ser Ser Glu Asn Thr Gln Asn Ile Glu Asp
            355                 360                 365
Leu Ala Ala Tyr Asn Glu Leu Gln Asp Ala Tyr Ala Lys Gln Gln Thr
            370                 375                 380
Glu Ala Ile Asp Ala Leu Asn Lys Ala Ser Ser Glu Asn Thr Gln Asn
385                 390                 395                 400
Ile Ala Lys Asn Gln Ala Asp Ile Ala Asn Asn Ile Asn Asn Ile Tyr
                405                 410                 415
Glu Leu Ala Gln Gln Gln Asp Gln His Ser Ser Asp Ile Lys Thr Leu
            420                 425                 430
```

```
Ala Lys Ala Ser Ala Ala Asn Thr Asn Arg Ile Ala Thr Ala Glu Leu
            435                 440                 445

Gly Ile Ala Glu Asn Lys Lys Asp Ala Gln Ile Ala Lys Ala Gln Ala
        450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
            515                 520                 525

Gly Arg Ile Thr Ala Leu Asp Ser Lys Val Glu Asn Gly Met Ala Ala
        530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
            595                 600                 605

Val Asn Tyr Glu Phe
        610

<210> SEQ ID NO 22
<211> LENGTH: 644
<212> TYPE: PRT
<213> ORGANISM: Moraxella catarrhalis

<400> SEQUENCE: 22

Met Lys Thr Met Lys Leu Leu Pro Leu Lys Ile Ala Val Thr Ser Ala
1               5                   10                  15

Leu Ile Ile Gly Leu Gly Ala Ala Ser Thr Ala Asn Ala Gln Gln Gln
            20                  25                  30

Leu Gln Thr Glu Thr Phe Leu Pro Asn Phe Leu Ser Asn Asp Asn Tyr
        35                  40                  45

Asp Leu Thr Asp Pro Phe Tyr His Asn Met Ile Leu Gly Asp Thr Ala
50                  55                  60

Leu Leu Asp Lys Gln Asp Gly Ser Gln Pro Gln Leu Lys Phe Tyr Ser
65                  70                  75                  80

Asn Asp Lys Asp Ser Val Pro Asp Ser Leu Leu Phe Ser Lys Leu Leu
                85                  90                  95

His Glu Gln Gln Leu Asn Gly Phe Lys Lys Gly Asp Thr Ile Ile Pro
            100                 105                 110

Leu Asp Lys Asp Gly Lys Pro Val Tyr Gln Val Asp Tyr Lys Leu Asp
        115                 120                 125

Gly Lys Gly Lys Lys Gln Lys Arg Arg Gln Val Tyr Ser Val Thr Thr
    130                 135                 140

Lys Thr Ala Thr Asp Asp Val Asn Ser Ala Tyr Ser Arg Gly Ile
145                 150                 155                 160

Leu Gly Lys Val Asp Asp Leu Asp Asp Glu Met Asn Phe Leu Asn His
                165                 170                 175

Asp Ile Thr Ser Leu Tyr Asp Val Thr Ala Asn Gln Gln Asp Ala Ile
```

-continued

```
                180                 185                 190
Lys Asp Leu Lys Lys Gly Val Lys Gly Leu Asn Lys Glu Leu Lys Glu
            195                 200                 205

Leu Asp Lys Glu Val Gly Val Leu Ser Arg Asp Ile Gly Ser Leu Asn
            210                 215                 220

Asp Asp Val Ala Gln Asn Glu Ser Ile Glu Asp Leu Tyr Asp Phe
225                 230                 235                 240

Ser Gln Glu Val Ala Asp Ser Ile Gly Glu Ile His Ala His Asn Lys
                245                 250                 255

Ala Gln Asn Glu Thr Leu Gln Asp Leu Ile Thr Asn Ser Val Glu Asn
            260                 265                 270

Thr Asn Asn Ile Thr Lys Asn Lys Ala Asp Ile Gln Ala Leu Glu Asn
            275                 280                 285

Asn Val Val Glu Glu Leu Phe Asn Leu Ser Gly Arg Leu Ile Asp Gln
            290                 295                 300

Lys Ala Asp Leu Thr Lys Asp Ile Lys Thr Leu Glu Ser Asn Val Glu
305                 310                 315                 320

Glu Gly Leu Leu Glu Leu Ser Gly His Leu Ile Asp Gln Lys Ala Asp
                325                 330                 335

Ile Ala Lys Asn Gln Ala Asp Ile Ala Gln Asn Gln Ala Asn Ile Gln
            340                 345                 350

Asp Leu Ala Ala Tyr Asn Glu Leu Gln Asp Ala Tyr Ala Lys Gln Gln
            355                 360                 365

Thr Glu Ala Ile Asp Ala Leu Asn Lys Ala Ser Ser Glu Asn Thr Gln
            370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
            405                 410                 415

Asn Thr Gln Asn Ile Ala Lys Asn Gln Ala Asp Ile Ala Asn Asn Ile
            420                 425                 430

Asn Asn Ile Tyr Glu Leu Ala Gln Gln Gln Asp Gln His Ser Ser Asp
            435                 440                 445

Ile Lys Thr Leu Ala Lys Ala Ser Ala Ala Asn Thr Asp Arg Ile Ala
            450                 455                 460

Lys Asn Lys Ala Asp Ala Asp Ala Ser Phe Glu Thr Leu Thr Lys Asn
465                 470                 475                 480

Gln Asn Thr Leu Ile Glu Lys Asp Lys Glu His Asp Lys Leu Ile Thr
            485                 490                 495

Ala Asn Lys Thr Ala Ile Asp Glu Asn Lys Ala Ser Ala Asp Thr Lys
            500                 505                 510

Phe Ala Ala Thr Ala Asp Ala Ile Thr Lys Asn Gly Asn Ala Ile Thr
            515                 520                 525

Lys Asn Ala Lys Ser Ile Thr Asp Leu Gly Thr Lys Val Asp Gly Phe
            530                 535                 540

Asp Ser Arg Val Thr Ala Leu Asp Thr Lys Val Asn Ala Phe Asp Gly
545                 550                 555                 560

Arg Ile Thr Ala Leu Asp Ser Lys Val Glu Asn Gly Met Ala Ala Gln
            565                 570                 575

Ala Ala Leu Ser Gly Leu Phe Gln Pro Tyr Ser Val Gly Lys Phe Asn
            580                 585                 590

Ala Thr Ala Ala Leu Gly Gly Tyr Gly Ser Lys Ser Ala Val Ala Ile
            595                 600                 605
```

Gly Ala Gly Tyr Arg Val Asn Pro Asn Leu Ala Phe Lys Ala Gly Ala
            610                 615                 620

Ala Ile Asn Thr Ser Gly Asn Lys Lys Gly Ser Tyr Asn Ile Gly Val
625                 630                 635                 640

Asn Tyr Glu Phe

<210> SEQ ID NO 23
<211> LENGTH: 591
<212> TYPE: PRT
<213> ORGANISM: Moraxella catarrhalis

<400> SEQUENCE: 23

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Leu Val
            20                  25                  30

Glu Arg Phe Phe Pro Asn Ile Phe Leu Asp Lys Pro Leu Ala Lys Gln
        35                  40                  45

His Tyr His Asn Val Val Val Gly Asp Thr Ser Ile Val Ser Asp Leu
    50                  55                  60

Gln Ser Asn Ser Asp Gln Leu Lys Phe Tyr Ser Asp Asp Glu Gly Leu
65                  70                  75                  80

Val Pro Asp Ser Leu Leu Phe Asn Lys Met Leu His Glu Gln Leu Leu
                85                  90                  95

Asn Gly Phe Lys Glu Gly Asp Thr Ile Ile Pro Leu Asp Glu Asn Gly
            100                 105                 110

Lys Pro Val Tyr Lys Val Asp Tyr Lys Leu Asp Gly Lys Glu Pro Arg
        115                 120                 125

Lys Val Tyr Ser Val Thr Thr Lys Ile Ala Thr Ala Glu Asp Val Ala
    130                 135                 140

Thr Ser Ser Tyr Ala Asn Gly Ile Gln Lys Asp Ile Asp Asp Leu Tyr
145                 150                 155                 160

Asp Phe Asp His Gln Val Thr Glu Arg Leu Thr Gln His Gly Lys Thr
                165                 170                 175

Ile Tyr Arg Asn Gly Glu Arg Ile Leu Ala Asn Glu Glu Ser Val Gln
            180                 185                 190

Tyr Leu Asn Lys Glu Val Gln Asn Asn Ile Glu His Ile Tyr Glu Leu
        195                 200                 205

Ala Gln Gln Gln Asp Gln His Ser Ser Asp Ile Lys Thr Leu Glu Ser
    210                 215                 220

Asn Val Glu Lys Gly Leu Leu Glu Leu Ser Gly His Leu Ile Asp Gln
225                 230                 235                 240

Lys Ala Asp Leu Thr Lys Asp Ile Lys Thr Leu Glu Ser Asn Val Glu
                245                 250                 255

Glu Gly Leu Leu Asp Leu Ser Gly Arg Leu Ile Asp Gln Lys Ala Asp
            260                 265                 270

Leu Thr Lys Asp Ile Lys Thr Leu Glu Ser Asn Val Glu Glu Gly Leu
        275                 280                 285

Leu Asp Leu Ser Gly Arg Leu Ile Asp Gln Lys Ala Asp Ile Ala Gln
    290                 295                 300

Asn Gln Ala Asn Ile Gln Asp Leu Ala Ala Tyr Asn Glu Leu Gln Asp
305                 310                 315                 320

Gln Tyr Ala Gln Lys Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Thr Glu Ala Ile Asp Ala Leu
        355                 360                 365

Asn Lys Ala Ser Ser Glu Asn Thr Gln Asn Ile Ala Lys Asn Gln Ala
370                 375                 380

Asp Ile Ala Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
        405                 410                 415

Asn Thr Asn Arg Ile Ala Thr Ala Glu Leu Gly Ile Ala Glu Asn Lys
            420                 425                 430

Lys Asp Ala Gln Ile Ala Lys Ala Gln Ala Asn Ala Asn Lys Thr Ala
        435                 440                 445

Ile Asp Glu Asn Lys Ala Ser Ala Asp Thr Lys Phe Ala Ala Thr Ala
450                 455                 460

Asp Ala Ile Thr Lys Asn Gly Asn Ala Ile Thr Lys Asn Ala Lys Ser
465                 470                 475                 480

Ile Thr Asp Leu Gly Thr Lys Val Asp Gly Phe Asp Ser Arg Val Thr
            485                 490                 495

Ala Leu Asp Thr Lys Val Asn Ala Phe Asp Gly Arg Ile Thr Ala Leu
        500                 505                 510

Asp Ser Lys Val Glu Asn Gly Met Ala Ala Gln Ala Ala Leu Ser Gly
        515                 520                 525

Leu Phe Gln Pro Tyr Ser Val Gly Lys Phe Asn Ala Thr Ala Ala Leu
530                 535                 540

Gly Gly Tyr Gly Ser Lys Ser Ala Val Ala Ile Gly Ala Gly Tyr Arg
545                 550                 555                 560

Val Asn Pro Asn Leu Ala Phe Lys Ala Gly Ala Ala Ile Asn Thr Ser
            565                 570                 575

Gly Asn Lys Lys Gly Ser Tyr Asn Ile Gly Val Asn Tyr Glu Phe
        580                 585                 590

<210> SEQ ID NO 24
<211> LENGTH: 687
<212> TYPE: PRT
<213> ORGANISM: Moraxella catarrhalis

<400> SEQUENCE: 24

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
            20                  25                  30

Gln Gln Gln Gln Gln Gln Gln Ser Arg Thr Glu Ile Phe Phe Pro
        35                  40                  45

Asn Ile Phe Phe Asn Glu Asn His Asp Glu Leu Asp Asp Ala Tyr His
        50                  55                  60

Asn Ile Ile Leu Gly Asp Thr Ala Leu Leu Asp Lys Gln Asp Gly Ser
65                  70                  75                  80

Gln Pro Gln Leu Lys Phe Tyr Ser Asn Asp Lys Asp Ser Val Pro Asp
            85                  90                  95

Ser Leu Leu Phe Ser Lys Leu Leu His Glu Gln Gln Leu Asn Gly Phe
            100                 105                 110

Lys Lys Gly Asp Thr Ile Ile Pro Leu Asp Lys Asp Gly Lys Pro Val

```
                   115                 120                 125
Tyr Gln Val Asp Tyr Lys Leu Asp Gly Lys Gly Lys Gln Lys Arg
            130                 135                 140
Arg Gln Val Tyr Ser Val Thr Thr Lys Thr Ala Thr Asp Asp Val
145                 150                 155                 160
Asn Ser Ala Tyr Ser Arg Gly Ile Leu Gly Lys Val Asp Leu Asp
                165                 170                 175
Asp Glu Met Asn Phe Leu Asn His Asp Ile Thr Ser Leu Tyr Asp Val
                180                 185                 190
Thr Ala Asn Gln Gln Asp Ala Ile Lys Gly Leu Lys Lys Gly Val Lys
                195                 200                 205
Gly Leu Asn Lys Glu Leu Lys Glu Leu Asp Lys Glu Val Gly Val Leu
            210                 215                 220
Ser Arg Asp Ile Gly Ser Leu Asn Asp Asp Val Ala Gln Asn Asn Glu
225                 230                 235                 240
Ser Ile Glu Asp Leu Tyr Asp Phe Ser Gln Glu Val Ala Asp Ser Ile
                245                 250                 255
Gly Glu Ile His Ala His Asn Lys Ala Gln Asn Glu Thr Leu Gln Asp
                260                 265                 270
Leu Ile Thr Asn Ser Val Glu Asn Thr Asn Asn Ile Thr Lys Asn Lys
            275                 280                 285
Ala Asp Ile Gln Ala Leu Glu Asn Asn Val Val Glu Glu Leu Phe Asn
290                 295                 300
Leu Ser Gly Arg Leu Ile Asp Gln Lys Ala Asp Leu Thr Lys Asp Ile
305                 310                 315                 320
Lys Thr Leu Glu Ser Asn Val Glu Glu Gly Leu Leu Glu Leu Ser Gly
                325                 330                 335
His Leu Ile Asp Gln Lys Ala Asp Ile Ala Lys Asn Gln Ala Asp Ile
            340                 345                 350
Ala Gln Asn Gln Ala Asn Ile Gln Asp Leu Ala Ala Tyr Asn Glu Leu
            355                 360                 365
Gln Asp Ala Tyr Ala Lys Gln Gln Thr Glu Ala Ile Asp Ala Leu Asn
            370                 375                 380
Lys Ala Ser Ser Glu Asn Thr Gln Asn Ile Glu Asp Leu Ala Ala Tyr
385                 390                 395                 400
Asn Glu Leu Gln Asp Ala Tyr Ala Lys Gln Gln Thr Glu Ala Ile Asp
                405                 410                 415
Ala Leu Asn Lys Ala Ser Ser Glu Asn Thr Gln Asn Ile Glu Asp Leu
            420                 425                 430
Ala Ala Tyr Asn Glu Leu Gln Asp Ala Tyr Ala Lys Gln Gln Thr Glu
            435                 440                 445
Ala Ile Asp Ala Leu Asn Lys Ala Ser Ser Glu Thr Gln Asn Ile
            450                 455                 460
Ala Lys Asn Gln Ala Asp Ile Ala Asn Asn Ile Asn Asn Ile Tyr Glu
465                 470                 475                 480
Leu Ala Gln Gln Gln Asp Gln His Ser Ser Asp Ile Lys Thr Leu Ala
                485                 490                 495
Lys Ala Ser Ala Ala Asn Thr Asp Arg Ile Ala Lys Asn Lys Ala Asp
                500                 505                 510
Ala Asp Ala Ser Phe Glu Thr Leu Thr Lys Asn Gln Asn Thr Leu Ile
            515                 520                 525
Glu Lys Asp Lys Glu His Asp Lys Leu Ile Thr Ala Asn Lys Thr Ala
            530                 535                 540
```

```
Ile Asp Glu Asn Lys Ala Ser Ala Asp Thr Lys Phe Ala Thr Ala
545                 550                 555                 560

Asp Ala Ile Thr Lys Asn Gly Asn Ala Ile Thr Lys Asn Ala Lys Ser
            565                 570                 575

Ile Thr Asp Leu Gly Thr Lys Val Asp Ala Phe Asp Gly Arg Val Thr
                580                 585                 590

Ala Leu Asp Thr Lys Val Asn Ala Phe Asp Gly Arg Ile Thr Ala Leu
            595                 600                 605

Asp Ser Lys Val Glu Asn Gly Met Ala Ala Gln Ala Ala Leu Ser Gly
            610                 615                 620

Leu Phe Gln Pro Tyr Ser Val Gly Lys Phe Asn Ala Thr Ala Ala Leu
625                 630                 635                 640

Gly Gly Tyr Gly Ser Lys Ser Ala Val Ala Ile Gly Ala Gly Tyr Arg
                645                 650                 655

Val Asn Pro Asn Leu Ala Phe Lys Ala Gly Ala Ala Ile Asn Thr Ser
                660                 665                 670

Gly Asn Lys Lys Gly Ser Tyr Asn Ile Gly Val Asn Tyr Glu Phe
                675                 680                 685

<210> SEQ ID NO 25
<211> LENGTH: 683
<212> TYPE: PRT
<213> ORGANISM: Moraxella catarrhalis

<400> SEQUENCE: 25

Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
            20                  25                  30

Lys Ser Pro Lys Thr Glu Thr Phe Leu Pro Asn Ile Phe Phe Asn Glu
        35                  40                  45

Tyr Ala Asp Asp Leu Asp Thr Leu Tyr His Asn Met Ile Leu Gly Asp
    50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Ile Pro Leu Asp Glu
            100                 105                 110

Asn Gly Lys Pro Val Tyr Lys Leu Asp Lys Arg Leu Glu Asn Gly Val
        115                 120                 125

Gln Lys Thr Val Tyr Ser Val Thr Thr Lys Thr Ala Thr Ala Asp Asp
    130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Arg Glu Val
            180                 185                 190

Gln Asn Asn Ile Glu Asn Ile His Glu Leu Ala Gln Gln Gln Asp Gln
        195                 200                 205

His Ser Ser Asp Ile Lys Thr Leu Lys Lys Asn Val Glu Lys Asp Leu
    210                 215                 220

Leu Asp Leu Ser Gly Arg Leu Ile Ala Gln Lys Glu Asp Ile Ala Gln
```

-continued

```
            225                 230                 235                 240
Asn Gln Thr Asp Ile Gln Asp Leu Ala Thr Tyr Asn Glu Leu Gln Asp
                245                 250                 255
Gln Tyr Ala Gln Lys Gln Thr Glu Ala Ile Asp Ala Leu Asn Lys Ala
                260                 265                 270
Ser Ser Glu Asn Thr Gln Asn Ile Ala Lys Asn Ser Asn His Ile Lys
                275                 280                 285
Thr Leu Glu Asn Asn Ile Glu Glu Gly Leu Leu Glu Leu Ser Gly His
                290                 295                 300
Leu Ile Asp Gln Lys Ala Asp Leu Thr Lys Asp Ile Lys Ala Leu Glu
305                 310                 315                 320
Ser Asn Val Glu Glu Gly Leu Leu Asp Leu Ser Gly Arg Leu Ile Asp
                325                 330                 335
Gln Lys Ala Asp Ile Ala Gln Asn Gln Ala Asn Ile Gln Asp Leu Ala
                340                 345                 350
Ala Tyr Asn Glu Leu Gln Asp Ala Tyr Ala Lys Gln Gln Thr Glu Ala
                355                 360                 365
Ile Asp Ala Leu Asn Lys Ala Ser Ser Glu Asn Thr Gln Asn Ile Glu
                370                 375                 380
Asp Leu Ala Ala Tyr Asn Glu Leu Gln Asp Ala Tyr Ala Lys Gln Gln
385                 390                 395                 400
Thr Glu Ala Ile Asp Ala Leu Asn Lys Ala Ser Ser Glu Asn Thr Gln
                405                 410                 415
Asn Ile Glu Asp Leu Ala Ala Tyr Asn Glu Leu Gln Asp Ala Tyr Ala
                420                 425                 430
Lys Gln Gln Thr Glu Ala Ile Asp Ala Leu Asn Lys Ala Ser Ser Glu
                435                 440                 445
Asn Thr Gln Asn Ile Ala Lys Asn Gln Ala Asp Ile Ala Asn Asn Ile
                450                 455                 460
Asn Asn Ile Tyr Glu Leu Ala Gln Gln Gln Asp Gln His Ser Ser Asp
465                 470                 475                 480
Ile Lys Thr Leu Ala Lys Ala Ser Ala Ala Asn Thr Asp Arg Ile Ala
                485                 490                 495
Lys Asn Lys Ala Asp Ala Asp Ala Ser Phe Glu Thr Leu Thr Lys Asn
                500                 505                 510
Gln Asn Thr Leu Ile Glu Lys Asp Lys Glu His Asp Lys Leu Ile Thr
                515                 520                 525
Ala Asn Lys Thr Ala Ile Asp Ala Asn Lys Ala Ser Ala Asp Thr Lys
                530                 535                 540
Phe Ala Ala Thr Ala Asp Ala Ile Thr Lys Asn Gly Asn Ala Ile Thr
545                 550                 555                 560
Lys Asn Ala Lys Ser Ile Thr Asp Leu Gly Thr Lys Val Asp Gly Phe
                565                 570                 575
Asp Gly Arg Val Thr Ala Leu Asp Thr Lys Val Asn Ala Leu Asp Thr
                580                 585                 590
Lys Val Asn Ala Phe Asp Gly Arg Ile Thr Ala Leu Asp Ser Lys Val
                595                 600                 605
Glu Asn Gly Met Ala Ala Gln Ala Ala Leu Ser Gly Leu Phe Gln Pro
                610                 615                 620
Tyr Ser Val Gly Lys Phe Asn Ala Thr Ala Ala Leu Gly Gly Tyr Gly
625                 630                 635                 640
Ser Lys Ser Ala Val Ala Ile Gly Ala Gly Tyr Arg Val Asn Pro Asn
                645                 650                 655
```

Leu Ala Phe Lys Ala Gly Ala Ala Ile Asn Thr Ser Gly Asn Lys Lys
                660                 665                 670

Gly Ser Tyr Asn Ile Gly Val Asn Tyr Glu Phe
        675                 680

<210> SEQ ID NO 26
<211> LENGTH: 684
<212> TYPE: PRT
<213> ORGANISM: Moraxella catarrhalis

<400> SEQUENCE: 26

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Gly Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu

```
                    340                 345                 350
Ala Ala Tyr Asn Glu Leu Gln Asp Ala Tyr Ala Lys Gln Gln Thr Glu
                355                 360                 365

Ala Ile Asp Ala Leu Asn Lys Ala Ser Ser Glu Asn Thr Gln Asn Ile
            370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
        435                 440                 445

Glu Asn Thr Gln Asn Ile Ala Lys Asn Gln Ala Asp Ile Ala Asn Asn
    450                 455                 460

Ile Asn Asn Ile Tyr Glu Leu Ala Gln Gln Asp Gln His Ser Ser
465                 470                 475                 480

Asp Ile Lys Thr Leu Ala Lys Ala Ser Ala Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
        515                 520                 525

Thr Ala Asn Lys Thr Ala Ile Asp Ala Asn Lys Ala Ser Ala Asp Thr
    530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
        595                 600                 605

Val Glu Asn Gly Met Ala Ala Gln Ala Ala Leu Ser Gly Leu Phe Gln
    610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
        675                 680

<210> SEQ ID NO 27
<211> LENGTH: 684
<212> TYPE: PRT
<213> ORGANISM: Moraxella catarrhalis

<400> SEQUENCE: 27

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
            20                  25                  30
```

```
Gln Lys Thr Lys Thr Glu Val Phe Leu Pro Asn Leu Phe Asp Asn Asp
             35                  40                  45

Tyr Tyr Asp Leu Thr Asp Pro Leu Tyr His Ser Met Ile Leu Gly Asp
 50                  55                  60

Thr Ala Thr Leu Phe Asp Gln Gln Asp Asn Ser Lys Ser Gln Leu Lys
 65                  70                  75                  80

Phe Tyr Ser Asn Asp Lys Asp Ser Val Pro Asp Ser Leu Leu Phe Ser
                 85                  90                  95

Lys Leu Leu His Glu Gln Gln Leu Asn Gly Phe Lys Ala Gly Asp Thr
                100                 105                 110

Ile Ile Pro Leu Asp Lys Asp Gly Lys Pro Val Tyr Thr Gln Asp Thr
            115                 120                 125

Arg Thr Lys Asp Gly Lys Val Glu Thr Val Tyr Ser Val Thr Thr Lys
130                 135                 140

Ile Ala Thr Gln Asp Asp Val Glu Gln Ser Ala Tyr Ser Arg Gly Ile
145                 150                 155                 160

Gln Gly Asp Ile Asp Asp Leu Tyr Asp Ile Asn Arg Glu Val Asn Glu
                165                 170                 175

Tyr Leu Lys Ala Thr His Asp Tyr Asn Glu Arg Gln Thr Glu Ala Ile
            180                 185                 190

Asp Ala Leu Asn Lys Ala Ser Ser Ala Asn Thr Asp Arg Ile Asp Thr
            195                 200                 205

Ala Glu Glu Arg Ile Asp Lys Asn Glu Tyr Asp Ile Lys Ala Leu Glu
        210                 215                 220

Ser Asn Val Gly Lys Asp Leu Leu Asp Leu Ser Gly Arg Leu Ile Ala
225                 230                 235                 240

Gln Lys Glu Asp Ile Asp Asn Asn Ile Asn His Ile Tyr Glu Leu Ala
                245                 250                 255

Gln Gln Gln Asp Gln His Ser Ser Asp Ile Lys Thr Leu Lys Asn Asn
            260                 265                 270

Val Glu Glu Gly Leu Leu Glu Leu Ser Gly His Leu Ile Asp Gln Lys
            275                 280                 285

Ala Asp Leu Thr Lys Asp Ile Lys Thr Leu Glu Asn Asn Ile Glu Glu
        290                 295                 300

Gly Leu Leu Glu Leu Ser Gly His Leu Ile Asp Gln Lys Ala Asp Leu
305                 310                 315                 320

Thr Lys Asp Ile Lys Thr Leu Glu Asn Asn Ile Glu Glu Gly Leu Leu
                325                 330                 335

Glu Leu Ser Gly His Leu Ile Asp Gln Lys Ala Asp Ile Ala Gln Asn
            340                 345                 350

Gln Ala Asn Ile Gln Asp Leu Ala Ala Tyr Asn Glu Leu Gln Asp Gln
            355                 360                 365

Tyr Ala Gln Lys Gln Thr Glu Ala Ile Asp Ala Leu Asn Lys Ala Ser
        370                 375                 380

Ser Glu Asn Thr Gln Asn Ile Glu Asp Leu Ala Ala Tyr Asn Glu Leu
385                 390                 395                 400

Gln Asp Ala Tyr Ala Lys Gln Gln Thr Glu Ala Ile Asp Ala Leu Asn
                405                 410                 415

Lys Ala Ser Ser Glu Asn Thr Gln Asn Ile Glu Asp Leu Ala Ala Tyr
            420                 425                 430

Asn Glu Leu Gln Asp Ala Tyr Ala Lys Gln Gln Thr Glu Ala Ile Asp
            435                 440                 445

Ala Leu Asn Lys Ala Ser Ser Glu Asn Thr Gln Asn Ile Ala Lys Asn
```

```
                450             455             460
Gln Ala Asp Ile Ala Asn Asn Ile Asn Asn Ile Tyr Glu Leu Ala Gln
465                 470                 475                 480

Gln Gln Asp Gln His Ser Ser Asp Ile Lys Thr Leu Ala Lys Val Ser
                485                 490                 495

Ala Ala Asn Thr Asp Arg Ile Ala Lys Asn Lys Ala Asp Ala Asp Ala
            500                 505                 510

Ser Phe Glu Thr Leu Thr Lys Asn Gln Asn Thr Leu Ile Glu Lys Asp
        515                 520                 525

Lys Glu His Asp Lys Leu Ile Thr Ala Asn Lys Thr Ala Ile Asp Ala
    530                 535                 540

Asn Lys Ala Ser Ala Asp Thr Lys Phe Ala Ala Thr Ala Asp Ala Ile
545                 550                 555                 560

Thr Lys Asn Gly Asn Ala Ile Thr Lys Asn Ala Lys Ser Ile Thr Asp
                565                 570                 575

Leu Gly Thr Lys Val Asp Gly Phe Asp Gly Arg Val Thr Ala Leu Asp
            580                 585                 590

Thr Lys Val Asn Ala Phe Asp Gly Arg Ile Thr Ala Leu Asp Ser Lys
        595                 600                 605

Val Glu Asn Gly Met Ala Ala Gln Ala Ala Leu Ser Gly Leu Phe Gln
    610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
        675                 680

<210> SEQ ID NO 28
<211> LENGTH: 684
<212> TYPE: PRT
<213> ORGANISM: Moraxella catarrhalis

<400> SEQUENCE: 28

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
                20                  25                  30

Lys Ser Pro Lys Thr Glu Ile Phe Leu Pro Asn Leu Phe Asp Asn Asp
            35                  40                  45

Asn Thr Glu Leu Thr Asp Pro Leu Tyr His Asn Met Ile Leu Gly Asn
        50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Lys Gly Asp Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
    130                 135                 140
```

-continued

```
Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
            165                 170                 175

Asp Lys Ile Phe Ala Asn Glu Glu Ser Val Gln Tyr Leu Asn Arg Glu
            180                 185                 190

Val Gln Asn Asn Ile Glu Asn Ile Tyr Glu Leu Val Gln Gln Gln Asp
            195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
            245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
    275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
            325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
    370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
            405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
    450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Ala Asn Thr Asp Arg Ile
            485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
    530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
```

```
                        565                 570                 575
            Phe Asp Gly Arg Val Thr Ala Leu Asp Thr Lys Val Asn Ala Leu Asp
                        580                 585                 590

Thr Lys Val Asn Ala Phe Asp Gly Arg Ile Thr Ala Leu Asp Ser Lys
                        595                 600                 605

Val Glu Asn Gly Met Ala Ala Gln Ala Ala Leu Ser Gly Leu Phe Gln
                        610                 615                 620

Pro Tyr Ser Val Gly Lys Phe Asn Ala Thr Ala Ala Leu Gly Gly Tyr
            625                 630                 635                 640

Gly Ser Lys Ser Ala Val Ala Ile Gly Ala Gly Tyr Arg Val Asn Pro
                        645                 650                 655

Asn Leu Ala Phe Lys Ala Gly Ala Ala Ile Asn Thr Ser Gly Asn Lys
                        660                 665                 670

Lys Gly Ser Tyr Asn Ile Gly Val Asn Tyr Glu Phe
                        675                 680

<210> SEQ ID NO 29
<211> LENGTH: 574
<212> TYPE: PRT
<213> ORGANISM: Moraxella catarrhalis

<400> SEQUENCE: 29

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
                20                  25                  30

Glu Gln Phe Phe Pro Asn Ile Phe Ser Asn His Ala Pro Val Lys Gln
            35                  40                  45

His Tyr His Asn Val Val Gly Asp Thr Ser Ile Val Glu Asn Leu
        50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Pro Leu Asp Glu Asn
            100                 105                 110

Gly Lys Pro Val Tyr Lys Val Asp Tyr Lys Leu Asp Gly Gln Glu Pro
        115                 120                 125

Arg Arg Val Tyr Ser Val Thr Thr Lys Ile Ala Thr Gln Asp Asp Val
130                 135                 140

Asp Asn Ser Pro Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile Tyr Glu Leu Ala Gln Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly His Leu Ile Asp Gln Lys Ala Asp Leu Thr Lys
225                 230                 235                 240

Asp Ile Lys Thr Leu Glu Ser Asn Val Glu Glu Gly Leu Leu Glu Leu
                245                 250                 255
```

```
Ser Gly His Leu Ile Asp Gln Lys Ala Asp Ile Ala Lys Asn Gln Ala
            260                 265                 270

Asp Ile Ala Gln Asn Gln Ala Asn Ile Gln Asp Leu Ala Ala Tyr Asn
        275                 280                 285

Glu Leu Gln Asp Ala Tyr Ala Lys Gln Gln Thr Glu Ala Ile Asp Ala
    290                 295                 300

Leu Asn Lys Ala Ser Ser Glu Asn Thr Gln Asn Ile Glu Asp Leu Ala
305                 310                 315                 320

Ala Tyr Asn Glu Leu Gln Asp Ala Tyr Ala Lys Gln Gln Thr Glu Ala
                325                 330                 335

Ile Asp Ala Leu Asn Lys Ala Ser Ser Glu Asn Thr Gln Asn Ile Ala
            340                 345                 350

Lys Asn Gln Ala Asp Ile Ala Asn Asn Ile Asn Asn Ile Tyr Glu Leu
        355                 360                 365

Ala Gln Gln Gln Asp Gln His Ser Ser Asp Ile Lys Thr Leu Ala Lys
    370                 375                 380

Ala Ser Ala Ala Asn Thr Asp Arg Ile Ala Lys Asn Lys Ala Asp Ala
385                 390                 395                 400

Asp Ala Ser Phe Glu Thr Leu Thr Lys Asn Gln Asn Thr Leu Ile Glu
                405                 410                 415

Lys Asp Lys Glu His Asp Lys Leu Ile Thr Ala Asn Lys Thr Ala Ile
            420                 425                 430

Asp Ala Asn Lys Ala Ser Ala Asp Thr Lys Phe Ala Ala Thr Ala Asp
        435                 440                 445

Ala Ile Thr Lys Asn Gly Asn Ala Ile Thr Lys Asn Ala Lys Ser Ile
    450                 455                 460

Thr Asp Leu Gly Thr Lys Val Asp Ala Phe Asp Gly Arg Val Thr Ala
465                 470                 475                 480

Leu Asp Thr Lys Val Asn Ala Phe Asp Gly Arg Ile Thr Ala Leu Asp
                485                 490                 495

Ser Lys Val Glu Asn Gly Met Ala Ala Gln Ala Ala Leu Ser Gly Leu
            500                 505                 510

Phe Gln Pro Tyr Ser Val Gly Lys Phe Asn Ala Thr Ala Ala Leu Gly
        515                 520                 525

Gly Tyr Gly Ser Lys Ser Ala Val Ala Ile Gly Ala Gly Tyr Arg Val
    530                 535                 540

Asn Pro Asn Leu Ala Phe Lys Ala Gly Ala Ala Ile Asn Thr Ser Gly
545                 550                 555                 560

Asn Lys Lys Gly Ser Tyr Asn Ile Gly Val Asn Tyr Glu Phe
                565                 570

<210> SEQ ID NO 30
<211> LENGTH: 678
<212> TYPE: PRT
<213> ORGANISM: Moraxella catarrhalis

<400> SEQUENCE: 30

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
                20                  25                  30

Pro Gln Thr Glu Thr Phe Phe Pro Asn Ile Phe Phe Asn Glu Asn His
            35                  40                  45

Asp Ala Leu Asp Asp Val Tyr His Asn Met Ile Leu Gly Asp Thr Ala
        50                  55                  60
```

```
Ile Thr Gln Asp Asn Gln Tyr Lys Phe Tyr Ala Asp Ala Ile Ser Glu
 65                  70                  75                  80

Val Pro Asp Ser Leu Leu Phe Asn Lys Ile Leu His Asp Gln Gln Leu
                 85                  90                  95

Asn Gly Phe Lys Glu Gly Asp Thr Ile Ile Pro Leu Asp Glu Asn Gly
            100                 105                 110

Lys Pro Val Tyr Lys Leu Asp Glu Lys Val Glu Asn Gly Val Lys Lys
            115                 120                 125

Ser Val Tyr Ser Val Thr Thr Lys Thr Ala Thr Arg Ala Asp Val Glu
130                 135                 140

Gln Ser Ala Tyr Ser Arg Gly Ile Gln Gly Asp Ile Asp Asp Leu Tyr
145                 150                 155                 160

Glu Ala Asn Lys Glu Asn Val Asn Arg Leu Ile Glu His Gly Asp Lys
            165                 170                 175

Ile Phe Ala Asn Glu Glu Ser Val Gln Tyr Leu Asn Lys Glu Val Gln
            180                 185                 190

Asn Asn Ile Glu Asn Ile His Glu Leu Ala Gln Gln Asp Gln His
            195                 200                 205

Ser Ser Asp Ile Lys Thr Leu Lys Lys Asn Val Glu Glu Gly Leu Leu
210                 215                 220

Glu Leu Ser Gly His Leu Ile Asp Gln Lys Ala Asp Leu Thr Lys Asp
225                 230                 235                 240

Ile Lys Thr Leu Glu Ser Asn Val Glu Glu Gly Leu Leu Asp Leu Ser
            245                 250                 255

Gly Arg Leu Leu Asp Gln Lys Ala Asp Ile Ala Gln Asn Gln Ala Asn
            260                 265                 270

Ile Gln Asp Leu Ala Ala Tyr Asn Glu Leu Gln Asp Ala Tyr Ala Lys
            275                 280                 285

Gln Gln Thr Glu Ala Ile Asp Ala Leu Asn Lys Ala Ser Ser Glu Asn
            290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
            325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
            355                 360                 365

Lys Ala Ser Ser Glu Asn Thr Gln Asn Ile Glu Asp Leu Ala Ala Tyr
            370                 375                 380

Asn Glu Leu Gln Asp Ala Tyr Ala Lys Gln Gln Thr Glu Ala Ile Asp
385                 390                 395                 400

Ala Leu Asn Lys Ala Ser Ser Glu Asn Thr Gln Asn Ile Glu Asp Leu
            405                 410                 415

Ala Ala Tyr Asn Glu Leu Gln Asp Ala Tyr Ala Lys Gln Gln Thr Glu
            420                 425                 430

Ala Ile Asp Ala Leu Asn Lys Ala Ser Ser Glu Asn Thr Gln Asn Ile
            435                 440                 445

Ala Lys Asn Gln Ala Asp Ile Ala Asn Asn Ile Asn Asn Ile Tyr Glu
            450                 455                 460

Leu Ala Gln Gln Gln Asp Gln His Ser Ser Asp Ile Lys Thr Leu Ala
465                 470                 475                 480
```

Lys Ala Ser Ala Ala Asn Thr Asp Arg Ile Ala Lys Asn Lys Ala Asp
                485                 490                 495

Ala Asp Ala Ser Phe Glu Thr Leu Thr Lys Asn Gln Asn Thr Leu Ile
            500                 505                 510

Glu Lys Asp Lys Glu His Asp Lys Leu Ile Thr Ala Asn Lys Thr Ala
            515                 520                 525

Ile Asp Ala Asn Lys Ala Ser Ala Asp Thr Lys Phe Ala Ala Thr Ala
            530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Ala Phe Asp Gly Arg Val Thr
                565                 570                 575

Ala Leu Asp Thr Lys Val Asn Ala Leu Asp Thr Lys Val Asn Ala Phe
            580                 585                 590

Asp Gly Arg Ile Thr Ala Leu Asp Ser Lys Val Glu Asn Gly Met Ala
            595                 600                 605

Ala Gln Ala Ala Leu Ser Gly Leu Phe Gln Pro Tyr Ser Val Gly Lys
            610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
            660                 665                 670

Gly Val Asn Tyr Glu Phe
            675

<210> SEQ ID NO 31
<211> LENGTH: 678
<212> TYPE: PRT
<213> ORGANISM: Moraxella catarrhalis

<400> SEQUENCE: 31

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Phe Asn Glu
            35                  40                  45

Asn His Asp Ala Leu Asp Val Tyr His Asn Met Ile Leu Gly Asp
50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
                85                  90                  95

Gln Leu Asn Gly Phe Lys Glu Gly Asp Thr Ile Ile Pro Leu Asp Glu
            100                 105                 110

Asn Gly Lys Pro Val Tyr Lys Leu Asp Glu Lys Val Glu Asn Gly Val
            115                 120                 125

Lys Lys Ser Val Tyr Ser Val Thr Thr Lys Thr Ala Arg Ala Asp
            130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

```
Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Thr Leu
305                 310                 315                 320

Glu Asn Asn Ile Glu Glu Gly Leu Leu Glu Leu Ser Gly His Leu Ile
                325                 330                 335

Asp Gln Lys Ala Asp Leu Thr Lys Asp Ile Lys Ala Leu Glu Ser Asn
            340                 345                 350

Val Glu Glu Gly Leu Leu Asp Leu Ser Gly Arg Leu Leu Asp Gln Lys
        355                 360                 365

Ala Asp Ile Ala Gln Asn Gln Ala Asn Ile Gln Asp Leu Ala Ala Tyr
    370                 375                 380

Asn Glu Leu Gln Asp Gln Tyr Ala Gln Lys Gln Thr Glu Ala Ile Asp
385                 390                 395                 400

Ala Leu Asn Lys Ala Ser Ser Glu Asn Thr Gln Asn Ile Glu Asp Leu
                405                 410                 415

Ala Ala Tyr Asn Glu Leu Gln Asp Ala Tyr Ala Lys Gln Gln Thr Glu
            420                 425                 430

Ala Ile Asp Ala Leu Asn Lys Ala Ser Ser Glu Asn Thr Gln Asn Ile
        435                 440                 445

Ala Lys Asn Gln Ala Asp Ile Ala Asn Asn Ile Asn Asn Ile Tyr Glu
    450                 455                 460

Leu Ala Gln Gln Gln Asp Gln His Ser Ser Asp Ile Lys Thr Leu Ala
465                 470                 475                 480

Lys Ala Ser Ala Ala Asn Thr Asp Arg Ile Ala Lys Asn Lys Ala Asp
                485                 490                 495

Ala Asp Ala Ser Phe Glu Thr Leu Thr Lys Asn Gln Asn Thr Leu Ile
            500                 505                 510

Glu Lys Asp Lys Glu His Asp Lys Leu Ile Thr Ala Asn Lys Thr Ala
        515                 520                 525

Ile Asp Thr Asn Lys Ala Ser Ala Asp Thr Lys Phe Ala Ala Thr Ala
    530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Gly Phe Asp Gly Arg Val Thr
                565                 570                 575

Ala Leu Asp Thr Lys Val Asn Ala Leu Asp Thr Lys Val Asn Ala Phe
            580                 585                 590
```

-continued

```
Asp Gly Arg Ile Thr Ala Leu Asp Ser Lys Val Glu Asn Gly Met Ala
            595                 600                 605

Ala Gln Ala Ala Leu Ser Gly Leu Phe Gln Pro Tyr Ser Val Gly Lys
610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
            645                 650                 655

Gly Ala Ala Ile Asn Thr Ser Gly Asn Lys Lys Gly Ser Tyr Asn Ile
            660                 665                 670

Gly Val Asn Tyr Glu Phe
            675

<210> SEQ ID NO 32
<211> LENGTH: 587
<212> TYPE: PRT
<213> ORGANISM: Moraxella catarrhalis

<400> SEQUENCE: 32

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Leu Val
            20                  25                  30

Glu Arg Phe Phe Pro Asn Ile Phe Leu Asp Lys Pro Leu Ala Lys Gln
        35                  40                  45

His Tyr His Asn Val Val Val Gly Asp Thr Ser Ile Val Ser Asp Leu
    50                  55                  60

Gln Ser Asn Ser Asp Gln Leu Lys Phe Tyr Ser Asp Asp Glu Gly Leu
65                  70                  75                  80

Val Pro Asp Ser Leu Leu Phe Asn Lys Met Leu His Glu Gln Leu Leu
                85                  90                  95

Asn Gly Phe Lys Glu Gly Asp Thr Ile Ile Pro Leu Asp Glu Asn Gly
            100                 105                 110

Lys Pro Val Tyr Lys Val Asp Tyr Lys Leu Asp Gly Lys Glu Pro Arg
        115                 120                 125

Lys Val Tyr Ser Val Thr Thr Lys Ile Ala Thr Ala Glu Asp Val Ala
130                 135                 140

Thr Ser Ser Tyr Ala Asn Gly Ile Gln Lys Asp Ile Asp Asp Leu Tyr
145                 150                 155                 160

Asp Phe Asp His Gln Val Thr Glu Arg Leu Thr Gln His Gly Lys Thr
                165                 170                 175

Ile Tyr Arg Asn Gly Glu Arg Ile Leu Ala Asn Glu Glu Ser Val Gln
            180                 185                 190

Tyr Leu Asn Lys Glu Val Gln Asn Asn Ile Glu His Ile Tyr Glu Leu
        195                 200                 205

Ala Gln Gln Gln Asp Gln His Ser Ser Asp Ile Lys Thr Leu Glu Ser
    210                 215                 220

Asn Val Glu Lys Gly Leu Leu Glu Leu Ser Gly His Leu Ile Asp Gln
225                 230                 235                 240

Lys Ala Asp Leu Thr Lys Asp Ile Lys Thr Leu Glu Asn Asn Val Glu
                245                 250                 255

Glu Gly Leu Leu Asp Leu Ser Gly Arg Leu Ile Asp Gln Lys Ala Asp
            260                 265                 270

Ile Ala Gln Asn Gln Ala Asn Ile Gln Asp Leu Ala Ala Tyr Asn Glu
        275                 280                 285
```

Leu Gln Asp Gln Tyr Ala Gln Lys Gln Thr Glu Ala Ile Asp Ala Leu
            290                 295                 300

Asn Lys Ala Ser Ser Glu Asn Thr Gln Asn Ile Glu Asp Leu Ala Ala
305                 310                 315                 320

Tyr Asn Glu Leu Gln Asp Ala Tyr Ala Lys Gln Gln Thr Glu Ala Ile
            325                 330                 335

Asp Ala Leu Asn Lys Ala Ser Ser Glu Asn Thr Gln Asn Ile Ala Lys
            340                 345                 350

Asn Gln Ala Asp Ile Ala Asn Asn Ile Asn Asn Ile Tyr Glu Leu Ala
            355                 360                 365

Gln Gln Gln Asp Gln His Ser Ser Asp Ile Lys Thr Leu Ala Lys Ala
            370                 375                 380

Ser Ala Ala Asn Thr Asp Arg Ile Ala Lys Asn Lys Ala Asp Ala Asp
385                 390                 395                 400

Ala Ser Phe Glu Thr Leu Thr Lys Asn Gln Asn Thr Leu Ile Glu Lys
            405                 410                 415

Asp Lys Glu His Asp Lys Leu Ile Thr Ala Asn Lys Thr Ala Ile Asp
            420                 425                 430

Thr Asn Lys Ala Ser Ala Asp Thr Lys Phe Ala Ala Thr Ala Asp Ala
            435                 440                 445

Ile Thr Lys Asn Gly Asn Ala Ile Thr Lys Asn Ala Lys Ser Ile Thr
450                 455                 460

Asp Leu Gly Thr Lys Val Asp Gly Phe Asp Ser Arg Val Thr Ala Leu
465                 470                 475                 480

Asp Thr Lys Val Asn Ala Leu Asp Thr Lys Val Asn Ala Leu Asp Thr
            485                 490                 495

Lys Val Asn Ala Phe Asp Gly Arg Ile Thr Ala Leu Asp Ser Lys Val
            500                 505                 510

Glu Asn Gly Met Ala Ala Gln Ala Ala Leu Ser Gly Leu Phe Gln Pro
            515                 520                 525

Tyr Ser Val Gly Lys Phe Asn Ala Thr Ala Ala Leu Gly Gly Tyr Gly
            530                 535                 540

Ser Lys Ser Ala Val Ala Ile Gly Ala Gly Tyr Arg Val Asn Pro Asn
545                 550                 555                 560

Leu Ala Phe Lys Ala Gly Ala Ala Ile Asn Thr Ser Gly Asn Lys Lys
            565                 570                 575

Gly Ser Tyr Asn Ile Gly Val Asn Tyr Glu Phe
            580                 585

<210> SEQ ID NO 33
<211> LENGTH: 678
<212> TYPE: PRT
<213> ORGANISM: Moraxella catarrhalis

<400> SEQUENCE: 33

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Asn Glu
            35                  40                  45

Asn His Asp Ala Leu Asp Val Tyr His Asn Met Ile Leu Gly Asp
50                  55                  60

Thr Ala Ile Thr Gln Asp Asn Gln Tyr Lys Phe Tyr Ala Asp Ala Ile

```
                65                  70                  75                  80
Ser Glu Val Pro Asp Ser Leu Leu Phe Asn Lys Ile Leu His Asp Gln
                    85                  90                  95

Gln Leu Asn Gly Phe Lys Glu Gly Asp Thr Ile Ile Pro Leu Asp Glu
                100                 105                 110

Asn Gly Lys Pro Val Tyr Lys Leu Asp Glu Lys Val Glu Asn Gly Val
                115                 120                 125

Lys Lys Ser Val Tyr Ser Val Thr Thr Lys Thr Ala Thr Arg Ala Asp
130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
                180                 185                 190

Val Gln Asn Asn Ile Glu Asn Ile His Glu Leu Ala Gln Gln Gln Asp
                195                 200                 205

Gln His Ser Ser Asp Ile Lys Thr Leu Lys Lys Asn Val Glu Lys Asp
        210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
                260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
        290                 295                 300

His Leu Ile Asp Gln Lys Ala Asp Leu Thr Lys Asp Ile Lys Thr Leu
305                 310                 315                 320

Glu Asn Asn Ile Glu Glu Gly Leu Leu Glu Leu Ser Gly His Leu Ile
                325                 330                 335

Asp Gln Lys Ala Asp Leu Thr Lys Asp Ile Lys Ala Leu Glu Ser Asn
                340                 345                 350

Val Glu Glu Gly Leu Leu Asp Leu Ser Gly Arg Leu Leu Asp Gln Lys
        355                 360                 365

Ala Asp Ile Ala Gln Asn Gln Ala Asn Ile Gln Asp Leu Ala Ala Tyr
        370                 375                 380

Asn Glu Leu Gln Asp Gln Tyr Ala Gln Lys Gln Thr Glu Ala Ile Asp
385                 390                 395                 400

Ala Leu Asn Lys Ala Ser Ser Glu Asn Thr Gln Asn Ile Glu Asp Leu
                405                 410                 415

Ala Ala Tyr Asn Glu Leu Gln Asp Ala Tyr Ala Lys Gln Gln Thr Glu
                420                 425                 430

Ala Ile Asp Ala Leu Asn Lys Ala Ser Ser Glu Asn Thr Gln Asn Ile
        435                 440                 445

Ala Lys Asn Gln Ala Asp Ile Ala Asn Asn Ile Asn Asn Ile Tyr Glu
        450                 455                 460

Leu Ala Gln Gln Gln Asp Gln His Ser Ser Asp Ile Lys Thr Leu Ala
465                 470                 475                 480

Lys Ala Ser Ala Ala Asn Thr Asp Arg Ile Ala Lys Asn Lys Ala Asp
        485                 490                 495
```

```
Ala Asp Ala Ser Phe Glu Thr Leu Thr Lys Asn Gln Asn Thr Leu Ile
            500                 505                 510

Glu Lys Asp Lys Glu His Asp Lys Leu Ile Thr Ala Asn Lys Thr Ala
        515                 520                 525

Ile Asp Thr Asn Lys Ala Ser Ala Asp Thr Lys Phe Ala Ala Thr Ala
    530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Gly Phe Asp Gly Arg Val Thr
                565                 570                 575

Ala Leu Asp Thr Lys Val Asn Ala Leu Asp Thr Lys Val Asn Ala Phe
            580                 585                 590

Asp Gly Arg Ile Thr Ala Leu Asp Ser Lys Val Glu Asn Gly Met Ala
        595                 600                 605

Ala Gln Ala Ala Leu Ser Gly Leu Phe Gln Pro Tyr Ser Val Gly Lys
    610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
            660                 665                 670

Gly Val Asn Tyr Glu Phe
            675

<210> SEQ ID NO 34
<211> LENGTH: 616
<212> TYPE: PRT
<213> ORGANISM: Moraxella catarrhalis

<400> SEQUENCE: 34

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Val Arg
            20                  25                  30

Asp Lys Ser Leu Glu Asp Ile Glu Ala Leu Leu Gly Lys Ile Asp Ile
        35                  40                  45

Ser Lys Leu Glu Lys Glu Lys Lys Gln Gln Thr Glu Leu Gln Lys Tyr
    50                  55                  60

Leu Leu Leu Ser Gln Tyr Ala Asn Val Leu Thr Met Glu Glu Leu Asn
65                  70                  75                  80

Lys Asn Val Glu Lys Asn Thr Asn Ser Ile Glu Ala Leu Gly Tyr Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu His
        115                 120                 125

Asp Arg Leu Ile Ala Gln Asn Ala Asp Ile Lys Thr Leu Glu Asn
    130                 135                 140

Asn Val Val Glu Glu Leu Phe Asn Leu Ser Asp Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
```

```
            180                 185                 190
Glu Glu Val Asn Lys Thr Leu Glu Lys Leu Ile Thr Asn Ser Val Lys
            195                 200                 205
Asn Thr Asp Asn Ile Asp Lys Asn Lys Ala Asp Ile Gln Ala Leu Glu
            210                 215                 220
Asn Asn Val Glu Glu Gly Leu Leu Glu Leu Ser Gly His Leu Ile Asp
225                 230                 235                 240
Gln Lys Ala Asp Leu Thr Lys Asp Ile Lys Ala Leu Glu Ser Asn Val
                245                 250                 255
Glu Glu Gly Leu Leu Asp Leu Ser Gly Arg Leu Leu Asp Gln Lys Ala
            260                 265                 270
Asp Ile Ala Lys Asn Gln Ala Asp Ile Ala Gln Asn Gln Thr Asp Ile
            275                 280                 285
Gln Asp Leu Ala Ala Tyr Asn Glu Leu Gln Asp Gln Tyr Ala Gln Lys
            290                 295                 300
Gln Thr Glu Ala Ile Asp Ala Leu Asn Lys Ala Ser Ser Glu Asn Thr
305                 310                 315                 320
Gln Asn Ile Glu Asp Leu Ala Ala Tyr Asn Glu Leu Gln Asp Ala Tyr
                325                 330                 335
Ala Lys Gln Gln Thr Glu Ala Ile Asp Ala Leu Asn Lys Ala Ser Ser
            340                 345                 350
Glu Asn Thr Gln Asn Ile Glu Asp Leu Ala Ala Tyr Asn Glu Leu Gln
            355                 360                 365
Asp Ala Tyr Ala Lys Gln Gln Thr Glu Ala Ile Asp Ala Leu Asn Lys
            370                 375                 380
Ala Ser Ser Glu Asn Thr Gln Asn Ile Ala Lys Asn Gln Ala Asp Ile
385                 390                 395                 400
Ala Asn Asn Ile Asn Asn Ile Tyr Glu Leu Ala Gln Gln Gln Asp Gln
                405                 410                 415
His Ser Ser Asp Ile Lys Thr Leu Ala Lys Val Ser Ala Ala Asn Thr
            420                 425                 430
Asp Arg Ile Ala Lys Asn Lys Ala Asp Ala Asp Ala Ser Phe Glu Thr
            435                 440                 445
Leu Thr Lys Asn Gln Asn Thr Leu Ile Glu Lys Asp Lys Glu His Asp
            450                 455                 460
Lys Leu Ile Thr Ala Asn Lys Thr Ala Ile Asp Ala Asn Lys Ala Ser
465                 470                 475                 480
Ala Asp Thr Lys Phe Ala Ala Thr Ala Asp Ala Ile Thr Lys Asn Gly
                485                 490                 495
Asn Ala Ile Thr Lys Asn Ala Lys Ser Ile Thr Asp Leu Gly Thr Lys
            500                 505                 510
Val Asp Gly Phe Asp Ser Arg Val Thr Ala Leu Asp Thr Lys Val Asn
            515                 520                 525
Ala Phe Asp Gly Arg Ile Thr Ala Leu Asp Ser Lys Val Glu Asn Gly
            530                 535                 540
Met Ala Ala Gln Ala Ala Leu Ser Gly Leu Phe Gln Pro Tyr Ser Val
545                 550                 555                 560
Gly Lys Phe Asn Ala Thr Ala Ala Leu Gly Tyr Gly Ser Lys Ser
                565                 570                 575
Ala Val Ala Ile Gly Ala Gly Tyr Arg Val Asn Pro Asn Leu Ala Phe
            580                 585                 590
Lys Ala Gly Ala Ala Ile Asn Thr Ser Gly Asn Lys Lys Gly Ser Tyr
            595                 600                 605
```

Asn Ile Gly Val Asn Tyr Glu Phe
            610                 615

<210> SEQ ID NO 35
<211> LENGTH: 676
<212> TYPE: PRT
<213> ORGANISM: Moraxella catarrhalis

<400> SEQUENCE: 35

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asn Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Gln Leu Asn Gly Phe
                85                  90                  95

Lys Glu Gly Asp Thr Ile Ile Pro Leu Asp Glu Asn Gly Lys Pro Val
            100                 105                 110

Tyr Lys Leu Asp Glu Ile Thr Glu Asn Gly Val Lys Arg Lys Val Tyr
        115                 120                 125

Ser Val Thr Thr Lys Thr Ala Thr Arg Glu Asp Val Glu Gln Ser Ala
    130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Gln Asp Gln His Ser Ser Asp
        195                 200                 205

Ile Lys Thr Leu Lys Lys Asn Val Glu Glu Gly Leu Leu Glu Leu Ser
    210                 215                 220

Gly His Leu Ile Asp Gln Lys Ala Asp Leu Thr Lys Asp Ile Lys Ala
225                 230                 235                 240

Leu Glu Ser Asn Val Glu Glu Gly Leu Leu Asp Leu Ser Gly His Leu
                245                 250                 255

Ile Asp Gln Lys Ala Asp Leu Thr Lys Asp Ile Lys Ala Leu Glu Ser
            260                 265                 270

Asn Val Glu Glu Gly Leu Leu Asp Leu Ser Gly Arg Leu Leu Asp Gln
        275                 280                 285

Lys Ala Asp Ile Ala Lys Asn Gln Ala Asp Ile Ala Gln Asn Gln Thr
    290                 295                 300

Asp Ile Gln Asp Leu Ala Ala Tyr Asn Glu Leu Gln Asp Gln Tyr Ala
305                 310                 315                 320

Gln Lys Gln Thr Glu Ala Ile Asp Ala Leu Asn Lys Ala Ser Ser Glu
                325                 330                 335

Asn Thr Gln Asn Ile Glu Asp Leu Ala Ala Tyr Asn Glu Leu Gln Asp
            340                 345                 350

Gln Tyr Ala Gln Lys Gln Thr Glu Ala Ile Asp Ala Leu Asn Lys Ala 355                 360                 365
Ser Ser Glu Asn Thr Gln Asn Ile Glu Asp Leu Ala Ala Tyr Asn Glu
    370                 375                 380

Leu Gln Asp Gln Tyr Ala Gln Lys Gln Thr Glu Ala Ile Asp Ala Leu
385                 390                 395                 400

Asn Lys Ala Ser Ser Glu Asn Thr Gln Asn Ile Glu Asp Leu Ala Ala
                405                 410                 415

Tyr Asn Glu Leu Gln Asp Gln Tyr Ala Gln Lys Gln Thr Glu Ala Ile
            420                 425                 430

Asp Ala Leu Asn Lys Ala Ser Ser Glu Asn Thr Gln Asn Ile Ala Lys
        435                 440                 445

Asn Gln Ala Asp Ile Ala Asn Ile Asn Asn Ile Tyr Glu Leu Ala
    450                 455                 460

Gln Gln Gln Asp Gln His Ser Ser Asp Ile Lys Thr Leu Ala Lys Ala
465                 470                 475                 480

Ser Ala Ala Asn Thr Asp Arg Ile Ala Lys Asn Lys Ala Asp Ala Asp
                485                 490                 495

Ala Ser Phe Glu Thr Leu Thr Lys Asn Gln Asn Thr Leu Ile Glu Lys
            500                 505                 510

Asp Lys Glu His Asp Lys Leu Ile Thr Ala Asn Lys Thr Ala Ile Asp
        515                 520                 525

Ala Asn Lys Ala Ser Ala Asp Thr Lys Phe Ala Ala Thr Ala Asp Ala
    530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
                565                 570                 575

Asp Thr Lys Val Asn Ala Leu Asp Thr Lys Val Asn Ala Phe Asp Gly
            580                 585                 590

Arg Ile Thr Ala Leu Asp Ser Lys Val Glu Asn Gly Met Ala Ala Gln
        595                 600                 605

Ala Ala Leu Ser Gly Leu Phe Gln Pro Tyr Ser Val Gly Lys Phe Asn
    610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
                645                 650                 655

Ala Ile Asn Thr Ser Gly Asn Lys Lys Gly Ser Tyr Asn Ile Gly Val
            660                 665                 670

Asn Tyr Glu Phe
            675

<210> SEQ ID NO 36
<211> LENGTH: 629
<212> TYPE: PRT
<213> ORGANISM: Moraxella catarrhalis

<400> SEQUENCE: 36

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Asn Gly
                20                  25                  30

Thr Ser Thr Lys Leu Lys Asn Leu Lys Glu Tyr Ala Gln Tyr Leu Asp
        35                  40                  45

```
Asn Tyr Ala Gln Tyr Leu Asp Asp Ile Asp Asp Leu Asp Lys Glu
    50                  55                  60
Val Gly Glu Leu Ser Gln Asn Ile Ala Lys Asn Gln Ala Asn Ile Lys
65                  70                  75                  80
Asp Leu Asn Lys Lys Leu Ser Arg Asp Ile Asp Ser Leu Arg Glu Asp
                85                  90                  95
Val Tyr Asp Asn Gln Tyr Glu Ile Val Asn Asn Gln Ala Asp Ile Glu
                100                 105                 110
Lys Asn Gln Asp Asp Ile Lys Glu Leu Glu Asn Asn Val Gly Lys Glu
            115                 120                 125
Leu Leu Asn Leu Ser Gly Arg Leu Leu Asp Gln Lys Ala Asp Ile Asp
        130                 135                 140
Asn Asn Ile Asn Asn Ile Tyr Glu Leu Ala Gln Gln Gln Asp Gln His
145                 150                 155                 160
Ser Ser Asp Ile Lys Thr Leu Lys Lys Asn Val Glu Glu Gly Leu Leu
                165                 170                 175
Glu Leu Ser Gly His Leu Ile Asp Gln Lys Ser Asp Ile Ala Gln Asn
                180                 185                 190
Gln Thr Asp Ile Gln Asp Leu Ala Thr Tyr Asn Glu Leu Gln Asp Gln
            195                 200                 205
Tyr Ala Gln Lys Gln Thr Glu Ala Ile Asp Ala Leu Asn Lys Ala Ser
        210                 215                 220
Ser Glu Asn Thr Gln Asn Ile Glu Asp Leu Ala Ala Tyr Asn Glu Leu
225                 230                 235                 240
Gln Asp Ala Tyr Ala Lys Gln Thr Glu Ala Ile Asp Ala Leu Asn
                245                 250                 255
Lys Ala Ser Ser Glu Asn Thr Gln Asn Ile Gln Asp Leu Ala Ala Tyr
            260                 265                 270
Asn Glu Leu Gln Asp Ala Tyr Ala Lys Gln Thr Glu Ala Ile Asp
        275                 280                 285
Ala Leu Asn Lys Ala Ser Ser Glu Asn Thr Gln Asn Ile Glu Asp Leu
        290                 295                 300
Ala Ala Tyr Asn Glu Leu Gln Asp Ala Tyr Ala Lys Gln Gln Thr Glu
305                 310                 315                 320
Ala Ile Asp Ala Leu Asn Lys Ala Ser Ser Glu Asn Thr Gln Asn Ile
            325                 330                 335
Glu Asp Leu Ala Ala Tyr Asn Glu Leu Gln Asp Ala Tyr Ala Lys Gln
            340                 345                 350
Gln Thr Glu Ala Ile Asp Ala Leu Asn Lys Ala Ser Ser Glu Asn Thr
        355                 360                 365
Gln Asn Ile Glu Asp Leu Ala Ala Tyr Asn Glu Leu Gln Asp Ala Tyr
        370                 375                 380
Ala Lys Gln Gln Thr Glu Ala Ile Asp Ala Leu Asn Lys Ala Ser Ser
385                 390                 395                 400
Glu Asn Thr Gln Asn Ile Ala Lys Asn Gln Ala Asp Ile Ala Asn Asn
                405                 410                 415
Ile Asn Asn Ile Tyr Glu Leu Ala Gln Gln Gln Asp Gln His Ser Ser
                420                 425                 430
Asp Ile Lys Thr Leu Ala Lys Ala Ser Ala Ala Asn Thr Asp Arg Ile
            435                 440                 445
Ala Lys Asn Lys Ala Asp Ala Asp Ala Ser Phe Glu Thr Leu Thr Lys
450                 455                 460
Asn Gln Asn Thr Leu Ile Glu Lys Asp Lys Glu His Asp Lys Leu Ile
```

-continued

```
            465                 470                 475                 480
        Thr Ala Asn Lys Thr Ala Ile Asp Ala Asn Lys Ala Ser Ala Asp Thr
                        485                 490                 495

Lys Phe Ala Ala Thr Ala Asp Ala Ile Thr Lys Asn Gly Asn Ala Ile
                        500                 505                 510

Thr Lys Asn Ala Lys Ser Ile Thr Asp Leu Gly Thr Lys Val Asp Ala
                        515                 520                 525

Phe Asp Gly Arg Val Thr Ala Leu Asp Thr Lys Val Asn Ala Phe Asp
                        530                 535                 540

Gly Arg Ile Thr Ala Leu Asp Ser Lys Val Glu Asn Gly Met Ala Ala
        545                 550                 555                 560

Gln Ala Ala Leu Ser Gly Leu Phe Gln Pro Tyr Ser Val Gly Lys Phe
                        565                 570                 575

Asn Ala Thr Ala Ala Leu Gly Gly Tyr Gly Ser Lys Ser Ala Val Ala
                        580                 585                 590

Ile Gly Ala Gly Tyr Arg Val Asn Pro Asn Leu Ala Phe Lys Ala Gly
                        595                 600                 605

Ala Ala Ile Asn Thr Ser Gly Asn Lys Lys Gly Ser Tyr Asn Ile Gly
                        610                 615                 620

Val Asn Tyr Glu Phe
        625

<210> SEQ ID NO 37
<211> LENGTH: 683
<212> TYPE: PRT
<213> ORGANISM: Moraxella catarrhalis

<400> SEQUENCE: 37

Met Lys Thr Met Lys Leu Leu Pro Leu Lys Ile Ala Val Thr Ser Ala
        1               5                   10                  15

Met Ile Val Gly Leu Gly Met Ala Ser Thr Ala Asn Ala Gln Gln Gln
                        20                  25                  30

Arg Ser Pro Lys Thr Glu Thr Phe Leu Pro Asn Ile Phe Phe Asn Glu
                        35                  40                  45

Tyr Ala Asp Asp Leu Asp Thr Leu Tyr His Asn Met Ile Leu Gly Asp
                        50                  55                  60

Thr Ala Ile Thr His Asp Asp Gln Tyr Lys Phe Tyr Ala Asp Asp Ala
        65                  70                  75                  80

Thr Glu Val Pro Asp Ser Leu Phe Phe Asn Lys Ile Leu His Asp Gln
                        85                  90                  95

Leu Leu Tyr Gly Phe Lys Glu Gly Asp Lys Ile Ile Pro Leu Asp Glu
                        100                 105                 110

Asn Gly Lys Pro Val Tyr Lys Leu Asp Lys Arg Leu Asp Asn Gly Val
                        115                 120                 125

Gln Lys Thr Val Tyr Ser Val Thr Thr Lys Thr Ala Thr Ala Asp Asp
        130                 135                 140

Val Asn Ser Ala Tyr Ser Arg Gly Ile Gln Gly Asp Ile Asp Asp Leu
        145                 150                 155                 160

Tyr Glu Ala Asn Lys Glu Asn Val Asn Arg Leu Ile Glu His Gly Asp
                        165                 170                 175

Lys Ile Phe Ala Asn Glu Glu Ser Val Gln Tyr Leu Asn Lys Glu Val
                        180                 185                 190

Gln Asn Asn Ile Glu Asn Ile His Glu Leu Ala Gln Gln Gln Asp Gln
                        195                 200                 205
```

-continued

His Ser Ser Asp Ile Lys Thr Leu Lys Lys Asn Val Glu Glu Gly Leu
210                 215                 220

Leu Glu Leu Ser Gly His Leu Ile Asp Gln Lys Thr Asp Ile Ala Gln
225                 230                 235                 240

Asn Gln Thr Asp Ile Gln Asp Leu Ala Thr Tyr Asn Glu Leu Gln Asp
            245                 250                 255

Gln Tyr Ala Gln Lys Gln Thr Glu Ala Ile Asp Ala Leu Asn Lys Ala
            260                 265                 270

Ser Ser Glu Asn Thr Gln Asn Ile Ala Lys Asn Ser Asn Arg Ile Lys
        275                 280                 285

Ala Leu Glu Asn Asn Ile Glu Glu Gly Leu Leu Glu Leu Ser Gly His
290                 295                 300

Leu Ile Asp Gln Lys Ala Asp Leu Thr Lys Asp Ile Lys Ala Leu Glu
305                 310                 315                 320

Ser Asn Val Glu Glu Gly Leu Leu Asp Leu Ser Gly Arg Leu Ile Asp
                325                 330                 335

Gln Lys Ala Asp Ile Ala Gln Asn Gln Ala Asn Ile Gln Asp Leu Ala
            340                 345                 350

Ala Tyr Asn Glu Leu Gln Asp Ala Tyr Ala Lys Gln Gln Thr Glu Ala
            355                 360                 365

Ile Asp Ala Leu Asn Lys Ala Ser Ser Glu Asn Thr Gln Asn Ile Glu
370                 375                 380

Asp Leu Ala Ala Tyr Asn Glu Leu Gln Asp Ala Tyr Ala Lys Gln Gln
385                 390                 395                 400

Thr Glu Ala Ile Asp Ala Leu Asn Lys Ala Ser Ser Glu Asn Thr Gln
                405                 410                 415

Asn Ile Glu Asp Leu Ala Ala Tyr Asn Glu Leu Gln Asp Ala Tyr Ala
            420                 425                 430

Lys Gln Gln Thr Glu Ala Ile Asp Ala Leu Asn Lys Ala Ser Ser Glu
            435                 440                 445

Asn Thr Gln Asn Ile Ala Lys Asn Gln Ala Asp Ile Ala Asn Asn Ile
450                 455                 460

Asn Asn Ile Tyr Glu Leu Ala Gln Gln Gln Asp Gln His Ser Ser Asp
465                 470                 475                 480

Ile Lys Thr Leu Ala Lys Ala Ser Ala Ala Asn Thr Asp Arg Ile Ala
                485                 490                 495

Lys Asn Lys Ala Asp Ala Asp Ala Ser Phe Glu Thr Leu Thr Lys Asn
            500                 505                 510

Gln Asn Thr Leu Ile Glu Lys Asp Lys Glu His Asp Lys Leu Ile Thr
            515                 520                 525

Ala Asn Lys Thr Ala Ile Asp Ala Asn Lys Ala Ser Ala Asp Thr Lys
530                 535                 540

Phe Ala Ala Thr Ala Asp Ala Ile Thr Lys Asn Gly Asn Ala Ile Thr
545                 550                 555                 560

Lys Asn Ala Lys Ser Ile Thr Asp Leu Gly Thr Lys Val Asp Gly Phe
                565                 570                 575

Asp Gly Arg Val Thr Ala Leu Asp Thr Lys Val Asn Ala Leu Asp Thr
            580                 585                 590

Lys Val Asn Ala Phe Asp Gly Arg Ile Thr Ala Leu Asp Ser Lys Val
            595                 600                 605

Glu Asn Gly Met Ala Ala Gln Ala Ala Leu Ser Gly Leu Phe Gln Pro
610                 615                 620

Tyr Ser Val Gly Lys Phe Asn Ala Thr Ala Ala Leu Gly Gly Tyr Gly

```
                         625                 630                 635                 640
        Ser Lys Ser Ala Val Ala Ile Gly Ala Gly Tyr Arg Val Asn Pro Asn
                            645                 650                 655

Leu Ala Phe Lys Ala Gly Ala Ala Ile Asn Thr Ser Gly Asn Lys Lys
                            660                 665                 670

Gly Ser Tyr Asn Ile Gly Val Asn Tyr Glu Phe
                            675                 680

<210> SEQ ID NO 38
<211> LENGTH: 700
<212> TYPE: PRT
<213> ORGANISM: Moraxella catarrhalis

<400> SEQUENCE: 38

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Ala Gln
            20                  25                  30

Ser Asn Arg Ser Leu Asp Gln Val Gln Ala Leu Leu Arg Gly Ile Asp
        35                  40                  45

Glu Thr Lys Ile Lys Lys Glu Ile Gln Gln Ser Gln Gln Pro Glu Leu
50                  55                  60

Asn Lys Tyr Leu Thr Phe Asn Gln Leu Ala Asn Ala Leu Asn Ile Glu
65                  70                  75                  80

Glu Leu Asn Asn Asn Val Gln Lys Asn Thr Gln Arg Leu Asp Ser Ala
                85                  90                  95

Ala Thr Leu Tyr Gly Asp Leu Ser Lys Thr Val Pro Lys Ser Ile Lys
            100                 105                 110

Glu Asn Lys Glu Ser Ile Lys Glu Asn Lys Glu Ser Ile Lys Glu Asn
        115                 120                 125

Lys Glu Ser Ile Lys Glu Asn Lys Glu Ser Ile Lys Glu Asn Lys Glu
130                 135                 140

Ser Ile Lys Glu Asn Lys Glu Ser Ile Thr Thr Leu Thr Arg Lys Ser
145                 150                 155                 160

Phe Gln Asn Gln Val Asp Ile Val Arg Asn Asn Ala Ser Ile Glu Asp
                165                 170                 175

Leu Tyr Ala Tyr Gly Gln Glu Val Ala Lys Ser Ile Gly Glu Ile His
            180                 185                 190

Ala Tyr Thr Glu Glu Val Asn Lys Thr Leu Glu Asn Leu Ile Thr Asn
        195                 200                 205

Ser Val Glu Asn Thr Asn Asn Ile Thr Lys Asn Lys Ala Asp Ile Gln
210                 215                 220

Ala Leu Glu Asn Val Val Glu Glu Leu Phe Asn Leu Ser Gly Arg
225                 230                 235                 240

Leu Ile Asp Gln Lys Ala Asp Ile Asp Asn Asn Ile Asn Asn Ile Tyr
                245                 250                 255

Glu Leu Ala Gln Gln Asp Gln His Ser Ser Asp Ile Lys Thr Leu
            260                 265                 270

Lys Lys Asn Val Glu Glu Gly Leu Leu Glu Leu Ser Gly His Leu Ile
        275                 280                 285

Asp Gln Lys Ala Asp Leu Thr Lys Asp Ile Lys Thr Leu Glu Ser Asn
290                 295                 300

Val Glu Glu Gly Leu Leu Asp Leu Ser Gly Arg Leu Leu Asp Gln Lys
305                 310                 315                 320
```

Ala Asp Ile Ala Gln Asn Gln Ala Asn Ile Gln Asp Leu Ala Ala Tyr
              325                 330                 335

Asn Glu Leu Gln Asp Ala Tyr Ala Lys Gln Gln Thr Glu Ala Ile Asp
          340                 345                 350

Ala Leu Asn Lys Ala Ser Ser Glu Asn Thr Gln Asn Ile Glu Asp Leu
          355                 360                 365

Ala Ala Tyr Asn Glu Leu Gln Asp Ala Tyr Ala Lys Gln Gln Thr Glu
          370                 375                 380

Ala Ile Asp Ala Leu Asn Lys Ala Ser Ser Glu Asn Thr Gln Asn Ile
385                 390                 395                 400

Glu Asp Leu Ala Ala Tyr Asn Glu Leu Gln Asp Ala Tyr Ala Lys Gln
              405                 410                 415

Gln Thr Glu Ala Ile Asp Ala Leu Asn Lys Ala Ser Ser Glu Asn Thr
          420                 425                 430

Gln Asn Ile Glu Asp Leu Ala Ala Tyr Asn Glu Leu Gln Asp Ala Tyr
          435                 440                 445

Ala Lys Gln Gln Thr Glu Ala Ile Asp Ala Leu Asn Lys Ala Ser Ser
          450                 455                 460

Glu Asn Thr Gln Asn Ile Ala Lys Asn Gln Ala Asp Ile Ala Asn Asn
465                 470                 475                 480

Ile Asn Asn Ile Tyr Glu Leu Ala Gln Gln Asp Gln His Ser Ser
              485                 490                 495

Asp Ile Lys Thr Leu Ala Lys Ala Ser Ala Ala Asn Thr Asp Arg Ile
              500                 505                 510

Ala Lys Asn Lys Ala Asp Ala Asp Ala Ser Phe Glu Thr Leu Thr Lys
          515                 520                 525

Asn Gln Asn Thr Leu Ile Glu Lys Asp Lys Glu His Asp Lys Leu Ile
          530                 535                 540

Thr Ala Asn Lys Thr Val Ile Asp Ala Asn Lys Ala Ser Ala Asp Thr
545                 550                 555                 560

Lys Phe Ala Ala Thr Ala Asp Ala Ile Thr Lys Asn Gly Asn Ala Ile
              565                 570                 575

Thr Lys Asn Ala Lys Ser Ile Thr Asp Leu Gly Thr Lys Val Asp Gly
          580                 585                 590

Phe Asp Gly Arg Val Thr Ala Leu Asp Thr Lys Val Asn Ala Leu Asp
          595                 600                 605

Thr Lys Val Asn Ala Phe Asp Gly Arg Ile Thr Ala Leu Asp Ser Lys
          610                 615                 620

Val Glu Asn Gly Met Ala Ala Gln Ala Ala Leu Ser Gly Leu Phe Gln
625                 630                 635                 640

Pro Tyr Ser Val Gly Lys Phe Asn Ala Thr Ala Ala Leu Gly Gly Tyr
              645                 650                 655

Gly Ser Lys Ser Ala Val Ala Ile Gly Ala Gly Tyr Arg Val Asn Pro
          660                 665                 670

Asn Leu Ala Phe Lys Ala Gly Ala Ala Ile Asn Thr Ser Gly Asn Lys
          675                 680                 685

Lys Gly Ser Tyr Asn Ile Gly Val Asn Tyr Glu Phe
          690                 695                 700

<210> SEQ ID NO 39
<211> LENGTH: 676
<212> TYPE: PRT
<213> ORGANISM: Moraxella catarrhalis

<400> SEQUENCE: 39

```
Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Ile Glu Thr Thr
            35                  40                  45

Asp Pro Leu Tyr His Gly Met Ile Leu Gly Asn Thr Ala Ile Thr Gln
50                      55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Gln Leu Asn Gly Phe
                85                  90                  95

Lys Glu Gly Asp Thr Ile Ile Pro Leu Asp Glu Asn Gly Lys Pro Val
                100                 105                 110

Tyr Lys Leu Asp Glu Ile Thr Glu Asn Gly Val Lys Arg Lys Val Tyr
        115                 120                 125

Ser Val Thr Thr Lys Thr Ala Thr Arg Glu Asp Val Glu Gln Ser Ala
        130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
                180                 185                 190

Glu Asn Ile His Glu Leu Ala Gln Gln Gln Asp Gln His Ser Ser Asp
            195                 200                 205

Ile Lys Thr Leu Lys Lys Asn Val Glu Glu Gly Leu Leu Glu Leu Ser
        210                 215                 220

Gly His Leu Ile Asp Gln Lys Ala Asp Leu Thr Lys Asp Ile Lys Thr
225                 230                 235                 240

Leu Glu Asn Asn Val Glu Glu Gly Leu Leu Glu Leu Ser Gly His Leu
                245                 250                 255

Ile Asp Gln Lys Ala Asp Leu Thr Lys Asp Ile Lys Ala Leu Glu Ser
                260                 265                 270

Asn Val Glu Glu Gly Leu Leu Asp Leu Ser Gly Arg Leu Leu Asp Gln
            275                 280                 285

Lys Ala Asp Ile Ala Lys Asn Gln Ala Asp Ile Ala Gln Asn Gln Thr
        290                 295                 300

Asp Ile Gln Asp Leu Ala Ala Tyr Asn Glu Leu Gln Asp Gln Tyr Ala
305                 310                 315                 320

Gln Lys Gln Thr Glu Ala Ile Asp Ala Leu Asn Lys Ala Ser Ser Glu
            325                 330                 335

Asn Thr Gln Asn Ile Glu Asp Leu Ala Ala Tyr Asn Glu Leu Gln Asp
            340                 345                 350

Gln Tyr Ala Gln Lys Gln Thr Glu Ala Ile Asp Ala Leu Asn Lys Ala
        355                 360                 365

Ser Ser Glu Asn Thr Gln Asn Ile Glu Asp Leu Ala Ala Tyr Asn Glu
    370                 375                 380

Leu Gln Asp Gln Tyr Ala Gln Lys Gln Thr Glu Ala Ile Asp Ala Leu
385                 390                 395                 400

Asn Lys Ala Ser Ser Glu Asn Thr Gln Asn Ile Glu Asp Leu Ala Ala
                405                 410                 415
```

Tyr Asn Glu Leu Gln Asp Gln Tyr Ala Gln Lys Gln Thr Glu Ala Ile
                420                 425                 430

Asp Ala Leu Asn Lys Ala Ser Ser Glu Asn Thr Gln Asn Ile Ala Lys
            435                 440                 445

Asn Gln Ala Asp Ile Ala Asn Asn Ile Asn Asn Ile Tyr Glu Leu Ala
        450                 455                 460

Gln Gln Gln Asp Gln His Ser Ser Asp Ile Lys Thr Leu Ala Lys Ala
465                 470                 475                 480

Ser Ala Ala Asn Thr Asp Arg Ile Ala Lys Asn Lys Ala Asp Ala Asp
                485                 490                 495

Ala Ser Phe Glu Thr Leu Thr Lys Asn Gln Asn Thr Leu Ile Glu Lys
            500                 505                 510

Asp Lys Glu His Asp Lys Leu Ile Thr Ala Asn Lys Thr Ala Ile Asp
        515                 520                 525

Ala Asn Lys Ala Ser Ala Asp Thr Lys Phe Ala Ala Thr Ala Asp Ala
530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
                565                 570                 575

Asp Thr Lys Val Asn Ala Leu Asp Thr Lys Val Asn Ala Phe Asp Gly
            580                 585                 590

Arg Ile Thr Ala Leu Asp Ser Lys Val Glu Asn Gly Met Ala Ala Gln
        595                 600                 605

Ala Ala Leu Ser Gly Leu Phe Gln Pro Tyr Ser Val Gly Lys Phe Asn
610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
                645                 650                 655

Ala Ile Asn Thr Ser Gly Asn Lys Lys Gly Ser Tyr Asn Ile Gly Val
            660                 665                 670

Asn Tyr Glu Phe
        675

<210> SEQ ID NO 40
<211> LENGTH: 678
<212> TYPE: PRT
<213> ORGANISM: Moraxella catarrhalis

<400> SEQUENCE: 40

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
                20                  25                  30

Glu Gln Phe Phe Pro Asn Ile Phe Ser Asn His Ala Pro Val Lys Gln
            35                  40                  45

His Tyr His Asn Val Val Gly Asp Thr Ser Ile Val Glu Asn Leu
        50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Ile Pro Leu Asp Glu Asn
            100                 105                 110

-continued

```
Gly Lys Pro Val Tyr Lys Val Asp Tyr Lys Leu Asp Gly Gln Glu Pro
            115                 120                 125

Arg Arg Val Tyr Ser Val Thr Thr Lys Ile Ala Thr Gln Asp Asp Val
        130                 135                 140

Asp Asn Ser Pro Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
                    180                 185                 190

Gln Asn Asn Ile Glu Asn Ile Tyr Glu Leu Ala Gln Gln Gln Asp Gln
                195                 200                 205

His Ser Ser Asp Ile Lys Thr Leu Lys Lys Asn Val Glu Glu Gly Leu
        210                 215                 220

Leu Glu Leu Ser Gly Arg Leu Ile Asp Gln Lys Ala Asp Ile Ala Gln
225                 230                 235                 240

Asn Gln Ala Asn Ile Gln Asp Leu Ala Ala Tyr Asn Glu Leu Gln Asp
                    245                 250                 255

Gln Tyr Ala Gln Lys Gln Thr Glu Ala Ile Asp Ala Leu Asn Lys Ala
                260                 265                 270

Ser Ser Glu Asn Thr Gln Asn Ile Glu Asp Leu Ala Ala Tyr Asn Glu
                275                 280                 285

Leu Gln Asp Ala Tyr Ala Lys Gln Gln Thr Glu Ala Ile Asp Ala Leu
        290                 295                 300

Asn Lys Ala Ser Ser Glu Asn Thr Gln Asn Ile Glu Asp Leu Ala Ala
305                 310                 315                 320

Tyr Asn Glu Leu Gln Asp Ala Tyr Ala Lys Gln Gln Thr Glu Ala Ile
                    325                 330                 335

Asp Ala Leu Asn Lys Ala Ser Ser Glu Asn Thr Gln Asn Ile Glu Asp
                340                 345                 350

Leu Ala Ala Tyr Asn Glu Leu Gln Asp Ala Tyr Ala Lys Gln Gln Thr
            355                 360                 365

Glu Ala Ile Asp Ala Leu Asn Lys Ala Ser Ser Glu Asn Thr Gln Asn
        370                 375                 380

Ile Glu Asp Leu Ala Ala Tyr Asn Glu Leu Gln Asp Ala Tyr Ala Lys
385                 390                 395                 400

Gln Gln Thr Glu Ala Ile Asp Ala Leu Asn Lys Ala Ser Ser Glu Asn
                    405                 410                 415

Thr Gln Asn Ile Glu Asp Leu Ala Ala Tyr Asn Glu Leu Gln Asp Ala
                420                 425                 430

Tyr Ala Lys Gln Gln Thr Glu Ala Ile Asp Ala Leu Asn Lys Ala Ser
            435                 440                 445

Ser Glu Asn Thr Gln Asn Ile Ala Lys Asn Gln Ala Asp Ile Ala Asn
        450                 455                 460

Asn Ile Asn Asn Ile Tyr Glu Leu Ala Gln Gln Gln Asp Gln His Ser
465                 470                 475                 480

Ser Asp Ile Lys Thr Leu Ala Lys Val Ser Ala Ala Asn Thr Asp Arg
                    485                 490                 495

Ile Ala Lys Asn Lys Ala Asp Ala Asp Ala Ser Phe Glu Thr Leu Thr
                500                 505                 510

Lys Asn Gln Asn Thr Leu Ile Glu Lys Asp Lys Glu His Asp Lys Leu
            515                 520                 525
```

```
Ile Thr Ala Asn Lys Thr Ala Ile Asp Ala Asn Lys Ala Ser Ala Asp
            530                 535                 540

Thr Lys Phe Ala Ala Thr Ala Asp Ala Ile Thr Lys Asn Gly Asn Ala
545                 550                 555                 560

Ile Thr Lys Asn Ala Lys Ser Ile Thr Asp Leu Gly Thr Lys Val Asp
                565                 570                 575

Gly Phe Asp Gly Arg Val Thr Ala Leu Asp Thr Lys Val Asn Ala Phe
            580                 585                 590

Asp Gly Arg Ile Thr Ala Leu Asp Ser Lys Val Glu Asn Gly Met Ala
            595                 600                 605

Ala Gln Ala Ala Leu Ser Gly Leu Phe Gln Pro Tyr Ser Val Gly Lys
610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
            660                 665                 670

Gly Val Asn Tyr Glu Phe
            675
```

<210> SEQ ID NO 41
<211> LENGTH: 613
<212> TYPE: PRT
<213> ORGANISM: Moraxella catarrhalis

<400> SEQUENCE: 41

```
Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
                20                  25                  30

Asp Arg Ser Leu Glu Asp Ile Gln Asp Ser Ile Ser Lys Leu Val Gln
            35                  40                  45

Asp Asp Ile Asn Thr Leu Lys Gln Asp Gln Gln Lys Met Asn Lys Tyr
    50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu Glu His
        115                 120                 125

Asp Arg Leu Ile Ala Gln Asn Gln Ala Asp Ile Gln Thr Leu Glu Asn
    130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Asn Leu Ile Thr Asn Ser Val Lys
        195                 200                 205

Asn Thr Asp Asn Ile Asp Lys Asn Lys Ala Asp Ile Asp Asn Asn Ile
    210                 215                 220
```

```
Asn His Ile Tyr Glu Leu Ala Gln Gln Asp Gln His Ser Ser Asp
225                 230                 235                 240

Ile Lys Thr Leu Lys Asn Val Glu Glu Gly Leu Leu Glu Leu Ser
                245                 250                 255

Gly His Leu Ile Asp Gln Lys Ala Asp Leu Thr Lys Asp Ile Lys Ala
            260                 265                 270

Leu Glu Ser Asn Val Glu Glu Gly Leu Leu Asp Leu Ser Gly Arg Leu
        275                 280                 285

Leu Asp Gln Lys Ala Asp Leu Thr Lys Asp Ile Lys Ala Leu Glu Ser
290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
                340                 345                 350

Asp Ala Leu Asn Lys Ala Ser Ser Glu Asn Thr Gln Asn Ile Glu Asp
                355                 360                 365

Leu Ala Ala Tyr Asn Glu Leu Gln Asp Ala Tyr Ala Lys Gln Gln Thr
            370                 375                 380

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Asn Ile Asn Asn Ile Tyr
                405                 410                 415

Glu Leu Ala Gln Gln Asp Gln His Ser Ser Asp Ile Lys Thr Leu
                420                 425                 430

Ala Lys Ala Ser Ala Ala Asn Thr Asn Arg Ile Ala Thr Ala Glu Leu
                435                 440                 445

Gly Ile Ala Glu Asn Lys Lys Asp Ala Gln Ile Ala Lys Ala Gln Ala
            450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
                500                 505                 510

Phe Asp Gly Arg Val Thr Ala Leu Asp Thr Lys Val Asn Ala Phe Asp
            515                 520                 525

Gly Arg Ile Thr Ala Leu Asp Ser Lys Val Glu Asn Gly Met Ala Ala
            530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
            595                 600                 605

Val Asn Tyr Glu Phe
        610

<210> SEQ ID NO 42
<211> LENGTH: 589
```

<212> TYPE: PRT
<213> ORGANISM: Moraxella catarrhalis

<400> SEQUENCE: 42

```
Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Asn Lys Asp Ile Thr Leu Glu Asp Val Leu Lys Ser Ile Glu Glu Ile
        35                  40                  45

Asp Pro Tyr Glu Leu Arg Asp Tyr Ile Glu Tyr Pro Thr Ala Ile Glu
    50                  55                  60

Arg Phe Leu Leu Leu Ser Gln Tyr Gly Asn Thr Leu Thr Leu Glu Glu
65                  70                  75                  80

Phe Asp Asn Asp Ile Glu Leu Leu Asp Gln Asp Val Glu Asp Leu Glu
                85                  90                  95

Glu Ser Val Thr Glu Leu Ala Lys Asn Gln Asn Ser Leu Ile Glu Gln
            100                 105                 110

Gly Glu Ala Ile Lys Glu Asp Leu Gln Gly Leu Ala Asp Phe Val Glu
        115                 120                 125

Arg Gln Glu Asp Lys Ile Leu Gln Asn Glu Thr Ser Ile Lys Lys Asn
    130                 135                 140

Thr Gln Arg Asn Leu Val Asn Gly Phe Glu Ile Glu Lys Asn Lys Asp
145                 150                 155                 160

Ala Ile Ala Lys Asn Asn Glu Ser Ile Glu Asp Leu Tyr Asp Phe Gly
                165                 170                 175

His Glu Val Ala Lys Ser Ile Gly Glu Ile His Ala His Asn Glu Ala
            180                 185                 190

Gln Asn Glu Thr Leu Lys Asp Leu Ile Thr Asn Ser Val Lys Asn Thr
        195                 200                 205

Asp Asn Ile Thr Lys Asn Lys Ala Asp Ile Gln Ala Leu Glu Ser Asn
    210                 215                 220

Val Glu Lys Gly Leu Leu Glu Leu Ser Gly His Leu Ile Asp Gln Lys
225                 230                 235                 240

Ala Asp Ile Asp Asn Asn Ile Asn Asn Ile His Glu Leu Ala Gln Gln
                245                 250                 255

Gln Asp Gln His Ser Ser Asp Ile Lys Thr Leu Lys Lys Asn Val Glu
            260                 265                 270

Glu Gly Leu Leu Glu Leu Ser Gly His Leu Ile Asp Gln Lys Ser Asp
        275                 280                 285

Ile Ala Gln Asn Gln Ala Asn Ile Gln Asp Leu Ala Thr Tyr Asn Glu
    290                 295                 300

Leu Gln Asp Gln Tyr Ala Gln Lys Gln Thr Glu Ala Ile Asp Ala Leu
305                 310                 315                 320

Asn Lys Ala Ser Ser Glu Asn Thr Gln Asn Ile Glu Asp Leu Ala Ala
                325                 330                 335

Tyr Asn Glu Leu Gln Asp Ala Tyr Ala Lys Gln Gln Thr Glu Ala Ile
            340                 345                 350

Asp Ala Leu Asn Lys Ala Ser Ser Glu Asn Thr Gln Asn Ile Ala Lys
        355                 360                 365

Asn Gln Ala Asp Ile Ala Asn Asn Ile Asn Asn Ile Tyr Glu Leu Ala
    370                 375                 380

Gln Gln Gln Asp Gln His Ser Ser Asp Ile Lys Thr Leu Ala Lys Ala
385                 390                 395                 400
```

```
Ser Ala Ala Asn Thr Asp Arg Ile Ala Lys Asn Lys Ala Asp Ala Asp
            405                 410                 415

Ala Ser Phe Glu Thr Leu Thr Lys Asn Gln Asn Thr Leu Ile Glu Lys
        420                 425                 430

Asp Lys Glu His Asp Lys Leu Ile Thr Ala Asn Lys Thr Ala Ile Asp
            435                 440                 445

Ala Asn Lys Ala Ser Ala Asp Thr Lys Phe Ala Ala Thr Ala Asp Ala
        450                 455                 460

Ile Thr Lys Asn Gly Asn Ala Ile Thr Lys Asn Ala Lys Ser Ile Thr
465                 470                 475                 480

Asp Leu Gly Thr Lys Val Asp Gly Phe Asp Ser Arg Val Thr Ala Leu
            485                 490                 495

Asp Thr Lys Val Asn Ala Phe Asp Gly Arg Ile Thr Ala Leu Asp Ser
        500                 505                 510

Lys Val Glu Asn Gly Met Ala Ala Gln Ala Ala Leu Ser Gly Leu Phe
    515                 520                 525

Gln Pro Tyr Ser Val Gly Lys Phe Asn Ala Thr Ala Ala Leu Gly Gly
        530                 535                 540

Tyr Gly Ser Lys Ser Ala Val Ala Ile Gly Ala Gly Tyr Arg Val Asn
545                 550                 555                 560

Pro Asn Leu Ala Phe Lys Ala Gly Ala Ala Ile Asn Thr Ser Gly Asn
            565                 570                 575

Lys Lys Gly Ser Tyr Asn Ile Gly Val Asn Tyr Glu Phe
        580                 585

<210> SEQ ID NO 43
<211> LENGTH: 684
<212> TYPE: PRT
<213> ORGANISM: Moraxella catarrhalis

<400> SEQUENCE: 43

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
            85                  90                  95

Gln Leu Leu His Gly Phe Lys Glu Gly Asp Thr Ile Ile Pro Leu Asp
        100                 105                 110

Glu Asn Gly Lys Pro Val Tyr Lys Leu Asp Ser Ile Val Glu Gln Gly
    115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
            165                 170                 175

Asp Lys Ile Phe Ala Asn Glu Glu Ser Val Gln Tyr Leu Asn Arg Glu
```

```
              180                 185                 190
Val Gln Asn Asn Ile Glu Asn Ile His Glu Leu Ala Gln Gln Gln Asp
            195                 200                 205
Gln His Ser Ser Asp Ile Lys Thr Leu Lys Lys Asn Val Glu Lys Asp
        210                 215                 220
Leu Leu Asp Leu Ser Gly Arg Leu Ile Ala Gln Lys Glu Asp Ile Ala
225                 230                 235                 240
Gln Asn Gln Thr Asp Ile Gln Asp Leu Ala Thr Tyr Asn Glu Leu Gln
                245                 250                 255
Asp Gln Tyr Ala Gln Lys Gln Thr Glu Ala Ile Asp Ala Leu Asn Lys
            260                 265                 270
Ala Ser Ser Glu Asn Thr Gln Asn Ile Ala Lys Asn Ser Asn His Ile
        275                 280                 285
Lys Thr Leu Glu Asn Asn Ile Glu Glu Gly Leu Leu Glu Leu Ser Gly
    290                 295                 300
His Leu Ile Asp Gln Lys Ala Asp Leu Thr Lys Asp Ile Lys Ala Leu
305                 310                 315                 320
Glu Ser Asn Val Glu Glu Gly Leu Leu Asp Leu Ser Gly Arg Leu Ile
                325                 330                 335
Asp Gln Lys Ala Asp Ile Ala Gln Asn Gln Ala Asn Ile Gln Asp Leu
            340                 345                 350
Ala Ala Tyr Asn Glu Leu Gln Asp Ala Tyr Ala Lys Gln Gln Thr Glu
        355                 360                 365
Ala Ile Asp Ala Leu Asn Lys Ala Ser Ser Glu Asn Thr Gln Asn Ile
    370                 375                 380
Glu Asp Leu Ala Ala Tyr Asn Glu Leu Gln Asp Ala Tyr Ala Lys Gln
385                 390                 395                 400
Gln Thr Glu Ala Ile Asp Ala Leu Asn Lys Ala Ser Ser Glu Asn Thr
                405                 410                 415
Gln Asn Ile Glu Asp Leu Ala Ala Tyr Asn Glu Leu Gln Asp Ala Tyr
            420                 425                 430
Ala Lys Gln Gln Thr Glu Ala Ile Asp Ala Leu Asn Lys Ala Ser Ser
        435                 440                 445
Glu Asn Thr Gln Asn Ile Ala Lys Asn Gln Ala Asp Ile Ala Asn Asn
    450                 455                 460
Ile Asn Asn Ile Tyr Glu Leu Ala Gln Gln Gln Asp Gln His Ser Ser
465                 470                 475                 480
Asp Ile Lys Thr Leu Ala Lys Ala Ser Ala Asn Thr Asp Arg Ile
                485                 490                 495
Ala Lys Asn Lys Ala Asp Ala Asp Ala Ser Phe Glu Thr Leu Thr Lys
        500                 505                 510
Asn Gln Asn Thr Leu Ile Glu Lys Asp Lys Glu His Asp Lys Leu Ile
    515                 520                 525
Thr Ala Asn Lys Thr Ala Ile Asp Ala Asn Lys Ala Ser Ala Asp Thr
530                 535                 540
Lys Phe Ala Ala Thr Ala Asp Ala Ile Thr Lys Asn Gly Asn Ala Ile
545                 550                 555                 560
Thr Lys Asn Ala Lys Ser Ile Thr Asp Leu Gly Thr Lys Val Asp Gly
                565                 570                 575
Phe Asp Gly Arg Val Thr Ala Leu Asp Thr Lys Val Asn Ala Leu Asp
            580                 585                 590
Thr Lys Val Asn Ala Phe Asp Gly Arg Ile Thr Ala Leu Asp Ser Lys
        595                 600                 605
```

Val Glu Asn Gly Met Ala Ala Gln Ala Ala Leu Ser Gly Leu Phe Gln
610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
            645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
            675                 680

<210> SEQ ID NO 44
<211> LENGTH: 650
<212> TYPE: PRT
<213> ORGANISM: Moraxella catarrhalis

<400> SEQUENCE: 44

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
            20                  25                  30

Gln Lys Thr Lys Thr Glu Val Phe Leu Pro Asn Leu Phe Tyr Asn Asp
            35                  40                  45

Tyr Ile Glu Glu Thr Asp Leu Leu Tyr His Asn Met Ile Leu Gly Asp
    50                  55                  60

Thr Ala Leu Val Asp Arg Gln Asn Tyr Ser Asn Ser Gln Leu Lys
65                  70                  75                  80

Phe Tyr Ser Asn Asp Glu Glu Ser Val Pro Asp Ser Leu Leu Phe Ser
                85                  90                  95

Lys Met Leu Asn Asn Gln Leu Asn Gly Phe Lys Ala Gly Asp Ile
            100                 105                 110

Ile Ile Pro Val Asp Ala Asn Gly Gln Val Ile Tyr Gln Lys Asp Thr
            115                 120                 125

Arg Val Glu Gly Gly Lys Thr Arg Thr Val Leu Ser Val Thr Thr Lys
130                 135                 140

Ile Ala Thr Gln Gln Asp Val Asp Ser Ala Tyr Ser Arg Gly Ile Gln
145                 150                 155                 160

Gly Lys Val Asn Asp Leu Asp Asp Glu Met Asn Phe Leu Asn His Asp
                165                 170                 175

Ile Thr Ser Leu Tyr Asp Val Thr Ala Asn Gln Gln Asp Ile Lys
            180                 185                 190

Gly Leu Lys Lys Gly Val Lys Asp Leu Lys Lys Gly Val Lys Gly Leu
            195                 200                 205

Asn Lys Glu Leu Lys Glu Leu Asp Lys Glu Val Gly Val Leu Ser Arg
210                 215                 220

Asp Ile Gly Ser Leu Asn Asp Val Ala Gln Asn Glu Ser Ile
225                 230                 235                 240

Glu Asp Leu Tyr Asp Phe Ser Gln Glu Val Ala Asp Ser Ile Gly Glu
                245                 250                 255

Ile His Ala His Asn Lys Ala Gln Asn Glu Thr Leu Gln Asp Leu Ile
            260                 265                 270

Thr Asn Ser Val Glu Asn Thr Asn Asn Ile Thr Lys Asn Lys Ala Asp
            275                 280                 285

Ile Gln Ala Leu Glu Asn Asn Val Val Glu Glu Leu Phe Asn Leu Ser

```
            290                 295                 300
Gly Arg Leu Ile Asp Gln Lys Ala Asp Leu Thr Lys Asp Ile Lys Thr
305                 310                 315                 320

Leu Glu Ser Asn Val Glu Gly Leu Leu Glu Leu Ser Gly His Leu
                325                 330                 335

Ile Asp Gln Lys Ala Asp Ile Ala Lys Asn Gln Ala Asp Ile Ala Gln
                340                 345                 350

Asn Gln Ala Asn Ile Gln Asp Leu Ala Ala Tyr Asn Glu Leu Gln Asp
                355                 360                 365

Ala Tyr Ala Lys Gln Gln Thr Glu Ala Ile Asp Ala Leu Asn Lys Ala
                370                 375                 380

Ser Ser Glu Asn Thr Gln Asn Ile Glu Asp Leu Ala Ala Tyr Asn Glu
385                 390                 395                 400

Leu Gln Asp Ala Tyr Ala Lys Gln Gln Thr Glu Ala Ile Asp Ala Leu
                405                 410                 415

Asn Lys Ala Ser Ser Glu Asn Thr Gln Asn Ile Ala Lys Asn Gln Ala
                420                 425                 430

Asp Ile Ala Asn Asn Ile Asn Asn Ile Tyr Glu Leu Ala Gln Gln Gln
                435                 440                 445

Asp Gln His Ser Ser Asp Ile Lys Thr Leu Ala Lys Ala Ser Ala Ala
                450                 455                 460

Asn Thr Asp Arg Ile Ala Lys Asn Lys Ala Asp Ala Asp Ala Ser Phe
465                 470                 475                 480

Glu Thr Leu Thr Lys Asn Gln Asn Thr Leu Ile Glu Lys Asp Lys Glu
                485                 490                 495

His Asp Lys Leu Ile Thr Ala Asn Lys Thr Ala Ile Asp Glu Asn Lys
                500                 505                 510

Ala Ser Ala Asp Thr Lys Phe Ala Ala Thr Ala Asp Ala Ile Thr Lys
                515                 520                 525

Asn Gly Asn Ala Ile Thr Lys Asn Ala Lys Ser Ile Thr Asp Leu Gly
                530                 535                 540

Thr Lys Val Asp Gly Phe Asp Gly Arg Val Thr Ala Leu Asp Thr Lys
545                 550                 555                 560

Val Asn Ala Phe Asp Gly Arg Ile Thr Ala Leu Asp Ser Lys Val Glu
                565                 570                 575

Asn Gly Met Ala Ala Gln Ala Ala Leu Ser Gly Leu Phe Gln Pro Tyr
                580                 585                 590

Ser Val Gly Lys Phe Asn Ala Thr Ala Ala Leu Gly Gly Tyr Gly Ser
                595                 600                 605

Lys Ser Ala Val Ala Ile Gly Ala Gly Tyr Arg Val Asn Pro Asn Leu
                610                 615                 620

Ala Phe Lys Ala Gly Ala Ala Ile Asn Thr Ser Gly Asn Lys Lys Gly
625                 630                 635                 640

Ser Tyr Asn Ile Gly Val Asn Tyr Glu Phe
                645                 650

<210> SEQ ID NO 45
<211> LENGTH: 616
<212> TYPE: PRT
<213> ORGANISM: Moraxella catarrhalis

<400> SEQUENCE: 45

Met Lys Thr Met Lys Leu Leu Pro Leu Lys Ile Ala Val Thr Ser Ala
1               5                   10                  15
```

```
Leu Ile Val Gly Leu Gly Ala Val Ser Thr Thr Asn Ala Gln Ala Gln
                20                  25                  30

Ser Arg Ser Leu Asp Gln Ile Gln Thr Lys Leu Ala Asp Leu Ala Gly
            35                  40                  45

Lys Ile Ala Ala Gly Lys Asn Gly Gly Gln Asn Asn Gln Asn Asn
50                  55                  60

Gln Asn Asp Ile Asn Lys Tyr Leu Phe Leu Ser Gln Tyr Ala Asn Ile
65                  70                  75                  80

Leu Thr Met Glu Glu Leu Asn Asn Asn Val Val Lys Asn Ser Ser Ser
                85                  90                  95

Ile Glu Thr Leu Glu Thr Asp Phe Gly Trp Leu Glu Asn Asp Val Ala
                100                 105                 110

Asp Leu Glu Asp Gly Val Glu Glu Leu Thr Lys Asn Gln Asn Thr Leu
            115                 120                 125

Ile Glu Lys Asp Glu Glu His Asp Arg Leu Ile Ala Gln Asn Gln Ala
            130                 135                 140

Asp Ile Gln Thr Leu Glu Asn Asn Val Val Glu Glu Leu Phe Asn Leu
145                 150                 155                 160

Ser Asp Arg Leu Ile Asp Gln Lys Ala Asp Ile Ala Lys Asn Gln Ala
                165                 170                 175

Asp Ile Ala Gln Asn Asn Glu Ser Ile Glu Glu Leu Tyr Asp Phe Asp
                180                 185                 190

Asn Glu Val Ala Glu Lys Ile Gly Glu Ile His Ala Tyr Thr Glu Glu
            195                 200                 205

Val Asn Lys Thr Leu Gln Asp Leu Ile Thr Asn Ser Val Lys Asn Thr
210                 215                 220

Asp Asn Ile Asp Lys Asn Lys Ala Asp Ile Asp Asn Asn Ile Asn His
225                 230                 235                 240

Ile Tyr Glu Leu Ala Gln Gln Asp Gln His Ser Ser Asp Ile Lys
                245                 250                 255

Thr Leu Lys Asn Asn Val Glu Glu Gly Leu Leu Glu Leu Ser Gly His
            260                 265                 270

Leu Ile Asp Gln Lys Ala Asp Leu Thr Lys Asp Ile Lys Thr Leu Glu
    275                 280                 285

Asn Asn Val Glu Glu Gly Leu Leu Asp Leu Ser Gly Arg Leu Ile Asp
290                 295                 300

Gln Lys Ala Asp Ile Ala Lys Asn Gln Ala Asp Ile Ala Gln Asn Gln
305                 310                 315                 320

Thr Asp Ile Gln Asp Leu Ala Ala Tyr Asn Glu Leu Gln Asp Gln Tyr
                325                 330                 335

Ala Gln Lys Gln Thr Glu Ala Ile Asp Ala Leu Asn Lys Ala Ser Ser
            340                 345                 350

Glu Asn Thr Gln Asn Ile Glu Asp Leu Ala Ala Tyr Asn Glu Leu Gln
            355                 360                 365

Asp Ala Tyr Ala Lys Gln Gln Thr Glu Ala Ile Asp Ala Leu Asn Lys
    370                 375                 380

Ala Ser Ser Glu Asn Thr Gln Asn Ile Ala Lys Asn Gln Ala Asp Ile
385                 390                 395                 400

Ala Asn Asn Ile Asn Ile Tyr Glu Leu Ala Gln Gln Asp Gln
                405                 410                 415

His Ser Ser Asp Ile Lys Thr Leu Ala Lys Ala Ser Ala Ala Asn Thr
            420                 425                 430

Asp Arg Ile Ala Lys Asn Lys Ala Asp Ala Asp Ala Ser Phe Glu Thr
```

```
                      435                 440                 445
Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Glu Asn Lys Ala Ser
465                 470                 475                 480

Ala Asp Thr Lys Phe Ala Thr Ala Asp Ala Ile Thr Lys Asn Gly
                485                 490                 495

Asn Ala Ile Thr Lys Asn Ala Lys Ser Ile Thr Asp Leu Gly Thr Lys
                500                 505                 510

Val Asp Gly Phe Asp Gly Arg Val Thr Ala Leu Asp Thr Lys Val Asn
            515                 520                 525

Ala Phe Asp Gly Arg Ile Thr Ala Leu Asp Ser Lys Val Glu Asn Gly
        530                 535                 540

Met Ala Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
    610                 615

<210> SEQ ID NO 46
<211> LENGTH: 668
<212> TYPE: PRT
<213> ORGANISM: Moraxella catarrhalis

<400> SEQUENCE: 46

Met Lys Thr Met Lys Leu Leu Pro Leu Lys Ile Ala Val Thr Ser Ala
1               5                   10                  15

Leu Ile Val Gly Leu Gly Thr Ala Ser Thr Ala Asn Ala Gln Val Ala
            20                  25                  30

Ser Pro Ala Asn Gln Lys Ile Gln Gln Lys Ile Lys Lys Val Arg Lys
        35                  40                  45

Glu Leu Arg Gln Asp Ile Lys Ser Leu Arg Asn Asp Ile Asp Ser Asn
    50                  55                  60

Thr Ala Asp Ile Gly Ser Leu Asn Asp Val Ala Asp Asn Gln Asp
65                  70                  75                  80

Asp Ile Leu Asp Asn Gln Ala Asp Ile Ala Lys Asn Gln Asp Ile
                85                  90                  95

Glu Lys Asn Gln Ala Asp Ile Lys Glu Leu Asp Lys Glu Val Gly Val
                100                 105                 110

Leu Ser Arg Glu Ile Gly Ser Leu Asn Asp Ile Ala Asp Asn Tyr
            115                 120                 125

Thr Asp Ile Ile Asp Asn Tyr Thr Asp Ile Ile Asp Asn Gln Ala Asn
        130                 135                 140

Ile Ala Lys Asn Gln Asp Ile Glu Lys Asn Gln Ala Asp Ile Lys
145                 150                 155                 160

Glu Leu Asp Lys Glu Val Gly Val Leu Ser Arg Glu Ile Gly Ser Leu
                165                 170                 175

Asn Asp Asp Val Ala Asp Asn Gln Asp Ile Ala Lys Asn Gln Ala
                180                 185                 190
```

```
Asp Ile Gln Thr Leu Glu Asn Asn Val Glu Glu Gly Leu Glu Leu
        195                 200                 205

Ser Gly His Leu Leu Asp Gln Lys Ala Asp Ile Asp Asn Asn Ile Asn
210                 215                 220

Asn Ile Tyr Glu Leu Ala Gln Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Glu
        275                 280                 285

Gln Thr Glu Ala Ile Asp Ala Leu Asn Lys Ala Ser Ser Glu Asn Thr
    290                 295                 300

Gln Asn Ile Ala Lys Asn Ser Asn Arg Ile Lys Ala Leu Glu Ser Asn
305                 310                 315                 320

Val Glu Glu Gly Leu Leu Glu Leu Ser Gly His Leu Ile Asp Gln Lys
                325                 330                 335

Ala Asp Leu Thr Lys Asp Ile Lys Ala Leu Glu Ser Asn Val Glu Glu
            340                 345                 350

Gly Leu Leu Glu Leu Ser Gly His Leu Ile Asp Gln Lys Ala Asp Ile
        355                 360                 365

Ala Gln Asn Gln Ala Asn Ile Gln Asp Leu Ala Ala Tyr Asn Glu Leu
    370                 375                 380

Gln Asp Gln Tyr Ala Gln Lys Gln Thr Glu Ala Ile Asp Ala Leu Asn
385                 390                 395                 400

Lys Ala Ser Ser Glu Asn Thr Gln Asn Ile Glu Asp Leu Ala Ala Tyr
                405                 410                 415

Asn Glu Leu Gln Asp Ala Tyr Ala Lys Gln Gln Thr Glu Ala Ile Asp
            420                 425                 430

Ala Leu Asn Lys Ala Ser Ser Glu Asn Thr Gln Asn Ile Ala Lys Asn
        435                 440                 445

Gln Ala Asp Ile Ala Asn Asn Ile Asn Asn Ile Tyr Glu Leu Ala Gln
    450                 455                 460

Gln Gln Asp Gln His Ser Ser Asp Ile Lys Thr Leu Ala Lys Ala Ser
465                 470                 475                 480

Ala Ala Asn Thr Asp Arg Ile Ala Lys Asn Lys Ala Asp Ala Asp Ala
                485                 490                 495

Ser Phe Glu Thr Leu Thr Lys Asn Gln Asn Thr Leu Ile Glu Lys Asp
            500                 505                 510

Lys Glu His Asp Lys Leu Ile Thr Ala Asn Lys Thr Ala Ile Asp Ala
        515                 520                 525

Asn Lys Val Ser Ala Asp Thr Lys Phe Ala Ala Thr Ala Asp Ala Ile
    530                 535                 540

Thr Lys Asn Gly Asn Ala Ile Thr Lys Asn Ala Lys Ser Ile Thr Asp
545                 550                 555                 560

Leu Gly Thr Lys Val Asp Ala Phe Asp Ser Arg Val Thr Ala Leu Asp
                565                 570                 575

Thr Lys Val Asn Ala Phe Asp Gly Arg Ile Thr Ala Leu Asp Ser Lys
            580                 585                 590

Val Glu Asn Gly Met Ala Ala Gln Ala Ala Leu Ser Gly Leu Phe Gln
        595                 600                 605

Pro Tyr Ser Val Gly Lys Phe Asn Ala Thr Ala Ala Leu Gly Gly Tyr
```

```
              610                 615                 620
Gly Ser Lys Ser Ala Val Ala Ile Gly Ala Gly Tyr Arg Val Asn Pro
625                 630                 635                 640

Asn Leu Ala Phe Lys Ala Gly Ala Ala Ile Asn Thr Ser Gly Asn Lys
                645                 650                 655

Lys Gly Ser Tyr Asn Ile Gly Val Asn Tyr Glu Phe
                660                 665

<210> SEQ ID NO 47
<211> LENGTH: 674
<212> TYPE: PRT
<213> ORGANISM: Moraxella catarrhalis

<400> SEQUENCE: 47

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
                20                  25                  30

Glu Gln Phe Phe Pro Asn Ile Phe Asn Glu Asn His Asp Glu Leu
            35                  40                  45

Asp Asp Ala Tyr His Asn Met Ile Leu Gly Asp Thr Ala Ile Val Ser
50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Glu Glu Gly
210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
                245                 250                 255

Leu Ser Gly His Leu Ile Asp Gln Lys Ala Asp Leu Thr Lys Asp Ile
            260                 265                 270

Lys Ala Leu Glu Ser Asn Val Glu Glu Gly Leu Leu Asp Leu Ser Gly
        275                 280                 285

Arg Leu Ile Asp Gln Lys Ala Asp Ile Ala Gln Asn Ala Asn Ile
290                 295                 300

Gln Asp Leu Ala Ala Tyr Asn Glu Leu Gln Asp Ala Tyr Ala Lys Gln
305                 310                 315                 320
```

```
Gln Thr Glu Ala Ile Asp Ala Leu Asn Lys Ala Ser Ser Glu Asn Thr
            325                 330                 335

Gln Asn Ile Glu Asp Leu Ala Ala Tyr Asn Glu Leu Gln Asp Ala Tyr
        340                 345                 350

Ala Lys Gln Gln Thr Glu Ala Ile Asp Ala Leu Asn Lys Ala Ser Ser
    355                 360                 365

Glu Asn Thr Gln Asn Ile Glu Asp Leu Ala Ala Tyr Asn Glu Leu Gln
370                 375                 380

Asp Ala Tyr Ala Lys Gln Gln Thr Glu Ala Ile Asp Ala Leu Asn Lys
385                 390                 395                 400

Ala Ser Ser Glu Asn Thr Gln Asn Ile Glu Asp Leu Ala Ala Tyr Asn
            405                 410                 415

Glu Leu Gln Asp Ala Tyr Ala Lys Gln Gln Thr Glu Ala Ile Asp Ala
        420                 425                 430

Leu Asn Lys Ala Ser Ser Glu Asn Thr Gln Asn Ile Ala Lys Asn Gln
    435                 440                 445

Ala Asp Ile Ala Asn Asn Ile Asn Ile Tyr Glu Leu Ala Gln Gln
    450                 455                 460

Gln Asp Gln His Ser Ser Asp Ile Lys Thr Leu Ala Lys Ala Ser Ala
465                 470                 475                 480

Ala Asn Thr Asp Arg Ile Ala Lys Asn Lys Ala Asp Ala Asp Ala Ser
            485                 490                 495

Phe Glu Thr Leu Thr Lys Asn Gln Asn Thr Leu Ile Glu Lys Asp Lys
        500                 505                 510

Glu His Asp Lys Leu Ile Thr Ala Asn Lys Thr Ala Ile Asp Ala Asn
    515                 520                 525

Lys Ala Ser Ala Asp Thr Lys Phe Ala Ala Thr Ala Asp Ala Ile Thr
530                 535                 540

Lys Asn Gly Asn Ala Ile Thr Lys Asn Ala Lys Ser Ile Thr Asp Leu
545                 550                 555                 560

Gly Thr Lys Val Asp Gly Phe Asp Gly Arg Val Thr Ala Leu Asp Thr
            565                 570                 575

Lys Val Asn Ala Leu Asp Thr Lys Val Asn Ala Phe Asp Gly Arg Ile
        580                 585                 590

Thr Ala Leu Asp Ser Lys Val Glu Asn Gly Met Ala Ala Gln Ala Ala
    595                 600                 605

Leu Ser Gly Leu Phe Gln Pro Tyr Ser Val Gly Lys Phe Asn Ala Thr
    610                 615                 620

Ala Ala Leu Gly Gly Tyr Gly Ser Lys Ser Ala Val Ala Ile Gly Ala
625                 630                 635                 640

Gly Tyr Arg Val Asn Pro Asn Leu Ala Phe Lys Ala Gly Ala Ala Ile
            645                 650                 655

Asn Thr Ser Gly Asn Lys Lys Gly Ser Tyr Asn Ile Gly Val Asn Tyr
        660                 665                 670

Glu Phe

<210> SEQ ID NO 48
<211> LENGTH: 613
<212> TYPE: PRT
<213> ORGANISM: Moraxella catarrhalis

<400> SEQUENCE: 48

Met Lys Thr Met Lys Leu Leu Pro Leu Lys Ile Ala Val Thr Ser Ala
1               5                   10                  15
```

```
Met Ile Ile Gly Leu Gly Ala Ala Ser Thr Ala Asn Ala Gln Ser Arg
                20                  25                  30

Asp Arg Ser Leu Glu Asp Ile Gln Asp Ser Ile Ser Lys Leu Val Gln
        35                  40                  45

Asp Asp Ile Asp Thr Leu Lys Gln Asp Gln Gln Lys Met Asn Lys Tyr
 50                  55                  60

Leu Leu Leu Asn Gln Leu Ala Asn Thr Leu Ile Thr Asp Glu Leu Asn
 65                  70                  75                  80

Asn Asn Val Ile Lys Asn Thr Asn Ser Ile Glu Ala Leu Gly Asp Glu
                 85                  90                  95

Ile Gly Trp Leu Glu Asn Asp Ile Ala Asp Leu Glu Glu Gly Val Glu
                100                 105                 110

Glu Leu Thr Lys Asn Gln Asn Thr Leu Ile Glu Lys Asp Glu Glu His
            115                 120                 125

Asp Arg Leu Ile Ala Gln Asn Gln Ala Asp Ile Gln Thr Leu Glu Asn
        130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
                180                 185                 190

Glu Glu Val Asn Lys Thr Leu Glu Asn Leu Ile Thr Asn Ser Val Lys
            195                 200                 205

Asn Thr Asp Asn Ile Asp Lys Asn Lys Ala Asp Ile Asp Asn Asn Ile
        210                 215                 220

Asn His Ile Tyr Glu Leu Ala Gln Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
                260                 265                 270

Leu Glu Ser Asn Val Glu Glu Gly Leu Leu Asp Leu Ser Gly Arg Leu
            275                 280                 285

Leu Asp Gln Lys Ala Asp Leu Thr Lys Asp Ile Lys Ala Leu Glu Ser
        290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
                340                 345                 350

Asp Ala Leu Asn Lys Ala Ser Ser Glu Asn Thr Gln Asn Ile Glu Asp
        355                 360                 365

Leu Ala Ala Tyr Asn Glu Leu Gln Asp Ala Tyr Ala Lys Gln Gln Thr
        370                 375                 380

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Ile Asn Asn Ile Tyr
                405                 410                 415

Glu Leu Ala Gln Gln Gln Asp Gln His Ser Ser Asp Ile Lys Thr Leu
            420                 425                 430

Ala Lys Ala Ser Ala Ala Asn Thr Asn Arg Ile Ala Thr Ala Glu Leu
```

```
            435                 440                 445
Gly Ile Ala Glu Asn Lys Lys Asp Ala Gln Ile Ala Lys Ala Gln Ala
    450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
        515                 520                 525

Gly Arg Ile Thr Ala Leu Asp Ser Lys Val Glu Asn Gly Met Ala Ala
    530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
        595                 600                 605

Val Asn Tyr Glu Phe
    610

<210> SEQ ID NO 49
<211> LENGTH: 576
<212> TYPE: PRT
<213> ORGANISM: Moraxella catarrhalis

<400> SEQUENCE: 49

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
            20                  25                  30

Glu Gln Phe Phe Pro Asn Ile Phe Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190
```

```
Ser Ser Ala Asn Thr Asp Arg Ile Asp Thr Ala Glu Glu Arg Ile Asp
            195                 200                 205

Lys Asn Glu Tyr Asp Ile Lys Ala Leu Glu Ser Asn Val Glu Glu Gly
            210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
            245                 250                 255

Leu Ser Gly His Leu Ile Asp Gln Lys Ala Asp Leu Thr Lys Asp Ile
            260                 265                 270

Lys Ala Leu Glu Ser Asn Val Glu Glu Gly Leu Leu Asp Leu Ser Gly
            275                 280                 285

Arg Leu Leu Asp Gln Lys Ala Asp Ile Ala Lys Asn Gln Ala Asp Ile
            290                 295                 300

Ala Gln Asn Gln Thr Asp Ile Gln Asp Leu Ala Ala Tyr Asn Glu Leu
305                 310                 315                 320

Gln Asp Ala Tyr Ala Lys Gln Gln Thr Glu Ala Ile Asp Ala Leu Asn
            325                 330                 335

Lys Ala Ser Ser Glu Asn Thr Gln Asn Ile Ala Lys Asn Gln Ala Asp
            340                 345                 350

Ile Ala Asn Asn Ile Asn Asn Ile Tyr Glu Leu Ala Gln Gln Gln Asp
            355                 360                 365

Gln His Ser Ser Asp Ile Lys Thr Leu Ala Lys Ala Ser Ala Ala Asn
            370                 375                 380

Thr Asp Arg Ile Ala Lys Asn Lys Ala Asp Ala Asp Ala Ser Phe Glu
385                 390                 395                 400

Thr Leu Thr Lys Asn Gln Asn Thr Leu Ile Glu Lys Asp Lys Glu His
            405                 410                 415

Asp Lys Leu Ile Thr Ala Asn Lys Thr Ala Ile Asp Ala Asn Lys Ala
            420                 425                 430

Ser Ala Asp Thr Lys Phe Ala Ala Thr Ala Asp Ala Ile Thr Lys Asn
            435                 440                 445

Gly Asn Ala Ile Thr Lys Asn Ala Lys Ser Ile Thr Asp Leu Gly Thr
450                 455                 460

Lys Val Asp Gly Phe Asp Gly Arg Val Thr Ala Leu Asp Thr Lys Val
465                 470                 475                 480

Asn Ala Leu Asp Thr Lys Val Asn Ala Phe Asp Gly Arg Ile Thr Ala
            485                 490                 495

Leu Asp Ser Lys Val Glu Asn Gly Met Ala Gln Ala Ala Leu Ser
            500                 505                 510

Gly Leu Phe Gln Pro Tyr Ser Val Gly Lys Phe Asn Ala Thr Ala Ala
            515                 520                 525

Leu Gly Gly Tyr Gly Ser Lys Ser Ala Val Ala Ile Gly Ala Gly Tyr
            530                 535                 540

Arg Val Asn Pro Asn Leu Ala Phe Lys Ala Gly Ala Ala Ile Asn Thr
545                 550                 555                 560

Ser Gly Asn Lys Lys Gly Ser Tyr Asn Ile Gly Val Asn Tyr Glu Phe
            565                 570                 575
```

<210> SEQ ID NO 50
<211> LENGTH: 684
<212> TYPE: PRT
<213> ORGANISM: Moraxella catarrhalis

<400> SEQUENCE: 50

```
Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Asp Thr Ile Ile Pro Leu Asp
                100                 105                 110

Glu Asn Gly Lys Pro Val Tyr Lys Leu Asp Ser Ile Val Glu Gln Gly
            115                 120                 125

Lys Thr Lys Thr Val Tyr Ser Val Thr Thr Lys Thr Ala Thr Ala Asp
        130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
                180                 185                 190

Val Gln Asn Asn Ile Glu Asn Ile His Glu Leu Ala Gln Gln Gln Asp
            195                 200                 205

Gln His Ser Ser Asp Ile Lys Thr Leu Lys Lys Asn Val Glu Lys Asp
        210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
                260                 265                 270

Ala Ser Ser Glu Asn Thr Gln Asn Ile Ala Lys Asn Ser Asn His Ile
            275                 280                 285

Lys Thr Leu Glu Asn Asn Ile Glu Glu Gly Leu Leu Glu Leu Ser Gly
        290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu
                340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
        370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415
```

```
Gln Asn Ile Glu Asp Leu Ala Ala Tyr Asn Glu Leu Gln Asp Ala Tyr
                420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
450                 455                 460

Ile Asn Asn Ile Tyr Glu Leu Ala Gln Gln Asp Gln His Ser Ser
465                 470                 475                 480

Asp Ile Lys Thr Leu Ala Lys Ala Ser Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
            675                 680

<210> SEQ ID NO 51
<211> LENGTH: 686
<212> TYPE: PRT
<213> ORGANISM: Moraxella catarrhalis

<400> SEQUENCE: 51

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Thr
                20                  25                  30

Glu Thr Phe Leu Pro Asn Leu Phe Asp Asn Asp Tyr Thr Glu Thr Thr
            35                  40                  45

Asp Pro Leu Tyr His Gly Met Ile Leu Gly Asn Thr Ala Ile Thr Gln
        50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Leu Asn Gly Phe
                85                  90                  95

Lys Glu Gly Asp Thr Ile Ile Pro Leu Asp Glu Asn Gly Lys Pro Val
            100                 105                 110
```

```
Tyr Lys Leu Asp Glu Ile Thr Glu Asn Gly Val Lys Arg Lys Val Tyr
        115                 120                 125

Ser Val Thr Thr Lys Thr Ala Thr Arg Glu Asp Val Glu Gln Ser Ala
130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Asp Gln His Ser Ser Asp
            195                 200                 205

Ile Lys Thr Leu Lys Lys Asn Val Glu Glu Gly Leu Leu Glu Leu Ser
        210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270

Thr Gln Asn Ile Ala Lys Asn Ser Asn His Ile Lys Thr Leu Glu Asn
        275                 280                 285

Asn Ile Glu Glu Gly Leu Leu Glu Leu Ser Gly His Leu Ile Asp Gln
            290                 295                 300

Lys Ala Asp Leu Thr Lys Asp Ile Lys Ala Leu Glu Ser Asn Val Glu
305                 310                 315                 320

Glu Gly Leu Leu Asp Leu Ser Gly Arg Leu Leu Asp Gln Lys Ala Asp
                325                 330                 335

Ile Ala Lys Asn Gln Ala Asp Ile Ala Gln Asn Gln Thr Asp Ile Gln
            340                 345                 350

Asp Leu Ala Ala Tyr Asn Glu Leu Gln Asp Gln Tyr Ala Gln Lys Gln
        355                 360                 365

Thr Glu Ala Ile Asp Ala Leu Asn Lys Ala Ser Ser Glu Asn Thr Gln
370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
            405                 410                 415

Asn Thr Gln Asn Ile Glu Asp Leu Ala Ala Tyr Asn Glu Leu Gln Asp
        420                 425                 430

Ala Tyr Ala Lys Gln Gln Thr Glu Ala Ile Asp Ala Leu Asn Lys Ala
        435                 440                 445

Ser Ser Glu Asn Thr Gln Asn Ile Ala Lys Asn Gln Ala Asp Ile Ala
        450                 455                 460

Asn Asn Ile Asn Asn Ile Tyr Glu Leu Ala Gln Gln Asp Gln His
465                 470                 475                 480

Ser Ser Asp Ile Lys Thr Leu Ala Lys Ala Ser Ala Ala Asn Thr Asp
                485                 490                 495

Arg Ile Ala Lys Asn Lys Ala Asp Ala Asp Ala Ser Phe Glu Thr Leu
            500                 505                 510

Thr Lys Asn Gln Asn Thr Leu Ile Glu Lys Asp Lys Glu His Asp Lys
        515                 520                 525
```

-continued

Leu Ile Thr Ala Asn Lys Thr Ala Ile Asp Ala Asn Lys Ala Ser Ala
     530                 535                 540

Asp Thr Lys Phe Ala Ala Thr Ala Asp Ala Ile Thr Lys Asn Gly Asn
545                 550                 555                 560

Ala Ile Thr Lys Asn Ala Lys Ser Ile Thr Asp Leu Gly Thr Lys Val
             565                 570                 575

Asp Gly Phe Asp Gly Arg Val Thr Ala Leu Asp Thr Lys Val Asn Ala
             580                 585                 590

Leu Asp Thr Lys Val Asn Ala Phe Asp Gly Arg Ile Thr Ala Leu Asp
         595                 600                 605

Ser Lys Val Glu Asn Gly Met Ala Ala Gln Ala Leu Ser Gly Leu
     610                 615                 620

Phe Gln Pro Tyr Ser Val Gly Lys Phe Asn Ala Thr Ala Leu Gly
625                 630                 635                 640

Gly Tyr Gly Ser Lys Ser Ala Val Ala Ile Gly Ala Gly Tyr Arg Val
             645                 650                 655

Asn Pro Asn Leu Ala Phe Lys Ala Gly Ala Ala Ile Asn Thr Ser Gly
             660                 665                 670

Asn Lys Lys Gly Ser Tyr Asn Ile Gly Val Asn Tyr Glu Phe
         675                 680                 685

<210> SEQ ID NO 52
<211> LENGTH: 630
<212> TYPE: PRT
<213> ORGANISM: Moraxella catarrhalis

<400> SEQUENCE: 52

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Glu Gly Lys Ile Leu Gln Asn Glu
    130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
    210                 215                 220

-continued

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
            245                 250                 255

Tyr Glu Leu Ala Gln Gln Gln Asp Gln His Ser Ser Asp Ile Lys Thr
                260                 265                 270

Leu Lys Lys Asn Val Glu Glu Gly Leu Leu Glu Leu Ser Gly His Leu
            275                 280                 285

Ile Asp Gln Lys Thr Asp Ile Ala Gln Asn Gln Ala Asn Ile Gln Asp
290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
                325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
                355                 360                 365

Thr Gln Asn Ile Glu Asp Leu Ala Ala Tyr Asn Glu Leu Gln Asp Ala
            370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
                405                 410                 415

Asn Ile Asn Asn Ile Tyr Glu Leu Ala Gln Gln Gln Asp Gln His Ser
            420                 425                 430

Ser Asp Ile Lys Thr Leu Ala Lys Ala Ser Ala Ala Asn Thr Asp Arg
            435                 440                 445

Ile Ala Lys Asn Lys Ala Asp Ala Asp Ala Ser Phe Glu Thr Leu Thr
450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
                485                 490                 495

Thr Lys Phe Ala Ala Thr Ala Asp Ala Ile Thr Lys Asn Gly Asn Ala
            500                 505                 510

Ile Thr Lys Asn Ala Lys Ser Ile Thr Asp Leu Gly Thr Lys Val Asp
            515                 520                 525

Gly Phe Asp Ser Arg Val Thr Ala Leu Asp Thr Lys Val Asn Ala Phe
            530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
                565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
            595                 600                 605

Gly Ala Ala Ile Asn Thr Ser Gly Asn Lys Lys Gly Ser Tyr Asn Ile
            610                 615                 620

Gly Val Asn Tyr Glu Phe
625                 630

-continued

<210> SEQ ID NO 53
<211> LENGTH: 616
<212> TYPE: PRT
<213> ORGANISM: Moraxella catarrhalis

<400> SEQUENCE: 53

```
Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
            20                  25                  30

Asp Arg Ser Leu Glu Gln Ile Gln Asp Lys Leu Ala Asn Leu Val Glu
        35                  40                  45

Lys Ile Glu Gln Ala Lys Ser Gln Asn Gly Gln Ser Gln Lys Asp Ile
50                  55                  60

Asn Gln Tyr Leu Leu Ser Gln Tyr Ala Asn Val Leu Thr Met Glu
65                  70                  75                  80

Glu Leu Asn Asn Asn Val Val Lys Asn Ser Ser Ile Glu Thr Leu
                85                  90                  95

Asp Asn Asp Ile Ala Trp Leu Asn Asp Leu Ile Asp Leu Asp Lys
            100                 105                 110

Glu Val Gly Val Leu Ser Arg Asp Ile Gly Ser Leu His Asp Asp Val
            115                 120                 125

Ala Gln Asn Gln Ala Asp Ile Lys Thr Leu Lys Asn Asn Val Val Glu
130                 135                 140

Glu Leu Phe Asn Leu Ser Asp Arg Leu Ile Asp Gln Glu Ala Asp Ile
145                 150                 155                 160

Ala Gln Asn Asn Glu Ser Ile Glu Asp Leu Tyr Asp Phe Gly Arg Glu
                165                 170                 175

Val Ala Glu Ser Ile Gly Glu Ile His Ala His Asn Glu Ala Gln Asn
            180                 185                 190

Glu Thr Leu Lys Asp Leu Ile Thr Asn Ser Val Lys Asn Thr Asp Asn
        195                 200                 205

Ile Thr Lys Asn Lys Ala Asp Ile Gln Ala Leu Glu Asn Asp Val Gly
    210                 215                 220

Lys Glu Leu Leu Asn Leu Ser Gly Arg Leu Ile Asp Gln Lys Ala Asp
225                 230                 235                 240

Ile Asp Asn Asn Ile Asn His Ile Tyr Glu Leu Ala Gln Gln Gln Asp
                245                 250                 255

Gln His Ser Ser Asp Ile Lys Thr Leu Lys Asn Asn Val Glu Glu Gly
            260                 265                 270

Leu Leu Glu Leu Ser Gly His Leu Ile Asp Gln Lys Ala Asp Leu Thr
        275                 280                 285

Lys Asp Ile Lys Ala Leu Glu Ser Asn Val Glu Glu Gly Leu Leu Asp
    290                 295                 300

Leu Ser Gly Arg Leu Leu Asp Gln Lys Ala Asp Ile Ala Gln Asn Gln
305                 310                 315                 320

Ala Asn Ile Gln Asp Leu Ala Ala Tyr Asn Glu Leu Gln Asp Ala Tyr
                325                 330                 335

Ala Lys Gln Gln Thr Glu Ala Ile Asp Ala Leu Asn Lys Ala Ser Ser
            340                 345                 350

Glu Asn Thr Gln Asn Ile Glu Asp Leu Ala Ala Tyr Asn Glu Leu Gln
        355                 360                 365

Asp Ala Tyr Ala Lys Gln Gln Thr Glu Ala Ile Asp Ala Leu Asn Lys
    370                 375                 380
```

```
Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Ala Ser Ala Ala Asn Thr
            420                 425                 430

Asp Arg Ile Ala Lys Asn Lys Ala Asp Ala Asp Ala Ser Phe Glu Thr
        435                 440                 445

Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Ala Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
            500                 505                 510

Val Asp Gly Phe Asp Ser Arg Val Thr Ala Leu Asp Thr Lys Val Asn
        515                 520                 525

Ala Phe Asp Gly Arg Ile Thr Ala Leu Asp Ser Lys Val Glu Asn Gly
    530                 535                 540

Met Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
    610                 615

<210> SEQ ID NO 54
<211> LENGTH: 614
<212> TYPE: PRT
<213> ORGANISM: Moraxella catarrhalis

<400> SEQUENCE: 54

Met Lys Thr Met Lys Leu Leu Pro Leu Lys Ile Ala Val Thr Ser Ala
1               5                   10                  15

Met Ile Ile Gly Leu Gly Ala Thr Ser Thr Val Asn Ala Gln Val Val
            20                  25                  30

Glu Gln Phe Phe Pro Asn Ile Phe Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
```

```
                    130                 135                 140
Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                    165                 170                 175

Asp Tyr Asn Glu Arg Gln Thr Glu Ala Ile Asp Ala Leu Asn Lys Ala
                180                 185                 190

Ser Ser Ala Asn Thr Asp Arg Ile Asp Thr Ala Glu Glu Arg Ile Asp
            195                 200                 205

Lys Asn Glu Tyr Asp Ile Lys Ala Leu Glu Ser Asn Val Gly Lys Asp
        210                 215                 220

Leu Leu Asp Leu Ser Gly Arg Leu Ile Ala Gln Lys Glu Asp Ile Asp
225                 230                 235                 240

Asn Asn Ile Asn His Ile Tyr Glu Leu Ala Gln Gln Asp Gln His
                    245                 250                 255

Ser Ser Asp Ile Lys Thr Leu Lys Asn Asn Val Glu Glu Gly Leu Leu
                260                 265                 270

Glu Leu Ser Gly His Leu Ile Asp Gln Lys Ala Asp Leu Thr Lys Asp
            275                 280                 285

Ile Lys Thr Leu Glu Ser Asn Val Glu Glu Gly Leu Leu Asp Leu Ser
        290                 295                 300

Gly Arg Leu Ile Asp Gln Lys Ala Asp Ile Ala Gln Asn Gln Ala Asn
305                 310                 315                 320

Ile Gln Asp Leu Ala Ala Tyr Asn Glu Leu Gln Asp Gln Tyr Ala Gln
                    325                 330                 335

Lys Gln Thr Glu Ala Ile Asp Ala Leu Asn Lys Ala Ser Ser Glu Asn
                340                 345                 350

Thr Gln Asn Ile Glu Asp Leu Ala Ala Tyr Asn Glu Leu Gln Asp Ala
            355                 360                 365

Tyr Ala Lys Gln Gln Thr Glu Ala Ile Asp Ala Leu Asn Lys Ala Ser
        370                 375                 380

Ser Glu Asn Thr Gln Asn Ile Ala Lys Asn Gln Ala Asp Ile Ala Asn
385                 390                 395                 400

Asn Ile Asn Asn Ile Tyr Glu Leu Ala Gln Gln Asp Gln His Ser
                    405                 410                 415

Ser Asp Ile Lys Thr Leu Ala Lys Val Ser Ala Ala Asn Thr Asp Arg
            420                 425                 430

Ile Ala Lys Asn Lys Ala Asp Ala Ser Phe Glu Thr Leu Thr
        435                 440                 445

Lys Asn Gln Asn Thr Leu Ile Glu Lys Asp Lys Glu His Asp Lys Leu
450                 455                 460

Ile Thr Ala Asn Lys Thr Ala Ile Asp Ala Asn Lys Ala Ser Ala Asp
465                 470                 475                 480

Thr Lys Phe Ala Ala Thr Ala Asp Ala Ile Thr Lys Asn Gly Asn Ala
                485                 490                 495

Ile Thr Lys Asn Ala Lys Ser Ile Thr Asp Leu Gly Thr Lys Val Asp
            500                 505                 510

Gly Phe Asp Gly Arg Val Thr Ala Leu Asp Thr Lys Val Asn Ala Phe
        515                 520                 525

Asp Gly Arg Ile Thr Ala Leu Asp Ser Lys Val Glu Asn Gly Met Ala
    530                 535                 540

Ala Gln Ala Ala Leu Ser Gly Leu Phe Gln Pro Tyr Ser Val Gly Lys
545                 550                 555                 560
```

```
Phe Asn Ala Thr Ala Ala Leu Gly Gly Tyr Gly Ser Lys Ser Ala Val
                565                 570                 575

Ala Ile Gly Ala Gly Tyr Arg Val Asn Pro Asn Leu Ala Phe Lys Ala
            580                 585                 590

Gly Ala Ala Ile Asn Thr Ser Gly Asn Lys Lys Gly Ser Tyr Asn Ile
            595                 600                 605

Gly Val Asn Tyr Glu Phe
        610

<210> SEQ ID NO 55
<211> LENGTH: 679
<212> TYPE: PRT
<213> ORGANISM: Moraxella catarrhalis

<400> SEQUENCE: 55

Met Lys Thr Met Lys Leu Pro Pro Leu Lys Ile Ala Val Thr Ser Ala
1               5                   10                  15

Met Ile Ile Gly Leu Gly Ala Ala Ser Thr Ala Asn Ala Gln Thr Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asp Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Leu Leu Asn Gly Phe
                85                  90                  95

Lys Ala Gly Asp Thr Ile Ile Pro Leu Asp Glu Asn Gly Lys Pro Val
            100                 105                 110

Tyr Lys Leu Asp Glu Arg Thr Glu Asn Gly Val Lys Arg Lys Val Tyr
        115                 120                 125

Ser Val Thr Thr Lys Thr Ala Thr Gln Ala Asp Val Glu Gln Ser Ala
    130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Arg Glu Val Gln Asn Asn Ile
            180                 185                 190

Glu Asn Ile His Glu Leu Ala Gln Gln Asp Gln His Ser Ser Asp
        195                 200                 205

Ile Lys Thr Leu Lys Lys Asn Val Glu Lys Asp Leu Leu Asp Leu Ser
    210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270

Thr Gln Asn Ile Ala Lys Asn Ser Asn His Ile Lys Thr Leu Glu Asn
        275                 280                 285

Asn Ile Glu Glu Cys Leu Leu Glu Leu Ser Gly His Leu Ile Asp Gln
    290                 295                 300

Lys Ala Asp Leu Thr Lys Asp Ile Lys Ala Leu Glu Ser Asn Val Glu
```

```
305                 310                 315                 320
Glu Gly Leu Leu Asp Leu Ser Gly Arg Leu Ile Asp Gln Lys Ala Asp
                325                 330                 335

Ile Ala Gln Asn Gln Ala Asn Ile Gln Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Glu Asp Leu Ala Ala
    370                 375                 380

Tyr Asn Glu Leu Gln Asp Ala Tyr Ala Lys Gln Gln Thr Glu Ala Ile
385                 390                 395                 400

Asp Ala Leu Asn Lys Ala Ser Ser Glu Asn Thr Gln Asn Ile Glu Asp
                405                 410                 415

Leu Ala Ala Tyr Asn Glu Leu Gln Asp Ala Tyr Ala Lys Gln Gln Thr
            420                 425                 430

Glu Ala Ile Asp Ala Leu Asn Lys Ala Ser Ser Glu Asn Thr Gln Asn
        435                 440                 445

Ile Ala Lys Asn Gln Ala Asp Ile Ala Asn Asn Ile Asn Asn Ile Tyr
    450                 455                 460

Glu Leu Ala Gln Gln Gln Asp Gln His Ser Ser Asp Ile Lys Thr Leu
465                 470                 475                 480

Ala Lys Ala Ser Ala Ala Asn Thr Asp Arg Ile Ala Lys Asn Lys Ala
                485                 490                 495

Asp Ala Asp Ala Ser Phe Glu Thr Leu Thr Lys Asn Gln Asn Thr Leu
            500                 505                 510

Ile Glu Lys Asp Lys Glu His Asp Lys Leu Ile Thr Ala Asn Lys Thr
        515                 520                 525

Ala Ile Asp Ala Asn Lys Ala Ser Ala Asp Thr Lys Phe Ala Ala Thr
    530                 535                 540

Ala Asp Ala Ile Thr Lys Asn Gly Asn Ala Ile Thr Lys Asn Ala Lys
545                 550                 555                 560

Ser Ile Thr Asp Leu Gly Thr Lys Val Asp Gly Phe Asp Gly Arg Val
                565                 570                 575

Thr Ala Leu Asp Thr Lys Val Asn Ala Leu Asp Thr Lys Val Asn Ala
            580                 585                 590

Phe Asp Gly Arg Ile Thr Ala Leu Asp Ser Lys Val Glu Asn Gly Met
        595                 600                 605

Ala Ala Gln Ala Ala Leu Ser Gly Leu Phe Gln Pro Tyr Ser Val Gly
    610                 615                 620

Lys Phe Asn Ala Thr Ala Ala Leu Gly Gly Tyr Gly Ser Lys Ser Ala
625                 630                 635                 640

Val Ala Ile Gly Ala Gly Tyr Arg Val Asn Pro Asn Leu Ala Phe Lys
                645                 650                 655

Ala Gly Ala Ala Ile Asn Thr Ser Gly Asn Lys Lys Gly Ser Tyr Asn
            660                 665                 670

Ile Gly Val Asn Tyr Glu Phe
        675

<210> SEQ ID NO 56
<211> LENGTH: 724
<212> TYPE: PRT
<213> ORGANISM: Moraxella catarrhalis

<400> SEQUENCE: 56
```

-continued

```
Met Lys Thr Met Lys Leu Leu Pro Leu Lys Ile Ala Val Thr Ser Ala
1               5                   10                  15
Leu Ile Val Gly Leu Gly Ala Ala Ser Thr Ala Asn Ala Gln Glu Thr
            20                  25                  30
Leu Glu Glu Val Leu Glu Ser Ile Lys Gln Ile Asn Glu Gln Asp Leu
        35                  40                  45
Gln Asp Asp Ile Gly Tyr Asn Ser Ala Leu Asp Arg Tyr Leu Val Leu
    50                  55                  60
Ser Gln Tyr Gly Asn Leu Leu Ile Ala Lys Glu Leu Asn Glu Asn Val
65                  70                  75                  80
Glu Lys Asn Ser Asn Ser Ile Ala Lys Asn Ser Asn Ser Ile Ala Asp
                85                  90                  95
Leu Glu Ala Asp Val Gly Tyr Leu Ala Glu Asn Gln Asn Thr Leu Ile
            100                 105                 110
Glu Gln Asn Glu Thr Ile Asn Gln Glu Leu Glu Gly Ile Thr His Glu
        115                 120                 125
Leu Glu Ser Phe Ile Ala Tyr Ala His Ala Gln Asp Gln Lys Asn Leu
    130                 135                 140
Val Asn Glu Phe Glu Ile Glu Lys Asn Lys Asp Ala Ile Ala Lys Asn
145                 150                 155                 160
Asn Glu Ser Ile Glu Asp Leu Tyr Asp Phe Gly His Glu Val Ala Glu
                165                 170                 175
Ser Ile Gly Glu Ile His Ala Tyr Thr Glu Glu Val Asn Lys Thr Leu
            180                 185                 190
Glu Asn Leu Ile Thr Asn Ser Val Lys Asn Thr Asp Asn Ile Thr Lys
        195                 200                 205
Asn Lys Ala Asp Ile Gln Ala Leu Glu Ser Asn Val Glu Lys Glu Leu
    210                 215                 220
Leu Asn Leu Ser Gly Arg Leu Ile Asp Gln Lys Ala Asp Ile Asp Asn
225                 230                 235                 240
Asn Ile Asn His Ile Tyr Glu Leu Ala Gln Gln Gln Asp Gln His Ser
                245                 250                 255
Ser Asp Ile Lys Thr Leu Lys Lys Asn Val Glu Glu Gly Leu Leu Glu
            260                 265                 270
Leu Ser Gly His Leu Ile Asp Gln Lys Ser Asp Ile Ala Gln Asn Gln
        275                 280                 285
Thr Asp Ile Gln Asp Leu Ala Thr Tyr Asn Glu Leu Gln Asp Gln Tyr
    290                 295                 300
Ala Gln Lys Gln Thr Glu Ala Ile Asp Ala Leu Asn Lys Ala Ser Ser
305                 310                 315                 320
Glu Asn Thr Gln Asn Ile Glu Asp Leu Ala Ala Tyr Asn Glu Leu Gln
                325                 330                 335
Asp Ala Tyr Ala Lys Gln Gln Thr Glu Ala Ile Asp Ala Leu Asn Lys
            340                 345                 350
Ala Ser Ser Glu Asn Thr Gln Asn Ile Glu Asp Leu Ala Ala Tyr Asn
        355                 360                 365
Glu Leu Gln Asp Ala Tyr Ala Lys Gln Gln Thr Glu Ala Ile Asp Ala
    370                 375                 380
Leu Asn Lys Ala Ser Ser Glu Asn Thr Gln Asn Ile Glu Asp Leu Ala
385                 390                 395                 400
Ala Tyr Asn Glu Leu Gln Asp Ala Tyr Ala Lys Gln Gln Thr Glu Ala
                405                 410                 415
Ile Asp Ala Leu Asn Lys Ala Ser Ser Glu Asn Thr Gln Asn Ile Glu
```

```
                    420                 425                 430
Asp Leu Ala Ala Tyr Asn Glu Leu Gln Asp Ala Tyr Ala Lys Gln Gln
            435                 440                 445

Thr Glu Ala Ile Asp Ala Leu Asn Lys Ala Ser Ser Glu Asn Thr Gln
        450                 455                 460

Asn Ile Glu Asp Leu Ala Ala Tyr Asn Glu Leu Gln Asp Ala Tyr Ala
465                 470                 475                 480

Lys Gln Gln Thr Glu Ala Ile Asp Ala Leu Asn Lys Ala Ser Ser Glu
                485                 490                 495

Asn Thr Gln Asn Ile Ala Lys Asn Gln Ala Asp Ile Ala Asn Asn Ile
            500                 505                 510

Asn Asn Ile Tyr Glu Leu Ala Gln Gln Gln Asp Gln His Ser Ser Asp
        515                 520                 525

Ile Lys Thr Leu Ala Lys Ala Ser Ala Ala Asn Thr Asp Arg Ile Ala
            530                 535                 540

Lys Asn Lys Ala Asp Ala Asp Ala Ser Phe Glu Thr Leu Thr Lys Asn
545                 550                 555                 560

Gln Asn Thr Leu Ile Glu Lys Asp Lys Glu His Asp Lys Leu Ile Thr
                565                 570                 575

Ala Asn Lys Thr Ala Ile Asp Ala Asn Lys Ala Ser Ala Asp Thr Lys
            580                 585                 590

Phe Ala Ala Thr Ala Asp Ala Ile Thr Lys Asn Gly Asn Ala Ile Thr
        595                 600                 605

Lys Asn Ala Lys Ser Ile Thr Asp Leu Gly Thr Lys Val Asp Gly Phe
            610                 615                 620

Asp Ser Arg Val Thr Ala Leu Asp Thr Lys Val Asn Ala Phe Asp Gly
625                 630                 635                 640

Arg Ile Thr Ala Leu Asp Ser Lys Val Glu Asn Gly Met Ala Ala Gln
                645                 650                 655

Ala Ala Leu Ser Gly Leu Phe Gln Pro Tyr Ser Val Gly Lys Phe Asn
            660                 665                 670

Ala Thr Ala Ala Leu Gly Gly Tyr Gly Ser Lys Ser Ala Val Ala Ile
        675                 680                 685

Gly Ala Gly Tyr Arg Val Asn Pro Asn Leu Ala Phe Lys Ala Gly Ala
            690                 695                 700

Ala Ile Asn Thr Ser Gly Asn Lys Lys Gly Ser Tyr Asn Ile Gly Val
705                 710                 715                 720

Asn Tyr Glu Phe

<210> SEQ ID NO 57
<211> LENGTH: 611
<212> TYPE: PRT
<213> ORGANISM: Moraxella catarrhalis

<400> SEQUENCE: 57

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
            20                  25                  30

Ala Arg Asp Arg Ser Leu Glu Asp Ile Gln Ala Leu Ile Gly Asn Ile
        35                  40                  45

Asp Val Asp Lys Ile Arg Ser Gln Lys Gln Lys Asn Pro Glu Ile Phe
    50                  55                  60

Gln Tyr Leu Leu Leu Asn Gln Leu Ser Asn Thr Leu Ile Thr Asp Glu
```

```
             65                  70                  75                  80
Leu Asn Asn Val Ile Lys Asn Thr Asn Ser Ile Glu Thr Leu Asp
                85                  90                  95
Asn Asp Ile Ala Trp Leu Asn Asp Asp Leu Ile Asp Leu Asp Lys Glu
                100                 105                 110
Val Gly Val Leu Ser Arg Asp Ile Gly Ser Leu His Asp Asp Val Ala
                115                 120                 125
Gln Asn Gln Ala Asp Ile Lys Thr Leu Glu Asn Asn Val Val Glu Glu
        130                 135                 140
Leu Phe Asn Leu Ser Asp Arg Leu Ile Asp Gln Glu Ala Glu Ile Ala
145                 150                 155                 160
Gln Asn Asn Glu Ser Ile Glu Asp Leu Tyr Asp Phe Gly Arg Glu Val
                165                 170                 175
Ala Glu Ser Ile Gly Glu Ile His Ala His Asn Glu Ala Gln Asn Glu
                180                 185                 190
Thr Leu Lys Asp Leu Ile Thr Asn Ser Val Lys Asn Thr Asp Asn Ile
                195                 200                 205
Asp Lys Asn Lys Ala Asp Ile Gln Ala Leu Glu Asn Asn Val Glu Glu
        210                 215                 220
Gly Leu Leu Glu Leu Ser Gly His Leu Ile Asp Gln Lys Ala Asp Leu
225                 230                 235                 240
Thr Lys Asp Ile Lys Ala Leu Glu Ser Asn Val Glu Glu Gly Leu Leu
                245                 250                 255
Asp Leu Ser Gly Arg Leu Leu Asp Gln Lys Ala Asp Ile Ala Lys Asn
                260                 265                 270
Gln Ala Asp Ile Ala Gln Asn Gln Thr Asp Ile Gln Asp Leu Ala Ala
        275                 280                 285
Tyr Asn Glu Leu Gln Asp Gln Tyr Ala Gln Lys Gln Thr Glu Ala Ile
        290                 295                 300
Asp Ala Leu Asn Lys Ala Ser Ser Glu Asn Thr Gln Asn Ile Glu Asp
305                 310                 315                 320
Leu Ala Ala Tyr Asn Glu Leu Gln Asp Ala Tyr Ala Lys Gln Gln Thr
                325                 330                 335
Glu Ala Ile Asp Ala Leu Asn Lys Ala Ser Ser Glu Asn Thr Gln Asn
                340                 345                 350
Ile Glu Asp Leu Ala Ala Tyr Asn Glu Leu Gln Asp Ala Tyr Ala Lys
                355                 360                 365
Gln Gln Thr Glu Ala Ile Asp Ala Leu Asn Lys Ala Ser Ser Glu Asn
        370                 375                 380
Thr Gln Asn Ile Ala Lys Asn Gln Ala Asp Ile Ala Asn Asn Ile Asn
385                 390                 395                 400
Asn Ile Tyr Glu Leu Ala Gln Gln Gln Asp Gln His Ser Ser Asp Ile
                405                 410                 415
Lys Thr Leu Ala Lys Val Ser Ala Ala Asn Thr Asp Arg Ile Ala Lys
                420                 425                 430
Asn Lys Ala Asp Ala Asp Ala Ser Phe Glu Thr Leu Thr Lys Asn Gln
                435                 440                 445
Asn Thr Leu Ile Glu Lys Asp Lys Glu His Asp Lys Leu Ile Thr Ala
                450                 455                 460
Asn Lys Thr Ala Ile Asp Ala Asn Lys Ala Ser Ala Asp Thr Lys Phe
465                 470                 475                 480
Ala Ala Thr Ala Asp Ala Ile Thr Lys Asn Gly Asn Ala Ile Thr Lys
                485                 490                 495
```

```
Asn Ala Lys Ser Ile Thr Asp Leu Gly Thr Lys Val Asp Gly Phe Asp
            500                 505                 510

Ser Arg Val Thr Ala Leu Asp Thr Lys Val Asn Ala Phe Asp Gly Arg
        515                 520                 525

Ile Thr Ala Leu Asp Ser Lys Val Glu Asn Gly Met Ala Ala Gln Ala
    530                 535                 540

Ala Leu Ser Gly Leu Phe Gln Pro Tyr Ser Val Gly Lys Phe Asn Ala
545                 550                 555                 560

Thr Ala Ala Leu Gly Gly Tyr Gly Ser Lys Ser Ala Val Ala Ile Gly
                565                 570                 575

Ala Gly Tyr Arg Val Asn Pro Asn Leu Ala Phe Lys Ala Gly Ala Ala
            580                 585                 590

Ile Asn Thr Ser Gly Asn Lys Lys Gly Ser Tyr Asn Ile Gly Val Asn
                595                 600                 605

Tyr Glu Phe
    610
```

<210> SEQ ID NO 58
<211> LENGTH: 10
<212> TYPE: PRT
<213> ORGANISM: H. influenzae

<400> SEQUENCE: 58

```
Ser Ser His Ser Ser Asn Met Ala Asn Thr
1               5                   10
```

<210> SEQ ID NO 59
<211> LENGTH: 141
<212> TYPE: PRT
<213> ORGANISM: H. influenzae

<400> SEQUENCE: 59

```
Ile Gln Lys Ala Glu Gln Asn Asp Val Lys Leu Ala Pro Pro Thr Asp
1               5                   10                  15

Val Arg Ser Gly Tyr Ile Arg Leu Val Lys Asn Val Asn Tyr Tyr Ile
            20                  25                  30

Asp Ser Glu Ser Ile Trp Val Asp Asn Gln Glu Pro Gln Ile Val His
        35                  40                  45

Phe Asp Ala Val Val Asn Leu Asp Lys Gly Leu Tyr Val Tyr Pro Glu
    50                  55                  60

Pro Lys Arg Tyr Ala Arg Ser Val Arg Gln Tyr Lys Ile Leu Asn Cys
65                  70                  75                  80

Ala Asn Tyr His Leu Thr Gln Val Arg Thr Asp Phe Tyr Asp Glu Phe
                85                  90                  95

Trp Gly Gln Gly Leu Arg Ala Ala Pro Lys Lys Gln Lys Lys His Thr
            100                 105                 110

Leu Ser Leu Thr Pro Asp Thr Thr Leu Tyr Asn Ala Ala Gln Ile Ile
        115                 120                 125

Cys Ala Asn Tyr Gly Glu Ala Phe Ser Val Asp Lys Lys
    130                 135                 140
```

<210> SEQ ID NO 60
<211> LENGTH: 110
<212> TYPE: PRT
<213> ORGANISM: H. influenzae

<400> SEQUENCE: 60

```
Thr Lys Lys Ala Ala Val Ser Glu Leu Leu Gln Ala Ser Ala Pro Tyr
1               5                   10                  15

Lys Ala Asp Val Glu Leu Cys Val Tyr Ser Thr Asn Glu Thr Thr Asn
            20                  25                  30

Cys Thr Gly Gly Lys Asn Gly Ile Ala Ala Asp Ile Thr Thr Ala Lys
        35                  40                  45

Gly Tyr Val Lys Ser Val Thr Thr Ser Asn Gly Ala Ile Thr Val Lys
    50                  55                  60

Gly Asp Gly Thr Leu Ala Asn Met Glu Tyr Ile Leu Gln Ala Thr Gly
65                  70                  75                  80

Asn Ala Ala Thr Gly Val Thr Trp Thr Thr Thr Cys Lys Gly Thr Asp
                85                  90                  95

Ala Ser Leu Phe Pro Ala Asn Phe Cys Gly Ser Val Thr Gln
            100                 105                 110

<210> SEQ ID NO 61
<211> LENGTH: 520
<212> TYPE: PRT
<213> ORGANISM: Moraxella catarrhalis

<400> SEQUENCE: 61

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
            115                 120                 125

Asn Gly Phe Glu Ile Glu Lys Asn Lys Asp Ala Ile Ala Lys Asn Asn
        130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
            180                 185                 190

Lys Ala Asp Ile Gln Ala Leu Glu Asn Asn Val Val Glu Glu Leu Phe
            195                 200                 205

Asn Leu Ser Gly Arg Leu Ile Asp Gln Lys Ala Asp Ile Asp Asn Asn
        210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270
```

Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
        290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

Ala Ser His His His His His His
            515                 520

<210> SEQ ID NO 62
<211> LENGTH: 512
<212> TYPE: PRT
<213> ORGANISM: Moraxella catarrhalis

<400> SEQUENCE: 62

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val

```
                    115                 120                 125
Asn Gly Phe Glu Ile Glu Lys Asn Lys Asp Ala Ile Ala Lys Asn Asn
            130                 135                 140
Glu Ser Ile Glu Asp Leu Tyr Asp Phe Gly His Glu Val Ala Glu Ser
145                 150                 155                 160
Ile Gly Glu Ile His Ala His Asn Glu Ala Gln Asn Glu Thr Leu Lys
                165                 170                 175
Gly Leu Ile Thr Asn Ser Ile Glu Asn Thr Asn Asn Ile Thr Lys Asn
            180                 185                 190
Lys Ala Asp Ile Gln Ala Leu Glu Asn Val Val Glu Glu Leu Phe
        195                 200                 205
Asn Leu Ser Gly Arg Leu Ile Asp Gln Lys Ala Asp Ile Asp Asn Asn
        210                 215                 220
Ile Asn Asn Ile Tyr Glu Leu Ala Gln Gln Asp Gln His Ser Ser
225                 230                 235                 240
Asp Ile Lys Thr Leu Lys Lys Asn Val Glu Glu Gly Leu Leu Glu Leu
                245                 250                 255
Ser Gly His Leu Ile Asp Gln Lys Thr Asp Ile Ala Gln Asn Gln Ala
            260                 265                 270
Asn Ile Gln Asp Leu Ala Thr Tyr Asn Glu Leu Gln Asp Gln Tyr Ala
        275                 280                 285
Gln Lys Gln Thr Glu Ala Ile Asp Ala Leu Asn Lys Ala Ser Ser Glu
290                 295                 300
Asn Thr Gln Asn Ile Glu Asp Leu Ala Ala Tyr Asn Glu Leu Gln Asp
305                 310                 315                 320
Ala Tyr Ala Lys Gln Gln Thr Glu Ala Ile Asp Ala Leu Asn Lys Ala
                325                 330                 335
Ser Ser Glu Asn Thr Gln Asn Ile Glu Asp Leu Ala Ala Tyr Asn Glu
            340                 345                 350
Leu Gln Asp Ala Tyr Ala Lys Gln Gln Thr Glu Ala Ile Asp Ala Leu
        355                 360                 365
Asn Lys Ala Ser Ser Glu Asn Thr Gln Asn Ile Ala Lys Asn Gln Ala
370                 375                 380
Asp Ile Ala Asn Asn Ile Asn Asn Ile Tyr Glu Leu Ala Gln Gln Gln
385                 390                 395                 400
Asp Gln His Ser Ser Asp Ile Lys Thr Leu Ala Lys Ala Ser Ala Ala
                405                 410                 415
Asn Thr Asp Arg Ile Ala Lys Asn Lys Ala Asp Ala Asp Ala Ser Phe
            420                 425                 430
Glu Thr Leu Thr Lys Asn Gln Asn Thr Leu Ile Glu Lys Asp Lys Glu
        435                 440                 445
His Asp Lys Leu Ile Thr Ala Asn Lys Thr Ala Ile Asp Ala Asn Lys
        450                 455                 460
Ala Ser Ala Asp Thr Lys Phe Ala Ala Thr Ala Asp Ala Ile Thr Lys
465                 470                 475                 480
Asn Gly Asn Ala Ile Thr Lys Asn Ala Lys Ser Ile Thr Asp Leu Gly
                485                 490                 495
Thr Lys Val Asp Gly Phe Asp Ser Arg Val Thr Ala Leu Asp Thr Lys
            500                 505                 510

<210> SEQ ID NO 63
<211> LENGTH: 513
<212> TYPE: PRT
<213> ORGANISM: Moraxella catarrhalis
```

<400> SEQUENCE: 63

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala

-continued

```
                405                 410                 415
Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

His
```

<210> SEQ ID NO 64
<211> LENGTH: 514
<212> TYPE: PRT
<213> ORGANISM: Moraxella catarrhalis

<400> SEQUENCE: 64

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
```

```
            260                 265                 270
Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
        290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

His His

<210> SEQ ID NO 65
<211> LENGTH: 499
<212> TYPE: PRT
<213> ORGANISM: Moraxella catarrhalis

<400> SEQUENCE: 65

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
```

```
            115                 120                 125
Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ala Ser His His His
                485                 490                 495

His His His

<210> SEQ ID NO 66
<211> LENGTH: 491
<212> TYPE: PRT
<213> ORGANISM: Moraxella catarrhalis
```

<400> SEQUENCE: 66

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
            85                  90                  95

Asp Leu Gln Gly Leu Ala Asp Phe Val Glu Gly Gln Glu Gly Lys Ile
        100                 105                 110

Leu Gln Asn Glu Thr Ser Ile Lys Lys Asn Thr Gln Arg Asn Leu Val
    115                 120                 125

Asn Gly Phe Glu Ile Glu Lys Asn Lys Asp Ala Ile Ala Lys Asn Asn
130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
            165                 170                 175

Gly Leu Ile Thr Asn Ser Ile Glu Asn Thr Asn Asn Ile Thr Lys Asn
        180                 185                 190

Lys Ala Asp Ile Gln Ala Leu Glu Asn Asn Val Val Glu Glu Leu Phe
    195                 200                 205

Asn Leu Ser Gly Arg Leu Ile Asp Gln Lys Ala Asp Ile Asp Asn Asn
210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
            245                 250                 255

Ser Gly His Leu Ile Asp Gln Lys Thr Asp Ile Ala Gln Asn Gln Ala
        260                 265                 270

Asn Ile Gln Asp Leu Ala Thr Tyr Asn Glu Leu Gln Asp Gln Tyr Ala
    275                 280                 285

Gln Lys Gln Thr Glu Ala Ile Asp Ala Leu Asn Lys Ala Ser Ser Glu
290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
            325                 330                 335

Ser Ser Glu Asn Thr Gln Asn Ile Glu Asp Leu Ala Ala Tyr Asn Glu
        340                 345                 350

Leu Gln Asp Ala Tyr Ala Lys Gln Gln Thr Glu Ala Ile Asp Ala Leu
    355                 360                 365

Asn Lys Ala Ser Ser Glu Asn Thr Gln Asn Ile Ala Lys Asn Gln Ala
370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415
```

```
Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser
                485                 490

<210> SEQ ID NO 67
<211> LENGTH: 544
<212> TYPE: PRT
<213> ORGANISM: Moraxella catarrhalis

<400> SEQUENCE: 67

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
```

```
        290                 295                 300
Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
                340                 345                 350

Leu Gln Asp Ala Tyr Ala Lys Gln Gln Thr Glu Ala Ile Asp Ala Leu
                355                 360                 365

Asn Lys Ala Ser Ser Glu Asn Thr Gln Asn Ile Ala Lys Asn Gln Ala
                370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
                420                 425                 430

Glu Thr Leu Thr Lys Asn Gln Asn Thr Leu Ile Glu Lys Asp Lys Glu
                435                 440                 445

His Asp Lys Leu Ile Thr Ala Asn Lys Thr Ala Ile Asp Ala Asn Lys
                450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
                500                 505                 510

Val Asn Ala Phe Asp Gly Arg Ile Thr Ala Leu Asp Ser Lys Val Glu
                515                 520                 525

Asn Gly Met Ala Ala Gln Ala Ala Ala Ser His His His His His
                530                 535                 540

<210> SEQ ID NO 68
<211> LENGTH: 538
<212> TYPE: PRT
<213> ORGANISM: Moraxella catarrhalis

<400> SEQUENCE: 68

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
                20                  25                  30

Ala Leu Glu Lys Tyr Leu Ala Leu Ser Gln Tyr Gly Asn Ile Leu Ala
                35                  40                  45

Leu Glu Glu Leu Asn Lys Ala Leu Glu Leu Asp Glu Asp Val Gly
                50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
                100                 105                 110

Leu Gln Asn Glu Thr Ser Ile Lys Lys Asn Thr Gln Arg Asn Leu Val
                115                 120                 125
```

```
Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Gly Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gly Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
450                 455                 460

Ala Ser Ala Asp Thr Lys Phe Ala Ala Thr Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

Val Asn Ala Phe Asp Gly Arg Ile Thr Ala Leu Asp Ser Lys Val Glu
        515                 520                 525

Asn Gly Met Ala Ala Gln Ala Ala His His
530                 535
```

```
<210> SEQ ID NO 69
<211> LENGTH: 537
<212> TYPE: PRT
<213> ORGANISM: Moraxella catarrhalis

<400> SEQUENCE: 69
```

| | | | | | | | | | | | | | | | |
|---|---|---|---|---|---|---|---|---|---|---|---|---|---|---|---|
| Met | Ala | Lys | Asn | Asp | Ile | Thr | Leu | Glu | Asp | Leu | Pro | Tyr | Leu | Ile | Lys |
| 1 | | | | 5 | | | | | 10 | | | | | 15 | |
| Lys | Ile | Asp | Gln | Asn | Glu | Leu | Glu | Ala | Asp | Ile | Gly | Asp | Ile | Thr | Ala |
| | | | 20 | | | | | 25 | | | | | 30 | | |
| Leu | Glu | Lys | Tyr | Leu | Ala | Leu | Ser | Gln | Tyr | Gly | Asn | Ile | Leu | Ala | Leu |
| | | 35 | | | | | 40 | | | | | 45 | | | |
| Glu | Glu | Leu | Asn | Lys | Ala | Leu | Glu | Glu | Leu | Asp | Glu | Asp | Val | Gly | Trp |
| | 50 | | | | | 55 | | | | | 60 | | | | |
| Asn | Gln | Asn | Asp | Ile | Ala | Asn | Leu | Glu | Asp | Asp | Val | Glu | Thr | Leu | Thr |
| 65 | | | | | 70 | | | | | 75 | | | | | 80 |
| Lys | Asn | Gln | Asn | Ala | Leu | Ala | Glu | Gln | Gly | Glu | Ala | Ile | Lys | Glu | Asp |
| | | | | 85 | | | | | 90 | | | | | 95 | |
| Leu | Gln | Gly | Leu | Ala | Asp | Phe | Val | Glu | Gly | Gln | Glu | Gly | Lys | Ile | Leu |
| | | | 100 | | | | | 105 | | | | | 110 | | |
| Gln | Asn | Glu | Thr | Ser | Ile | Lys | Lys | Asn | Thr | Gln | Arg | Asn | Leu | Val | Asn |
| | | | 115 | | | | | 120 | | | | | 125 | | |
| Gly | Phe | Glu | Ile | Glu | Lys | Asn | Lys | Asp | Ala | Ile | Ala | Lys | Asn | Asn | Glu |
| | | 130 | | | | | 135 | | | | | 140 | | | |
| Ser | Ile | Glu | Asp | Leu | Tyr | Asp | Phe | Gly | His | Glu | Val | Ala | Glu | Ser | Ile |
| 145 | | | | | 150 | | | | | 155 | | | | | 160 |
| Gly | Glu | Ile | His | Ala | His | Asn | Glu | Ala | Gln | Asn | Glu | Thr | Leu | Lys | Gly |
| | | | | 165 | | | | | 170 | | | | | 175 | |
| Leu | Ile | Thr | Asn | Ser | Ile | Glu | Asn | Thr | Asn | Asn | Ile | Thr | Lys | Asn | Lys |
| | | | 180 | | | | | 185 | | | | | 190 | | |
| Ala | Asp | Ile | Gln | Ala | Leu | Glu | Asn | Asn | Val | Val | Glu | Glu | Leu | Phe | Asn |
| | | 195 | | | | | 200 | | | | | 205 | | | |
| Leu | Ser | Gly | Arg | Leu | Ile | Asp | Gln | Lys | Ala | Asp | Ile | Asp | Asn | Asn | Ile |
| 210 | | | | | 215 | | | | | 220 | | | | | |
| Asn | Asn | Ile | Tyr | Glu | Leu | Ala | Gln | Gln | Gln | Asp | Gln | His | Ser | Ser | Asp |
| 225 | | | | | 230 | | | | | 235 | | | | | 240 |
| Ile | Lys | Thr | Leu | Lys | Lys | Asn | Val | Glu | Glu | Gly | Leu | Leu | Glu | Leu | Ser |
| | | | | 245 | | | | | 250 | | | | | 255 | |
| Gly | His | Leu | Ile | Asp | Gln | Lys | Thr | Asp | Ile | Ala | Gln | Asn | Gln | Ala | Asn |
| | | | 260 | | | | | 265 | | | | | 270 | | |
| Ile | Gln | Asp | Leu | Ala | Thr | Tyr | Asn | Glu | Leu | Gln | Asp | Gln | Tyr | Ala | Gln |
| | | 275 | | | | | 280 | | | | | 285 | | | |
| Lys | Gln | Thr | Glu | Ala | Ile | Asp | Ala | Leu | Asn | Lys | Ala | Ser | Ser | Glu | Asn |
| | 290 | | | | | 295 | | | | | 300 | | | | |
| Thr | Gln | Asn | Ile | Glu | Asp | Leu | Ala | Ala | Tyr | Asn | Glu | Leu | Gln | Asp | Ala |
| 305 | | | | | 310 | | | | | 315 | | | | | 320 |
| Tyr | Ala | Lys | Gln | Gln | Thr | Glu | Ala | Ile | Asp | Ala | Leu | Asn | Lys | Ala | Ser |
| | | | | 325 | | | | | 330 | | | | | 335 | |
| Ser | Glu | Asn | Thr | Gln | Asn | Ile | Glu | Asp | Leu | Ala | Ala | Tyr | Asn | Glu | Leu |
| | | | 340 | | | | | 345 | | | | | 350 | | |
| Gln | Asp | Ala | Tyr | Ala | Lys | Gln | Gln | Thr | Glu | Ala | Ile | Asp | Ala | Leu | Asn |
| | | 355 | | | | | 360 | | | | | 365 | | | |
| Lys | Ala | Ser | Ser | Glu | Asn | Thr | Gln | Asn | Ile | Ala | Lys | Asn | Gln | Ala | Asp |
| | 370 | | | | | 375 | | | | | 380 | | | | |

```
Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
            405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
            435                 440                 445

Asp Lys Leu Ile Thr Ala Asn Lys Thr Ala Ile Asp Ala Asn Lys Ala
            450                 455                 460

Ser Ala Asp Thr Lys Phe Ala Thr Ala Asp Ala Ile Thr Lys Asn
465                 470                 475                 480

Gly Asn Ala Ile Thr Lys Asn Ala Lys Ser Ile Thr Asp Leu Gly Thr
            485                 490                 495

Lys Val Asp Gly Phe Asp Ser Arg Val Thr Ala Leu Asp Thr Lys Val
            500                 505                 510

Asn Ala Phe Asp Gly Arg Ile Thr Ala Leu Asp Ser Lys Val Glu Asn
            515                 520                 525

Gly Met Ala Ala Gln Ala Ala His His
            530                 535

<210> SEQ ID NO 70
<211> LENGTH: 536
<212> TYPE: PRT
<213> ORGANISM: Moraxella catarrhalis

<400> SEQUENCE: 70

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220
```

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
        290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
        370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
        450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

Val Asn Ala Phe Asp Gly Arg Ile Thr Ala Leu Asp Ser Lys Val Glu
            515                 520                 525

Asn Gly Met Ala Ala Gln Ala Ala
        530                 535

<210> SEQ ID NO 71
<211> LENGTH: 519
<212> TYPE: PRT
<213> ORGANISM: Moraxella catarrhalis

<400> SEQUENCE: 71

Met Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
            35                  40                  45

Glu Glu Leu Asn Lys Ala Leu Glu Glu Leu Asp Glu Asp Val Gly Trp

```
            50                  55                  60
Asn Gln Asn Asp Ile Ala Asn Leu Glu Asp Asp Val Glu Thr Leu Thr
 65                  70                  75                  80

Lys Asn Gln Asn Ala Leu Ala Glu Gln Gly Glu Ala Ile Lys Glu Asp
                     85                  90                  95

Leu Gln Gly Leu Ala Asp Phe Val Glu Gly Gln Gly Lys Ile Leu
                100                 105                 110

Gln Asn Glu Thr Ser Ile Lys Lys Asn Thr Gln Arg Asn Leu Val Asn
                115                 120                 125

Gly Phe Glu Ile Glu Lys Asn Lys Asp Ala Ile Ala Lys Asn Asn Glu
                130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Ile Thr Lys Asn Lys
                180                 185                 190

Ala Asp Ile Gln Ala Leu Glu Asn Asn Val Val Glu Glu Leu Phe Asn
                195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
                260                 265                 270

Ile Gln Asp Leu Ala Thr Tyr Asn Glu Leu Gln Asp Gln Tyr Ala Gln
                275                 280                 285

Lys Gln Thr Glu Ala Ile Asp Ala Leu Asn Lys Ala Ser Ser Glu Asn
                290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
                340                 345                 350

Gln Asp Ala Tyr Ala Lys Gln Gln Thr Glu Ala Ile Asp Ala Leu Asn
                355                 360                 365

Lys Ala Ser Ser Glu Asn Thr Gln Asn Ile Ala Lys Asn Gln Ala Asp
                370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
                420                 425                 430

Thr Leu Thr Lys Asn Gln Asn Thr Leu Ile Glu Lys Asp Lys Glu His
                435                 440                 445

Asp Lys Leu Ile Thr Ala Asn Lys Thr Ala Ile Asp Ala Asn Lys Ala
                450                 455                 460

Ser Ala Asp Thr Lys Phe Ala Ala Thr Ala Asp Ala Ile Thr Lys Asn
465                 470                 475                 480
```

```
Gly Asn Ala Ile Thr Lys Asn Ala Lys Ser Ile Thr Asp Leu Gly Thr
            485                 490                 495

Lys Val Asp Gly Phe Asp Ser Arg Val Thr Ala Leu Asp Thr Lys Ala
        500                 505                 510

Ser His His His His His
        515

<210> SEQ ID NO 72
<211> LENGTH: 275
<212> TYPE: PRT
<213> ORGANISM: Artificial
<220> FEATURE:
<223> OTHER INFORMATION: fusion protein LVL735 (protein)

<400> SEQUENCE: 72

Met Lys Tyr Leu Leu Pro Thr Ala Ala Ala Gly Leu Leu Leu Leu Ala
1               5                   10                  15

Ala Gln Pro Ala Met Ala Ile Gln Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
50                  55                  60

Glu Pro Gln Ile Val His Phe Asp Ala Val Asn Leu Asp Lys Gly
65                  70                  75                  80

Leu Tyr Val Tyr Pro Glu Pro Lys Arg Tyr Ala Arg Ser Val Arg Gln
            85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
            115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Val Ser Glu Leu Leu Gln
            165                 170                 175

Ala Ser Ala Pro Tyr Lys Ala Asp Val Glu Leu Cys Val Tyr Ser Thr
        180                 185                 190

Asn Glu Thr Thr Asn Cys Thr Gly Gly Lys Asn Gly Ile Ala Ala Asp
        195                 200                 205

Ile Thr Thr Ala Lys Gly Tyr Val Lys Ser Val Thr Thr Ser Asn Gly
    210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
            245                 250                 255

Cys Lys Gly Thr Asp Ala Ser Leu Phe Pro Ala Asn Phe Cys Gly Ser
            260                 265                 270

Val Thr Gln
        275

<210> SEQ ID NO 73
<211> LENGTH: 253
<212> TYPE: PRT
<213> ORGANISM: Artificial
```

```
<220> FEATURE:
<223> OTHER INFORMATION: PE-PilA fusion protein without signal peptide

<400> SEQUENCE: 73

Ile Gln Lys Ala Glu Gln Asn Asp Val Lys Leu Ala Pro Pro Thr Asp
1               5                   10                  15

Val Arg Ser Gly Tyr Ile Arg Leu Val Lys Asn Val Asn Tyr Tyr Ile
            20                  25                  30

Asp Ser Glu Ser Ile Trp Val Asp Asn Gln Glu Pro Gln Ile Val His
        35                  40                  45

Phe Asp Ala Val Val Asn Leu Asp Lys Gly Leu Tyr Val Tyr Pro Glu
    50                  55                  60

Pro Lys Arg Tyr Ala Arg Ser Val Arg Gln Tyr Lys Ile Leu Asn Cys
65                  70                  75                  80

Ala Asn Tyr His Leu Thr Gln Val Arg Thr Asp Phe Tyr Asp Glu Phe
                85                  90                  95

Trp Gly Gln Gly Leu Arg Ala Ala Pro Lys Lys Gln Lys Lys His Thr
            100                 105                 110

Leu Ser Leu Thr Pro Asp Thr Thr Leu Tyr Asn Ala Ala Gln Ile Ile
            115                 120                 125

Cys Ala Asn Tyr Gly Glu Ala Phe Ser Val Asp Lys Lys Gly Gly Thr
        130                 135                 140

Lys Lys Ala Ala Val Ser Glu Leu Leu Gln Ala Ser Ala Pro Tyr Lys
145                 150                 155                 160

Ala Asp Val Glu Leu Cys Val Tyr Ser Thr Asn Glu Thr Thr Asn Cys
                165                 170                 175

Thr Gly Gly Lys Asn Gly Ile Ala Ala Asp Ile Thr Thr Ala Lys Gly
            180                 185                 190

Tyr Val Lys Ser Val Thr Thr Ser Asn Gly Ala Ile Thr Val Lys Gly
            195                 200                 205

Asp Gly Thr Leu Ala Asn Met Glu Tyr Ile Leu Gln Ala Thr Gly Asn
        210                 215                 220

Ala Ala Thr Gly Val Thr Trp Thr Thr Thr Cys Lys Gly Thr Asp Ala
225                 230                 235                 240

Ser Leu Phe Pro Ala Asn Phe Cys Gly Ser Val Thr Gln
            245                 250
```

METHODS OF BOOSTING IMMUNE RESPONSES

CROSS-REFERENCE TO RELATED APPLICATIONS

This application is filed pursuant to 35 U.S.C. § 371 as a United States National Phase Application of International Application No. PCT/EP2018/071860 filed Aug. 13, 2018 which claims priority from U.S. 62/545,010 filed Aug. 14, 2017 and U.S. 62/633,263 filed Feb. 21, 2018.

SEQUENCE LISTING

A sequence listing filed herewith, entitled "PB66391 US SEQLST", prepared Feb. 5, 2019, 293 KB in size, is hereby incorporated by reference herein.

FIELD OF THE INVENTION

The present invention relates to immunogenic compositions, such as vaccines, comprising immunogenic polypeptides from *Haemophilus influenzae* and *Moraxella catarrhalis*, for use in a method of boosting an immune response and methods of treatment using same. More particularly, the invention relates to use of such immunogenic compositions in methods of treating or preventing exacerbation of chronic obstructive pulmonary disease.

BACKGROUND OF THE INVENTION

Chronic Obstructive Pulmonary Disease (COPD), a common preventable disease, is characterised by persistent airflow limitation that is usually progressive. The airflow limitation is associated with an enhanced chronic inflammatory response in the airways and lungs to noxious particles of gases. The most important environmental risk factor for COPD is tobacco smoking, even though other factors, such as occupational exposure, may also contribute to the development of the disease [1]. It is a multi-component disease that manifests as an accelerated decline in lung function, with symptoms such as breathlessness on physical exertion, deteriorating health status and exacerbations.

The prevalence of COPD is increasing: worldwide, COPD (GOLD grade II and above) affects 10.1±4.8% of the population ≥40 years of age [2]. COPD is most prevalent in adults/elderly with a history of smoking [3]. It is the fourth leading cause of chronic morbidity and mortality in the United States and the first in terms of disease burden in China. Recent papers report that in 2015, COPD ranked third among the global age-standardised death rates for both sexes, with about 3.2 million patients dying of the disease [4].

Acute exacerbations and comorbidities contribute to the overall disease severity in individual COPD patients. An acute exacerbation of COPD (AECOPD) is an acute event characterised by a worsening of the patient's respiratory symptoms that is beyond normal day-to-day variations and leads to a change in medication [1]. AECOPD increases morbidity and mortality, leading to faster decline in lung function, poorer functional status [5].

The lungs are known to be colonised with different strains of bacteria [6, 7]. In COPD patients, acquisition of new bacterial strains is believed to be an important cause of AECOPD [8]. Although estimates vary widely, Non-Typeable *Haemophilus influenzae* (NTHi) appears to be the main bacterial pathogen associated with AECOPD (11-38%), followed by *Moraxella catarrhalis* (Mcat) (3-25%) and *Streptococcus pneumoniae* (4-9%) [[7, 8, 9, 10, 11, 12, 13, 14, 15, 16, 17, 18 and 18A].

A wide range of pharmacologic (such as inhaled corticosteroids, bronchodilators, phosphodiesterase inhibitors, theophyllines, long-term antibiotics and mucolytics) and non-pharmacologic (such as lung volume reduction surgery, home oxygen, ventilatory support and pulmonary rehabilitation) interventions exist to manage or treat COPD, some with a positive impact on the AECOPD rate. However, these approaches may not be completely effective, even when targeted and used optimally. Therefore, there exists a need for further treatment regimens to manage or treat COPD, particularly AECOPD.

SUMMARY OF THE INVENTION

The present Inventors have discovered improved regimens for boosting an immune response against Non-Typeable *Haemophilus influenzae* and *Moraxella catarrhalis*. Particularly the treatment regimens are vaccine regimens, for example, prime-boost regimens.

Thus, in a first aspect of the invention there is provided an immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof, for use in a method of boosting a pre-existing immune response against non-typeable *Haemophilus influenzae* and *Moraxella catarrhalis* in a subject, the method comprising the step of administering the immunogenic composition to the subject in an amount sufficient to elicit an immune response, particularly in an amount sufficient to elicit a further or additional, immune response relative to the pre-existing immune response.

Particularly, the subject has a previous history of Chronic Obstructive Pulmonary Disease (COPD). Yet more particularly, the subject has a previous history of moderate and severe Acute Exacerbation of Chronic Obstructive Pulmonary Disease (AECOPD). Thus, in certain embodiments the immunogenic composition is for use in a method of treating or preventing an acute exacerbation of chronic obstructive pulmonary disease (AECOPD), the method comprising boosting a pre-existing immune response against non-typeable *Haemophilus influenzae* and *Moraxella catarrhalis* by administering the immunogenic composition to the subject in an amount sufficient to elicit an immune response, particularly in an amount sufficient to elicit a further or additional, immune response relative to the pre-existing immune response. In an embodiment, the acute exacerbation of chronic obstructive pulmonary disease (AECOPD) is associated with a bacterial infection. However, this is not intended to imply that a bacterial infection must have been identified by testing, for example, by bacterial culture.

Generally, the pre-existing immune response has been elicited by prior administration of at least two doses, for example a first dose and a second dose, of an immunogenic composition comprising PD, PE, PilA and UspA2 or fragments thereof. For example, the pre-existing immune response may result from primary immunisation of the subject with at least two doses of a vaccine comprising PD, PE, PilA, and UspA2, or fragments thereof.

In certain embodiments the immunogenic composition is administered six to 12 months after administration of the first of the at least two doses of vaccine. Subsequently, the immunogenic composition may be administered at regular intervals, for example, every six to 12 months. Thus, in one embodiment the immunogenic composition can be administered six to 12 months after administration of the first of the at least two doses of vaccine, and again six to 12 months later, for example on the anniversary of the first of the at least two doses of vaccine.

Particularly, the step of administering the immunogenic composition to the subject elicits an immune response against PD, PE, PilA and UspA2. More particularly, the immune response against PD, PE, PilA and UspA2 is sufficient to induce protective or therapeutic immunity against non-typeable *Haemophilus influenzae* or *Moraxella catarrhalis*. Yet more particularly, the immune response against PD, PE, PilA and UspA2 is sufficient to induce protective or therapeutic immunity against non-typeable *Haemophilus influenzae* and *Moraxella catarrhalis*. Still yet more particularly, the immune response against PD, PE, PilA and UspA2 is sufficient to reduce the frequency of AECOPD.

Particularly, the subject is a suitable mammal, preferably a human. The subject may be an adult human, for example, aged between 18 and 80 years of age, 18 and 70, 18 and 50, 18 and 40 or between 50 and 70 or between 40 and 80 years of age. In some embodiments, the immunogenic composition is for use in a subject having a smoking history, for example, a smoking history of at least ten pack years. For example, 1 pack-year is equal to smoking 20 cigarettes (1 pack) per day for 1 year, or 40 cigarettes per day for half a year, or 10 cigarettes per day for 2 years. The number of pack years is calculated by multiplying the number of packs of cigarettes smoked per day by the number of years the person has smoked (since 1 pack is 20 cigarettes, this may also be calculated as follows: average number of cigarettes smoked per day multiplied by the number of years and divided by 20). In other embodiments, the immunogenic composition is for use in a subject having cystic fibrosis, for example, diagnosed by genetic test, blood test and/or sweat test.

BRIEF DESCRIPTION OF FIGURES

FIG. 3(*a*) provides a three-dose regime with primary vaccination taking place at Day 1, Day 61 and Day 181. Annual booster doses may be provided following completion of the three-dose vaccination regime. FIG. 3(*b*) provides a three-dose regime with primary vaccination taking place at Day 1, Day 61 with a booster at Day 361. Annual booster doses may be provided following completion of the three-dose vaccination regime.

DESCRIPTION OF THE INVENTION

COPD is characterised by progressive worsening of airflow limitation and a decline in pulmonary function and is complicated by acute exacerbations (AECOPD) which are transient and apparently stochastic periods of increased COPD symptoms requiring additional medical treatment and often hospitalisation. An "acute exacerbation" has its normal meaning in the art, referring to an abrupt or sudden worsening of a patient's COPD symptoms beyond their usual normal day-to-day variations and state and requiring urgent care. Acute exacerbations may be triggered by a variety of stimuli including exposure to pathogens, such as bacteria and viruses, inhaled irritants such as smoke from cigarettes, allergens, or pollutants. COPD patients with a documented history of one or more acute exacerbations have an increased risk of subsequent exacerbations, particularly bacterial exacerbation. The term "bacterial exacerbation" refers to an acute exacerbation associated with a positive bacterial pathogen on routine culture (for example, *Haemophilus* influenza and/or *Moraxella catarrhalis*) or a total aerobic CFU (colony forming units) count greater than or equal to $10^7$ cells. Without wishing to be bound by theory, the treatment regimens reduce the risk of such bacterial exacerbations happening by inducing an immune response in a subject characterised by an increase in the level of antibodies that prevent or reduce the risk of infection by and/or colonisation of the subject, particularly the subject's airways, with *Haemophilus* influenza and *Moraxella catarrhalis*. In so doing, the present invention reduces the frequency, duration or severity of an acute exacerbation of COPD and/or reduces the frequency, duration or severity of one or more symptoms of an acute exacerbation of COPD. A reduction in frequency, duration or severity of acute exacerbation or one or more symptoms of acute exacerbation may be measured by clinical observation by an ordinarily skilled doctor or clinician. A reduction in frequency, duration or severity is determined relative to the frequency, duration or severity of an acute exacerbation or symptom in the same subject not treated according to the methods of the present invention. Suitable clinical observations by an ordinarily skilled clinician may include objective measures of lung function, as well as the frequency with which medical intervention is required. Subjective self-evaluation by the subject may also be used as a measure, for example, using an FDA-recognized subject reported outcome tool or the Exacerbations from Pulmonary Disease Tool (EXACT-PRO).

Figure 1A:
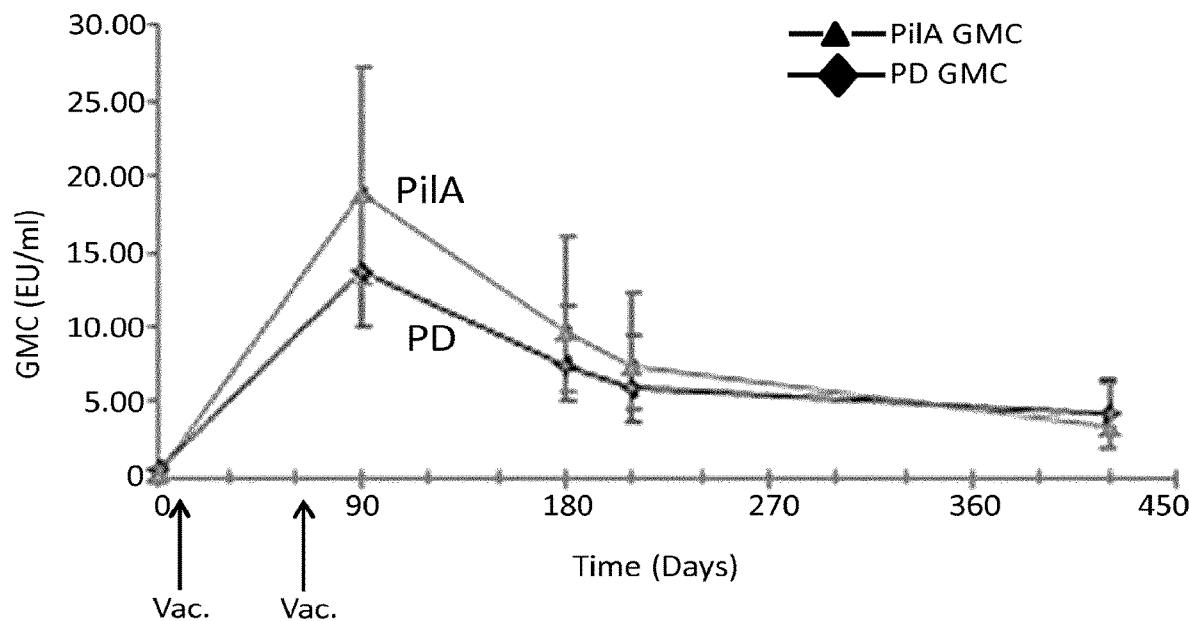
FIG. 1*a*. shows the immune response to PD and PilA following immunisation with two doses of an AS01E adjuvanted NTHi immunogenic composition comprising PD and PE-PilA fusion protein administered intramuscularly according to a 0, 2-month schedule in current and former smokers (50-70 years old) in a Phase 1 clinical trial (NTHi-003).
Figure 1B:
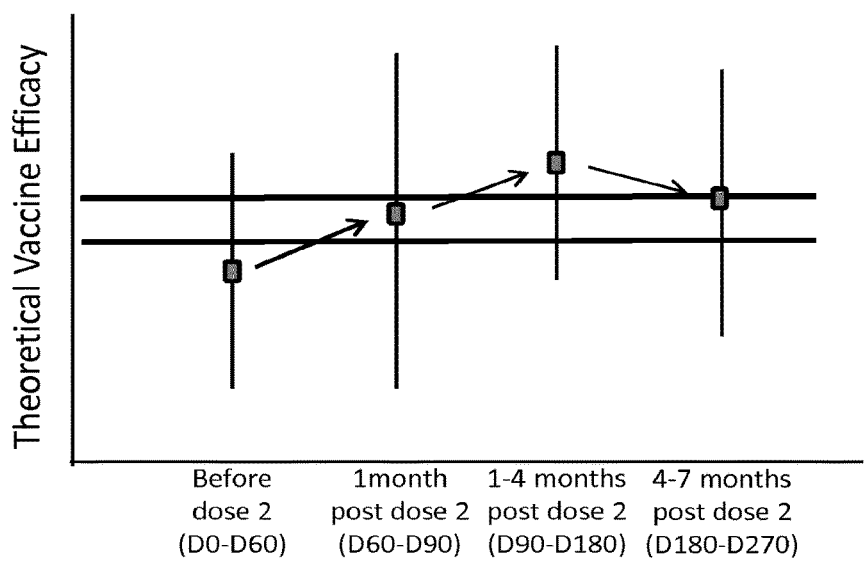
FIG. 1*b*. shows a theoretical trend in vaccine efficacy based on interim analysis of clinical trial data. A theoretical trend for a lower vaccine efficacy 7 month post-vaccination compared to 4 months post-vaccination is shown.

Following immunisation schedules using two-doses of an investigational NTHi-Mcat vaccine, the inventors have observed that the antibody response in subjects peaks one month post administration of the $2^{nd}$ dose (FIG. 1a). Following this peak, a decline in the level of vaccine specific antibodies is observed 4 to 5 months after administration of the $2^{nd}$ dose at which point the level of circulating antibodies stabilises during the next months (FIG. 1a; Example 4 Table 9). A theoretical trend for a lower vaccine efficacy 7 month post-vaccination compared to 4 months post-vaccination was predicted (FIG. 1b). Whilst persistence of the response is observed up to 1 year after administration of the $2^{nd}$ dose, the inventors have developed improved treatment regimens comprising a third, or a booster dose of vaccine to improve the immune response providing increased levels of antibody compared to a two-dose immunisation schedule.

Thus, the present invention relates to immunogenic compositions for use in methods of boosting pre-existing immune responses against non-typeable *Haemophilus influenzae* and/or *Moraxella catarrhalis*. As a result, the treatment regimens reduce or inhibit acute exacerbation of chronic obstructive pulmonary disease (AECOPD) in a subject. Particularly suitable immunogenic compositions are described in the following pages and generally will comprise (i) protein D from *Haemophilus influenzae* (PD) or a fragment thereof, (ii) Protein E from *Haemophilus influenzae* (PE) or a fragment thereof, (iii) pilin A from *Haemophilus influenza* (PilA) or a fragment thereof and (iv) Ubiquitous surface protein A2 from *Moraxella catarrhalis* (UspA2) or a fragment thereof. Particularly the treatment regimens improve the humoral immune response and more particularly, increase or "boost" the level of anti-PD, anti-PE, anti-PilA and anti-UspA2 antibodies.

In a first embodiment of the present invention there is provided an immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus influenza* (PilA) or a fragment thereof and (iv) Ubiquitous surface protein A2 from *Moraxella catarrhalis* (UspA2) or a fragment thereof, for use in a method of boosting a pre-existing immune response against non-typeable *Haemophilus influenzae* and *Moraxella catarrhalis* in a subject, the method comprising the step of administering the immunogenic composition to the subject in an amount sufficient to elicit an immune response. More particularly, there is provided an immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus influenza* (PilA) or a fragment thereof and (iv) Ubiquitous surface protein A2 from *Moraxella catarrhalis* (UspA2) or a fragment thereof, for use in a method of treating or preventing an acute exacerbation of chronic obstructive pulmonary disease (AECOPD) in a subject, the method comprising boosting a pre-existing immune response against non-typeable *Haemophilus influenzae* and *Moraxella catarrhalis* by administering the immunogenic composition to the subject in an amount sufficient to elicit an immune response. More particularly to increase the pre-existing immune response.

The term "pre-existing immunity" refers to a subject that has previously been exposed to a particular antigen or antigens and thus has a detectable serum antibody titer against the antigen(s) of interest. In contrast, the term "naive" refers to a subject that has not been previously exposed to a particular antigen or antigens and does not have a detectable serum antibody titer against the antigen(s) of interest. The presence of pre-existing immunity may be verified, if necessary, by conventional methods known in the art. For example, a subject with pre-existing immunity, in other words a "seropositive subject", can be identified by the presence of antibodies or other immune markers in serum, which indicate prior exposure to a particular antigen. In relation to the present invention, the pre-existing immunity results from prior vaccination or "priming" of the subject against *Haemophilus influenzae* and *Moraxella catarrhalis* by sequential administration of at least two doses, a first dose and a second dose, of an immunogenic composition comprising PD, PE, PilA and UspA2, or fragments thereof. Priming typically involves administration of the first dose of an immunogenic composition comprising PD, PE, PilA and UspA2, or fragments thereof at a first time point, followed by administration of the second dose of an immunogenic composition comprising PD, PE, PilA and UspA2, or fragments thereof at a second time point. The first and second time points will generally be separated by at least two weeks, and typically by approximately 8 weeks (two months or 60 days). If the first time point may is referred to as 'Day 1', a second time point 60 days later will be referred to as 'Day 61'.

Following such priming, a third dose of an immunogenic composition is administered to improve, stimulate or expand the pre-existing immune response, for example, to stimulate an immune response that results in an increase in the levels of anti-PD, anti-PE, anti-PilA and anti-UspA2 antibodies, by way of non-limiting example, IgA, IgG or IgE. When the third dose is administered around a year after the first dose, it may generally be referred to as a booster dose. In some embodiments, the term "boost" or "boosting" is meant to include situations in which the concentration of vaccine specific antibodies such as IgG, IgG1, and IgG3 are significantly increased in treatment groups compared with corresponding placebo treatment groups. Such immune boosting may be effective in preventing or treating an acute exacerbation of chronic obstructive pulmonary disease (AECOPD) in a subject. Particularly, the third or booster dose is administered in an amount sufficient to elicit a further or additional immune response relative to, or when compared with, the pre-existing immune response.

The third dose may be administered to the patient at least six months after administration of the first dose of a vaccine, for example on or about Day 181. The third dose, in certain embodiments referred to as a booster dose, may be administered at least six, at least seven, at least eight, at least nine, at least ten, at least eleven or at least twelve months after the first dose. For example, the third dose may be administered in the range of from between six to seven months, six to eight months, six to nine months, six to 10 months, six to 11 months or six to 12 months after the first dose. For example, on or about, day 181, day 211, day 241, day 271, day 301, day 331, day 361 or day 391. Particularly, in the range of from between five months to twelve and a half (12.5) months, five and a half (5.5) to twelve and a half (12.5) months, six to twelve months, from seven to twelve months, from eight to twelve months, from nine to twelve months, from ten to twelve months or from eleven to twelve months. For example, the third dose may be administered in the range of seven to twelve and a half (12.5) months, eight to twelve and a half (12.5) months, nine to twelve and a half (12.5) months, ten to twelve and a half (12.5) months or eleven to twelve and a half (12.5) months after the first dose. Particularly in the range of from between day 166 to day 391, day 181 to day 361, day 241 to day 361, day 271 to day 361, day 301 to day 361 or day 331 to day 391, particularly day 331 to day 365.

In one embodiment the immunogenic composition (e.g. third dose) is administered six to 13 months (e.g. administered between six and 12 months) after administration of the first of the at least two doses of vaccine. For example, the immunogenic composition (e.g. third dose) may be administered six months after administration of the first of the at least two doses of vaccine. For example, the immunogenic composition (e.g. third dose) may be administered 12 months after administration of the first of the at least two doses of vaccine.

The acute exacerbation of chronic obstructive pulmonary disease (AECOPD) associated with a bacterial infection may be defined by: (a) a positive bacterial pathogen on culture of an induced or spontaneous sputum sample obtained from a subject; and/or (b) a total aerobic CFU count greater than or equal to $10^7$ bacterial cells; and/or (c) the presence of increased sputum purulence. Bacterial infection may also be determined by molecular detection, for example using polymerase chain reaction (PCR), sequencing of selected genes, particularly genes that are heterogeneous between strains of a species, such as the P2 gene of NTHi. Particularly, the bacterial exacerbation may be associated with a bacterial infection with: (a) *Haemophilus influenzae*, particularly nontypeable *Haemophilus influenzae* (NTHi), (b) *Moraxella catarrhalis* or (c) *Haemophilus influenzae*, particularly nontypeable *Haemophilus influenzae* (NTHi), and *Moraxella catarrhalis*, for example, as determined by positive bacterial culture.

The immunogenic compositions administered as the first, second and booster dose may be the same (homologous) or different (heterologous) but preferably they will comprise an immunologically effective amount of: (i) protein D from *Haemophilus influenzae* (PD) or a fragment thereof, (ii) Protein E from *Haemophilus influenzae* (PE) or a fragment thereof, (iii) pilin A from *Haemophilus influenza* (PilA) or a fragment thereof and (iv) Ubiquitous surface protein A2 from *Moraxella catarrhalis* (UspA2) or a fragment thereof. By way of non-limiting example, heterologous immunogenic compositions may differ in terms of amount of antigen, formulation, adjuvant, vector, etc. Generally, the immunogenic compositions will be the same, i.e., in terms of formulation, antigen content, excipients, etc.

In certain embodiments, the immunogenic composition is for use in a method of protecting a subject against an exacerbation of chronic obstructive pulmonary disease (COPD) associated with or caused by a bacterial infection with *Haemophilus* influenza, particularly NTHi. In certain embodiments, the immunogenic composition is for use in a method of reducing the risk of an exacerbation of chronic obstructive pulmonary disease (COPD) in a subject, particularly an exacerbation associated with or caused by a bacterial infection with *Haemophilus* influenza, particularly NTHi. In certain embodiments, the immunogenic composition is for use in a method of protecting a subject against an exacerbation of chronic obstructive pulmonary disease (COPD) associated with or caused by a bacterial infection with *Moraxella catarrhalis*. In certain embodiments, the immunogenic composition is for use in a method of protecting a subject against an exacerbation of chronic obstructive pulmonary disease (COPD) associated with or caused by a bacterial infection with *Haemophilus* influenza, particularly NTHi and *Moraxella catarrhalis*.

In certain embodiments, the immunogenic composition is for use in a method of reducing the severity of or delaying the onset of at least one symptom associated with an exacerbation of chronic obstructive pulmonary disease (COPD) associated with or caused by a bacterial infection with *Haemophilus* influenza, particularly NTHi. In certain embodiments, the immunogenic composition is for use in a method of reducing the severity of or delaying the onset of at least one symptom associated with an exacerbation of chronic obstructive pulmonary disease (COPD) associated with or caused by a bacterial infection with *Moraxella catarrhalis*. In certain embodiments, the immunogenic composition is for use in a method of reducing the severity of or delaying the onset of at least one symptom associated with an exacerbation of chronic obstructive pulmonary disease (COPD) associated with or caused by a bacterial infection with *Haemophilus* influenza, particularly NTHi and *Moraxella catarrhalis*.

The invention further provides an immunogenic composition for use in a prime-boost immunisation method to treat or prevent an exacerbation of chronic obstructive pulmonary disease (COPD) associated with a bacterial infection by *Haemophilus influenzae* and *Moraxella catarrhalis* in a subject, the method comprising the steps of:

(a) administering to a subject a first dose of the immunogenic composition; and (b) administering to the subject a second dose of the immunogenic composition; and (c) administering to the subject a third dose of the immunogenic composition; wherein the immunogenic composition comprises: (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

The subject may be any suitable mammal but preferably is a human. The subject may be an adult human, for example, aged between 18 and 40 or between 50 and 70 or between 40 and 85 years of age. The subject has a previous history of Chronic Obstructive Pulmonary Disease (COPD), particularly, a previous history of moderate and severe Acute Exacerbation of Chronic Obstructive Pulmonary Disease (AECOPD). For example, a confirmed diagnosis of COPD, categorised as moderate, severe, or very severe according to the Global Initiative for Chronic Obstructive Lung Disease (GOLD) classification. The Global Strategy for the Diagnosis, Management and Prevention of COPD prepared by GOLD state that COPD should be considered in any patient with dyspnea, chronic cough or sputum production, and/or a history of exposure to risk factors for the disease, such as tobacco smoking, occupation, or pollutants. A spirometry assessment, measuring airflow limitation, is required to establish diagnosis. The classification of airflow limitation severity in COPD outlined in the GOLD strategy is shown in Table 1.

TABLE 1

Classification of airflow limitation severity in COPD (Based on post-bronchodilator $FEV_1$) In patients with $FEV_1/FVC < 0.70$

| GOLD 1 | Mild | $FEV_1 \geq 80\%$ predicted |
|---|---|---|
| GOLD 2 | Moderate | $50\% \leq FEV_1 < 80\%$ predicted |
| GOLD 3 | Severe | $30\% \leq FEV_1 < 50\%$ predicted |
| GOLD 4 | Very Severe | $FEV_1 < 30\%$ predicted |

Figure 2:
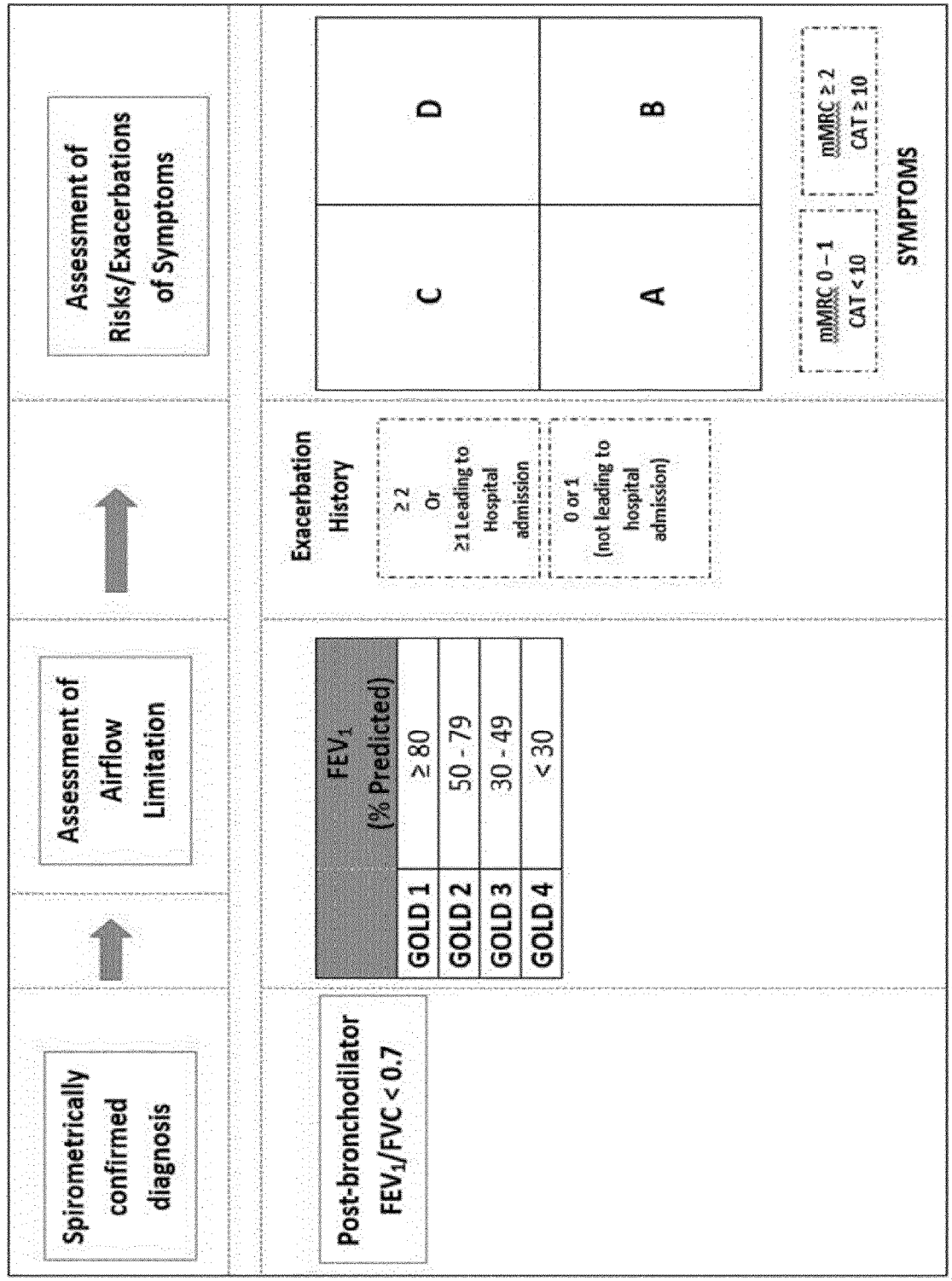
FIG. 2. shows the ABCD assessment tool.

COPD assessment also includes analysis of patient symptoms, and this can be performed using comprehensive disease-specific health status questionnaires such as the Chronic Respiratory Questionnaire (CRQ) and St. George's Respiratory Questionnaire (SGRQ). For routine practice the COPD Assessment Test (CAT™) and The COPD Control Questionnaire (The CCQ©) have been developed. The CAT™ and CCQ© tests do not categorise patients for the purpose of treatment, however for the SRGQ assessment a symptom score ≥25 may be used as the threshold for considered regular treatment for breathlessness. The equivalent threshold for the CAT™ is 10. A simple assessment of breathlessness is the Modified British Medical Research Council (mMRC) Questionnaire. According to the GOLD strategy, of the patients classified at the GOLD 2 (moderate) stage, approximately 20% may experience frequent exacerbations requiring antibiotic and/or systemic corticosteroid therapy in addition to regular maintenance therapy. The risk of exacerbations is significantly higher for patients classified as GOLD 3 (severe) and GOLD 4 (very severe). The "ABCD" assessment tool is further used to understand a COPD patient's severity of disease. This assessment combines the patient's spirometry analysis with their exacerbation history and symptom assessment to give a spirometric grade combined with an "ABCD" group. The ABCD assessment tool is shown in FIG. 2. In some embodiments, the subject has GOLD 2 (moderate), GOLD 3 (severe) or GOLD 4 (very severe) COPD status. The subject may be one that has experienced at least one (e.g. 2 or more, 3 or more) episodes of acute exacerbation in chronic obstructive pulmonary disease (AECOPD), particularly at least one (e.g. 2 or more, 3 or more) episodes of acute exacerbation in chronic obstructive pulmonary disease (AECOPD) within a period of 12 months. Yet more particularly the subject has experienced at least one (e.g. 2 or more, 3 or more) episode of acute exacerbation in chronic obstructive pulmonary disease (AECOPD) in the preceding 12 months. The subject may be a subject having bronchiectasis. In certain embodiments the subject has experienced an acute exacerbation of chronic obstructive pulmonary disease (AECOPD) and failed to achieve resolution of symptoms after antibiotic therapy.

The skilled person will also understand that the invention is also applicable to methods of treatment. The invention therefore also provides: a method for the treatment or prevention of an acute exacerbation of chronic obstructive pulmonary disease (AECOPD) in a subject comprising administering to said subject an immunogenic composition comprising an immunologically effective amount of (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

The present invention also provides a method of immunising a subject against *Haemophilus* influenza and *Moraxella catarrhalis* infection to treat or prevent an exacerbation of chronic obstructive pulmonary disease (COPD) comprising, administering to the subject an immunogenic composition comprising an immunologically effective amount of (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

The present invention also provides a method of inducing an immune response to *Haemophilus* influenza and *Moraxella catarrhalis* in a subject to treat or prevent an exacerbation of chronic obstructive pulmonary disease (COPD), the method comprising administering to the subject an immunogenic composition comprising an immunologically effective amount of (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

The invention further provides a prime-boost immunization method for inducing an immune response to *Haemophilus influenzae* and *Moraxella catarrhalis* to treat or prevent an exacerbation of chronic obstructive pulmonary disease (COPD), the method comprising the steps of:

(a) administering to a subject a first immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof; and (b) administering to the subject a second immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof; and (c) administering to the subject a third immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof; wherein at least one of the first, second or third immunogenic compositions. In some embodiments, the first, second and third immunogenic compositions are heterologous compositions. In other embodiments, the first, second and third immunogenic compositions are homologous compositions.

In certain embodiments there is provided a vaccination protocol comprising administering a first, a second and a third immunologically effective dose of an immunogenic composition to a subject, wherein the third dose of the immunogenic composition is administered at least 6 months after administration of the first dose of the immunogenic composition, wherein the immunogenic composition comprises (i) protein D from *Haemophilus influenzae* (PD) or a fragment thereof, (ii) Protein E from *Haemophilus influen-* zae (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

In certain embodiments, the method is a method of protecting a subject against an exacerbation of chronic obstructive pulmonary disease (COPD) associated with or caused by a bacterial infection with *Haemophilus* influenza, particularly NTHi. In certain embodiments, the method is a method of protecting a subject against an exacerbation of chronic obstructive pulmonary disease (COPD) associated with or caused by a bacterial infection with *Moraxella catarrhalis*. In certain embodiments, the method is a method of protecting a subject against an exacerbation of chronic obstructive pulmonary disease (COPD) associated with or caused by a bacterial infection with *Haemophilus* influenza, particularly NTHi and *Moraxella catarrhalis*.

In certain embodiments, the method is a method of reducing the severity of or delaying the onset of at least one symptom associated with an exacerbation of chronic obstructive pulmonary disease (COPD) associated with or caused by a bacterial infection with *Haemophilus* influenza, particularly NTHi. In certain embodiments, the method is a method of reducing the severity of or delaying the onset of at least one symptom associated with an exacerbation of chronic obstructive pulmonary disease (COPD) associated with or caused by a bacterial infection with *Moraxella catarrhalis*. In certain embodiments, the method is a method of reducing the severity of or delaying the onset of at least one symptom associated with an exacerbation of chronic obstructive pulmonary disease (COPD) associated with or caused by a bacterial infection with *Haemophilus* influenza, particularly NTHi and *Moraxella catarrhalis*.

In other embodiments, the present invention provides immunogenic compositions and vaccines for use in the manufacture of a medicament for treating or preventing an exacerbation of chronic obstructive pulmonary disease (COPD) associated with a bacterial infection in a subject caused by *Haemophilus* influenza, particularly NTHi and *Moraxella catarrhalis*.

Figure 3A:
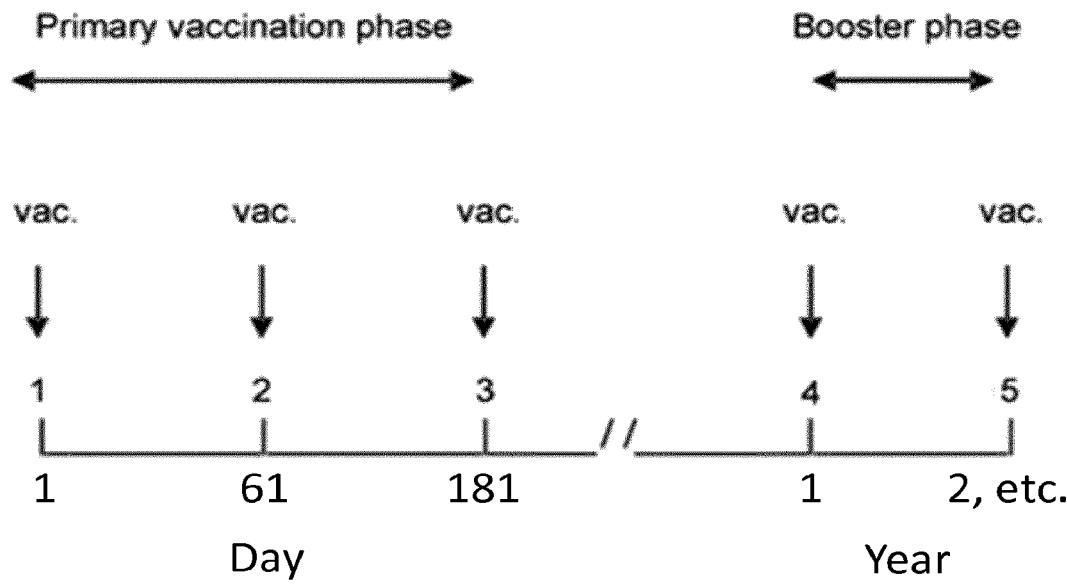
FIG. 3. exemplifies treatment regimens of the present invention.
Figure 3B:
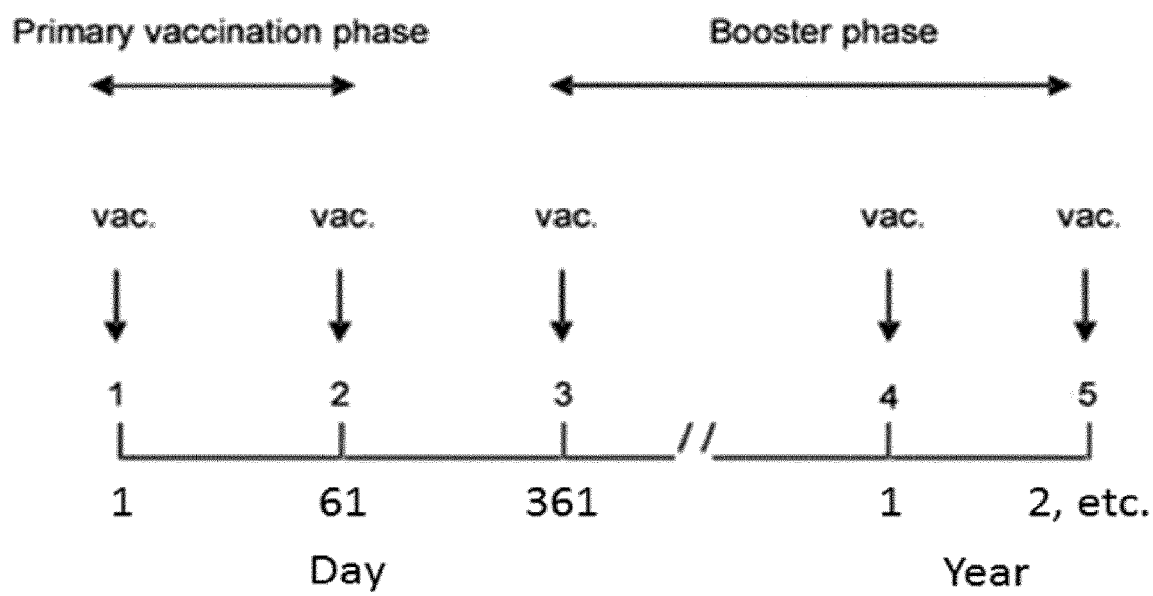

By way of non-limiting example, FIGS. 3(a) and 3(b) provide a schematic of generalised regimens of the invention.

Immunogenic Compositions

The term "immunogenic composition" broadly refers to any composition that may be administered to elicit an immune response, such as an antibody or cellular immune response, against an antigen present in the composition. Thus, compositions of the invention are immunogenic. When the immunogenic compositions prevent, ameliorate, palliate or eliminate disease from the subject, then such compositions may be referred to as a vaccine. Vaccines according to the invention may either be prophylactic (i.e. to prevent infection) or therapeutic (i.e. to treat infection), but will typically be prophylactic. In certain embodiments, the immunogenic composition is a vaccine. The term "antigen" refers to a substance that, when administered to a subject, elicits an immune response directed against the substance. In the context of the present invention, PD, PE, PilA, UspA2 (including fragments thereof) are antigens. Preferably the PD, PE, Pila and UspA2 antigens are recombinant antigens prepared or manufactured using recombinant DNA technology. Particularly, when administered to a subject the immunogenic composition elicits an immune response directed against PD, PE, PilA, UspA2. Particularly the immune response directed against PD, PE, PilA, UspA2 is protective, that is, it can prevent or reduce infection or colonisation caused by *Haemophilus influenzae* and/or *Moraxella catarrhalis*.

Protein D (PD)

The immunogenic composition for use in the invention comprises protein D or an immunogenic fragment thereof from *Haemophilus* influenza. Protein D (PD) is a highly conserved 42 kDa surface lipoprotein found in all *Haemophilus influenzae*, including nontypeable *Haemophilus influenzae*. Inclusion of this protein in the immunogenic composition may provide a level of protection against *Haemophilus influenzae* related otitis media [19]. Suitable amino acid sequences for PD include, for example, the protein D sequence from FIG. 9 of EP 0594610 (FIG. 9a and 9b together, 364 amino acids) and as described in WO91/18926 or WO00/56360 (disclosed herein as SEQ ID NOs: 1 and 2. Other suitable proteins may be encoded by, for example, Genbank accession numbers: X90493 (SEQ ID NO:3), X90489 (SEQ ID NO:4), X90491 (SEQ ID NO:5), Z35656 (SEQ ID NO:6), Z35657 (SEQ ID NO:7), Z35658 (SEQ ID NO:8), M37487 (SEQ ID NO:9).

One skilled in the art will further recognise that immunogenic compositions may comprise polypeptides having sequence identity to Protein D provided that such polypeptides are capable of generating an immune response to Protein D, for example, they comprise one or more epitopes of protein D. Thus, immunogenic compositions may comprise an isolated immunogenic polypeptide having sequence identity of at least 70%, 80%, 85%, 90%, 91%, 92%, 93%, 94%, 95%, 96%, 97%, 98%, 99%, or 100% to SEQ ID NO:1 wherein the isolated immunogenic polypeptide is capable of eliciting an immune response against SEQ ID NO:1, particularly an immune response that results in the formation of antibodies that bind to SEQ ID NO:1.

Protein E (PE)

Protein E is an outer membrane lipoprotein with adhesive properties. It plays a role in the adhesion/invasion of non-typeable *Haemophilus influenzae* (NTHi) to epithelial cells [20, 21, 22]. It is highly conserved in both encapsulated *Haemophilus influenzae* and non-typeable *Haemophilus influenzae* and has a conserved epithelial binding domain [23]. Thirteen different point mutations have been described in different *Haemophilus* species when compared with *Haemophilus influenzae* Rd as a reference strain. Its expression is observed on both logarithmic growing and stationary phase bacteria (WO2007/084053). Protein E is also involved in human complement resistance through binding vitronectin. [24]. PE, by the binding domain PKRYARSVRQ YKILNCANYH LTQVR (SEQ ID NO:10, corresponding to amino acids 84-108 of SEQ ID NO:11), binds vitronectin which is an important inhibitor of the terminal complement pathway [24].

Protein E from *H. influenza* (also referred to as: "protein E", "Prot E" and "PE") may consist of or comprise the amino acid sequence of SEQ ID NO:11 (corresponding to SEQ ID NO:4 of WO2012/139225A1). One skilled in the art will further recognise that immunogenic compositions may comprise polypeptides having sequence identity to Protein E provided that such polypeptides are capable of generating an immune response to Protein E, for example, they comprise one or more epitopes of Protein E. Thus, immunogenic compositions may comprise an isolated immunogenic polypeptide having sequence identity of at least 70%, 80%, 85%, 90%, 91%, 92%, 93%, 94%, 95%, 96%, 97%, 98%, 99%, or 100% to SEQ ID NO:11 wherein the isolated immunogenic polypeptide is capable of eliciting an immune response against SEQ ID NO:11, particularly an immune response that results in the formation of antibodies that bind to SEQ ID NO:11. The immunogenicity of PE polypeptides may be measured as described in WO2012/139225A1 herein incorporated by reference.

Pilin A (PilA)

Pilin A (PilA) is likely the major pilin subunit of *H. influenzae* Type IV Pilus (Tfp) involved in twitching motility [25]. NTHi PilA is a conserved adhesin expressed in vivo. It has been shown to be involved in NTHi adherence, colonization and biofilm formation [26]. PilA may consist of or comprise the protein sequence of SEQ ID NO:12 (corresponding to SEQ ID NO. 58 of WO2012/139225A1). One skilled in the art will further recognise that immunogenic compositions may comprise polypeptides having sequence identity to Pilin A provided that such polypeptides are capable of generating an immune response to PilA, for example, they comprise one or more epitopes of PilA. Thus, immunogenic compositions may comprise an isolated immunogenic polypeptide having sequence identity of at least 70%, 80%, 85%, 90%, 91%, 92%, 93%, 94%, 95%, 96%, 97%, 98%, 99%, or 100% to SEQ ID NO:12 wherein the isolated immunogenic polypeptide is capable of eliciting an immune response against SEQ ID NO:12, particularly an immune response that results in the formation of antibodies that bind to SEQ ID NO:12. The immunogenicity of PilA polypeptides may be measured as described in WO2012/139225A1 herein incorporated by reference.

Ubiquitous Surface Protein A2 (UspA2)

As used herein "UspA2" means Ubiquitous surface protein A2 from *Moraxella catarrhalis* (*M. catarrhalis*; Mcat). Ubiquitous surface protein A2 is a trimeric autotransporter identified in *Moraxella catarrhalis* that appears as a lollipop-shared structure in electron micrographs [27]. It is composed of an N-terminal head, followed by a stalk which ends in an amphipathic helix and a C-terminal membrane domain [27]. UspA2 contains a very well conserved domain [28], which is recognized by a monoclonal antibody that was shown protective upon passive transfer in a mouse *Moraxella catarrhalis* challenge model [29]. UspA2 has been shown to interact with host structures and extracellular matrix proteins like fibronectin [30] and laminin [31] suggesting it can play a role at an early stage of *Moraxella catarrhalis* infection. UspA2 also seems to be involved in the ability of *Moraxella catarrhalis* to resist the bactericidal activity of normal human serum [32]. It (i) binds the complement inhibitor C4bp, enabling *Moraxella catarrhalis* to inhibit the classical complement system, (ii) prevents activation of the alternative complement pathway by absorbing C3 from serum and (iii) interferes with the terminal stages of the complement system, the Membrane Attack Complex (MAC), by binding the complement regulator protein vitronectin [33]. UspA2 may consist of or comprise the amino acid sequence of SEQ ID NO:13 from ATCC 25238 as well as sequences with at least or exactly 63%, 66%, 70%, 72%, 74%, 75%, 77%, 80%, 84%, 85%, 90%, 95%, 96%, 97%, 98%, 99% or 100% identity, over the entire length, to SEQ ID NO: 13.

UspA2 as described in SEQ ID NO:13 contains a signal peptide at amino acids 1 to 29 (SEQ ID NO:14), a laminin binding domain at amino acids 30 to 177 (SEQ ID NO: 15), a fibronectin binding domain at amino acids 165 to 318 (SEQ ID NO:16) (Tan et al. JID 192: 1029-38 (2005)), a C3 binding domain at amino acids 30 to 539 (SEQ ID NO:17) (WO2007/018463) or a fragment of amino acids 30 to 539 of SEQ ID NO: 10, for example, amino acids 165 to 318 of SEQ ID NO: 1 (Hallström T et al. J. Immunol. 186: 3120-3129 (2011)), an amphipathic helix at amino acids 519 to 564 (SEQ ID NO:18) or amino acids 520-559 (SEQ ID NO:19), (identified using different prediction methods) and a C terminal anchor domain at amino acids 576 to 630 (SEQ ID NO:20) (Brooks et al., Infection & Immunity, 76(11), 5330-5340 (2008)). UspA2 amino acid differences have been described for various *Moraxella catarrhalis* species. See for example, J Bacteriology 181(13):4026-34 (1999), Infection and Immunity 76(11):5330-40 (2008) and PLoS One 7(9):e45452 (2012).

UspA2 may consist of or comprise an amino acid sequence that differs from SEQ ID NO:13 at any one or more amino acid selected from the group consisting of: AA (amino acid) 30 to 298, AA 299 to 302, AA 303 to 333, AA 334 to 339, AA 349, AA 352 to 354, AA 368 to 403, AA 441, AA 451 to 471, AA 472, AA474 to 483, AA 487, AA 490, AA 493, AA 529, AA 532 or AA 543. UspA2 may consist of or comprise an amino acid sequence that differs from SEQ ID NO:13 in that it contains an amino acid insertion in comparison to SEQ ID NO:13. UspA2 may consists of or comprise an amino acid sequence that differs from SEQ ID NO:13 at any one of the amino acid differences in SEQ ID NO: 21 through SEQ ID NO: 57. For example, SEQ ID NO:13 may contain K instead of Q at amino acid 70, Q instead of G at amino acid 135 and/or D instead of N at amino acid 216. Further amino acid sequences of UspA2 from 38 strains of *Moraxalla catarrhalis* are provided as SEQ ID NOs: 21 to 57. WO2015/125118A1 describes compositions comprising *Moraxella catarrhalis* (*M. catarrhalis*, Mcat) Ubiquitous surface protein A2 (UspA2).

Immunogenic Fragments

In certain embodiments, immunogenic fragments of the above proteins may also be used. As used herein the term "fragment" refers to a sequence that is a subset of another sequence. The term is used to refer to a part or portion of an intact or complete wild-type polypeptide but which comprise fewer amino acid residues than the intact or complete wild-type polypeptide. Thus, the term refers to truncated or shorter amino acid sequences corresponding to one or more regions of a wild-type or reference polypeptide and it is to be understood that as used herein, the term fragment excludes reference to the full-length or wild-type polypeptide sequence. One example of a fragment is an epitope sequence. A fragment or subsequence of an amino acid sequence can be any number of residues less than that found in the naturally occurring, or reference, polypeptide. However, it will be clear to one skilled in the art that, in the context of the present invention, any such immunogenic fragments must be capable of eliciting an immune response against the full length polypeptide, particularly an immune response that results in the formation of antibodies capable of binding to the full length polypeptide. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide.

The fragments should comprise at least n consecutive amino acids from the sequences and, depending on the particular sequence, n is 7 or more (e.g. 7, 10, 15, 20, 25, 30 or 50 or more). The fragments may comprise an amino acid sequence of from 7 amino acid residues up to 10, up to 15, up to 20, up to 30 or up to 50 consecutive amino acid residues. The fragments may comprise an amino acid sequence of more than 7 amino acid residues but less than 50, less than 40, less than 30, less than 25, less than 20, less than 15 or less than 10 consecutive amino acid residues. Preferred fragments may comprise one or more epitopes from the sequence. To the extent that such fragments are used, they will share the immunogenic properties of the naturally occurring, or reference, polypeptide, more particularly the 'immunogenic property' (or properties) in the context of the present invention, is the ability to elicit a therapeutic immune response against nontypeable *Haemophilus influenzae* or *Moraxella catarrhalis* (e.g. provide or induce a protective effect which is at least 50%, 60%, 70%, 80%, 90%, 91%, 92%, 93%, 94%, 95%, 96%, 97%, 98%, 99% or 100% of that shown by the relevant or corresponding nontypeable *Haemophilus influenzae* or *Moraxella catarrhalis* sequence referred to in the sequence listing).

It will be clear to those skilled in the art that, whilst such fragments are truncated or shorter fragments of a reference sequence, such fragments may be modified to comprise additional sequences not found in the reference polypeptide, for example, to form fusion polypeptides, include 'tag' sequences such as His tags or Glutathione S-transferase (GST) tags, linker sequences and the like. Thus, in such modified fragments the amino group of the N terminal amino acid of the fragment is not linked by a peptide bond to the carboxyl group of an amino acid to which it would be linked in the reference polypeptide from which it is derived and/or the carboxyl group of the C terminal amino acid of the fragment is not linked by a peptide bond to the amino group of an amino acid to which it would be linked in the reference polypeptide from which it is derived.

Particular immunogenic fragments of Protein D comprise or consist of at least 7, 10, 15, 20, 25, 30 or 50 contiguous amino acids of, for example, SEQ ID NO: 1 or 2. Preferably, the immunogenic fragments elicit antibodies that can bind to SEQ ID NO:1 or 2. In particular embodiments, a protein D immunogenic fragment sequence may comprise (or consist) of the protein D fragment described in EP0594610 which begins at the sequence SSHSSNMANT (SEQ ID NO:58), and lacks the 19 N-terminal amino acids from FIG. 9 of EP0594610, optionally with the tripeptide MDP from NS1 fused to the N-terminal of said protein D fragment (348 amino acids) (SEQ ID NO:2). The protein D or fragment of protein D may be lipidated or un-lipidated. Particularly, the Protein D or fragment of Protein D is un-lipidated. The immunogenic composition may comprise or consist of an immunogenic fragment of Protein D, suitably an isolated immunogenic polypeptide having at least 70%, 80%, 85%, 90%, 91%, 92%, 93%, 94%, 95%, 96%, 97%, 98%, 99%, or 100% sequence identity to SEQ ID NO:1

Particular immunogenic fragments of Protein E comprise or consist of at least 7, 10, 15, 20, 25, 30 or 50 contiguous amino acids of SEQ ID NO: 1. Preferably, the immunogenic fragments elicit antibodies that can bind to SEQ ID NO: 11. The immunogenic composition may comprise an immunogenic fragment of Protein E, suitably an isolated immunogenic polypeptide having at least 70%, 80%, 85%, 90%, 91%, 92%, 93%, 94%, 95%, 96%, 97%, 98%, 99%, or 100% sequence identity to SEQ ID NO:59 (corresponding to SEQ ID NO: 125 of WO2012/139225A1): SEQ ID NO:59: Amino acids 20-160 of Protein E.

Particular immunogenic fragments of PilA comprise or consist of at least 7, 10, 15, 20, 25, 30 or 50 contiguous amino acids of SEQ ID NO:12. Preferably, the immunogenic fragments elicit antibodies that can bind to SEQ ID NO:12. The immunogenic composition may comprise an immunogenic fragment of Pilin A, suitably an isolated immunogenic polypeptide having at least 70%, 80%, 85%, 90%, 91%, 92%, 93%, 94%, 95%, 96%, 97%, 98%, 99%, or 100% sequence identity to SEQ ID NO:60 (corresponding to Seq ID No. 127 of WO2012/139225A1): SEQ ID NO:60 Amino acids 40-149 of PilA from *H. influenzae* strain 86-028NP.

Immunogenic fragments of UspA2 comprise immunogenic fragments of at least 450 contiguous amino acids of SEQ ID NO: 1, 490 contiguous amino acids of SEQ ID NO: 13 (for example, the UspA2 fragment of MC-004 or MC-005), 511 contiguous amino acids of SEQ ID NO: 13 (for example, the UspA2 fragment of construct MC-001, MC-002, MC-003 or MC-004), 534 contiguous amino acids of SEQ ID NO: 13 (for example, the UspA2 fragment of MC-009 or MC-011) or 535 contiguous amino acids of SEQ ID NO: 13 (for example, the UspA2 fragment of MC-007, MC-008 or MC-010). The immunogenic fragments may elicit antibodies which can bind SEQ ID NO: 13.

Immunogenic fragments of UspA2 may comprise immunogenic fragments of at least 450, 490, 511, 534 or 535 contiguous amino acids of SEQ ID NO: 13. Immunogenic fragments of UspA2 may comprise immunogenic fragments of UspA2, for example any of the UspA2 constructs MC-001 (SEQ ID NO:61), MC-002 (SEQ ID NO:62), MC-003 (SEQ ID NO:63), MC-004 (SEQ ID NO:64), MC-005 (SEQ ID NO:65), MC-006 (SEQ ID NO:66), MC-007 (SEQ ID NO:67), MC-008 (SEQ ID NO:68), MC-009 (SEQ ID NO:69), MC-010 (SEQ ID NO:70) or MC-011 (SEQ ID NO:71). UspA2 constructs MC-001 to MC-011 are further described in WO2015/125118. The immunogenic fragments may elicit antibodies which can bind the full length sequence from which the fragment is derived.

In another aspect of the invention, the immunogenic composition comprises an immunogenic fragment of UspA2, suitably an isolated immunogenic polypeptide with at least 70%, 80%, 85%, 90%, 91%, 92%, 93%, 94%, 95%, 96%, 97%, 98%, 99%, or 100% to a polypeptide selected from the group consisting of MC-001 (SEQ ID NO:61), MC-002 (SEQ ID NO:62), MC-003 (SEQ ID NO:63), MC-004 (SEQ ID NO:64), MC-005 (SEQ ID NO:65), MC-006 (SEQ ID NO:66), MC-007 (SEQ ID NO:67), MC-008 (SEQ ID NO:68), MC-009 (SEQ ID NO:69), MC-010 (SEQ ID NO:70) or MC-011 (SEQ ID NO:71) for example MC009 SEQ ID NO:69 (corresponding to Seq ID NO: 69 of WO2015/125118A1). In an embodiment, an immunogenic fragment of UspA2 contains a laminin binding domain and a fibronectin binding domain. In an additional embodiment, an immunogenic fragment of UspA2 contains a laminin binding domain, a fibronectin binding domain and a C3 binding domain. In a further embodiment, an immunogenic fragment of UspA2 contains a laminin binding domain, a fibronectin binding domain, a C3 binding domain and an amphipathic helix. Immunogenicity of UspA2 polypeptides may be measured as described in WO2015/125118A1; the contents of which are incorporated herein by reference.

Fusions

The polypeptides described herein can also be provided in other forms, such as in the form of a fusion protein. Particularly, Protein E and Pilin A may be provided in the form of a fusion protein (PE-PilA). Suitable fusions are disclosed in WO2012/139225 and a preferred fusion is SEQ ID NO:72 (corresponding to sequence number 194 of WO2012/139225). Thus, the immunogenic composition may comprise a polypeptide having at least 70%, 80%, 85%, 90%, 91%, 92%, 93%, 94%, 95%, 96%, 97%, 98%, 99%, or 100% sequence identity to SEQ ID NO: 72 and/or 73.

Thus, in particular embodiments of the invention, the immunogenic composition comprises both Protein E and PilA in the form of a fusion protein, suitably an isolated immunogenic polypeptide with at least 70%, 80%, 85%, 90%, 91%, 92%, 93%, 94%, 95%, 96%, 97%, 98%, 99%, or 100% to LVL-735, wherein the signal peptide has been removed, SEQ ID NO. 73 (Corresponding to Seq ID No. 219 of WO2012/139225A1). As used herein "signal peptide" refers to a short (less than 60 amino acids, for example, 3 to 60 amino acids) polypeptide present on precursor proteins (typically at the N terminus), and which is typically absent from the mature protein. The signal peptide (sp) is typically rich in hydrophobic amino acids. The signal peptide directs the transport and/or secretion of the translated protein through the membrane. Signal peptides may also be called targeting signals, transit peptides, localization signals, or signal sequences. For example, the signal sequence may be a co-translational or post-translational signal peptide. The immunogenicity of Protein E (PE) and Pilin A (PilA) polypeptides may be measured as described in WO2012/139225A1; the contents of which are incorporated herein by reference.

Particular immunogenic compositions for use in the present invention will comprise (1) protein D, (2) a PE-PilA fusion protein and (3) UspA2. In certain embodiments, the immunogenic composition for use in the present invention comprise a recombinant UspA2 protein having at least 95% sequence identity to SEQ ID NO: 69, a recombinant Protein D protein having at least 95% sequence identity to SEQ ID NO:1 and a recombinant PE-PilA fusion protein having at least 95% sequence identity to SEQ ID NO: 72. Immunogenic compositions for use in the present invention may comprise (1) 10 μg of PD, (2) 10 μg of a PE-PilA fusion protein, (3) 10 μg of UspA2 and an (4) adjuvant, particularly AS01E. Immunogenic compositions for use in the present invention may comprise (1) 10 μg of PD, (2) 10 μg of a PE-PilA fusion protein, (3) 3.3 μg of UspA2 and an (4) adjuvant, particularly AS01E. Particularly, the PE-PilA fusion protein is the LVL735 construct (SEQ ID NO:72), as described in WO2012/139225. Particularly the UspA2 protein is the MC009 construct (SEQ ID NO:69), as described in WO2015125118. In certain embodiments, the immunogenic composition for use in the present invention comprise (1) 10 μg of a recombinant UspA2 protein of SEQ ID NO: 69, (2) 10 μg of a recombinant Protein D protein of SEQ ID NO:1 and (3) 10 μg of a recombinant PE-PilA fusion protein of SEQ ID NO: 72. In certain embodiments, the immunogenic composition for use in the present invention comprise (1) 3.3 μg of a recombinant UspA2 protein of SEQ ID NO: 69, (2) 10 μg of a recombinant Protein D protein of SEQ ID NO:1 and (3) 10 μg of a recombinant PE-PilA fusion protein of SEQ ID NO: 72. In other embodiments, the immunogenic composition for use in the present invention consists essentially of (1) 10 μg of a recombinant UspA2 protein of SEQ ID NO: 69, (2) 10 μg of a recombinant Protein D protein of SEQ ID NO:1, (3) 10 μg of a recombinant PE-PilA fusion protein of SEQ ID NO: 72 and (4) adjuvant AS01E. In other embodiments, the immunogenic composition for use in the present invention consists essentially of (1) 3.3 μg of a recombinant UspA2 protein of SEQ ID NO: 69, (2) 10 μg of a recombinant Protein D protein of SEQ ID NO:1, (3) 10 μg of a recombinant PE-PilA fusion protein of SEQ ID NO: 72 and (4) adjuvant AS01E.

Formulations

Immunogenic compositions of the invention will generally comprise a pharmaceutically acceptable carrier. A 'pharmaceutically acceptable carrier' is a carrier that does not itself induce the production of antibodies. Such carriers are well known to those of ordinary skill in the art and include, by way of non-limiting example, polysaccharides, polylactic acids, polyglycolic acids, amino acid copolymers, sucrose, trehalose, lactose, and lipid aggregates (such as oil droplets or liposomes). Immunogenic compositions may also contain diluents, such as water, saline, glycerol, and the like. Sterile pyrogen-free, phosphate-buffered physiologic saline is a typical diluent. Such compositions may also include, auxiliary substances, such as wetting or emulsifying agents, pH buffering substances, etc. The pH of the composition may be between pH 6 and pH 8, particularly about pH 7. Stable pH may be maintained by the use of a buffer. Compositions may include an antimicrobial and/or a detergent such as Tween (polysorbate).

Suitable immunogenic compositions may be in aqueous form, for example, as a solution or suspension or in a dried form, for example, lyophilised. Dried or lyophilised compositions are generally reconstituted with a liquid medium prior to injection. For lyophilisation, a stabiliser such as a sugar alcohol (e.g. mannitol) and/or a disaccharide (e.g. sucrose or trehalose) may be included. Immunogenic compositions are preferably sterile and may also be pyrogen-free. Compositions may be isotonic with respect to the subject's body.

Immunogenic compositions may be prepared in various forms, in vials or as injectables in ready filled syringes, either with or without needles. Syringes generally contain a single dose of the composition, whilst a vial may contain a single dose or multiple doses. Compositions may be prepared for pulmonary administration, for example, as a fine powder or a spray for administration using an inhaler. Other forms for administration are known to the skilled person including, by way of non-limiting example, solid dosage forms, suppositories and pessaries, compositions for nasal, aural or ocular administration such as sprays, drops, gels or powders.

Immunogenic compositions used as vaccines comprise an immunologically effective amount of antigens. The term "immunologically effective amount" refers to the amount of an antigen or antigens needed to stimulate or achieve the desired immunologic effect, particularly a cellular (T cell) response, a humoral (B cell or antibody) response, or both, as measured by standard assays known to one skilled in the art. This amount may vary depending upon the health and physical condition of the subject to be treated, age, capacity of the individual's immune system to synthesise antibodies, degree of protection desired, formulation and the like. One skilled in the art understands that the immunologically effective amount is the amount of antigen administered to a subject in a single dose and that the amount can be determined through routine trials, such as clinical or dose-ranging trials, and may fall within a range.

The amount of each individual protein antigen in a single dose of immunogenic composition will generally be from 1 μg (0.001 mg) to 120 μg (0.120 mg). The typical amount of immunogenic polypeptide or immunogenic fragment thereof from *Moraxella catarrhalis* may be expected to lie in the range of from about 1 μg (0.001 mg) to 120 μg (0.120 mg). More particularly in the range of from about 2.5 μg (0.0025 mg) to about 30 μg (0.03 mg), yet more particularly, in the range of from about 2.5 μg (0.0025 mg) to about 3.5 μg (0.0035 mg) of protein, for example about 2.5, 2.6, 2.7, 2.8, 2.9, 3.0, 3.1, 3.2, 3.3, 3.4 or 3.5 μg of protein. In general, the typical amount of the immunogenic polypeptide or immunogenic fragment thereof from *H. influenzae* may be expected to lie in the range of from about 5 μg (0.005 mg) to about 50 μg (0.05 mg) of protein, for example about 9.5, 9.6, 9.7, 9.8, 9.9, 10, 10.1, 10.2, 10.3, 10.4, 10.5, 11, 11.5, 12, 12.5, 13, 13.5, 14, 14.5, 15, 20, 25, 30, 35, 40, 45 or 50 μg of protein. The skilled person understands that in a multi-component immunogenic composition, i.e. one containing at least two different antigens, the immunologically effective amount of each antigen is likely to be different and therefore represents a proportion of the total amount of protein antigen per dose. By way of non-limiting example, an immunogenic composition that comprises an immunologically effective amount, X μg, of a first antigen and an immunologically effective amount, Y μg, of a second antigen will comprise X+Y μg of total protein antigen per dose.

Immunogenic compositions will generally comprise one or more adjuvants. As used herein, "adjuvant" means a compound or substance (or combination of compounds or substances) that, when administered to a subject in conjunction with an antigen or antigens, for example as part of an immunogenic composition or vaccine, increases or enhances the subject's immune response to the administered antigen or antigens (compared to the immune response obtained in the absence of adjuvant).

Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes. In one embodiment, the protein may be adsorbed onto aluminium phosphate. In another embodiment, the protein may be adsorbed onto aluminium hydroxide. In a third embodiment, alum may be used as an adjuvant.

Suitable adjuvant systems which promote a predominantly Th1 response include: non-toxic derivatives of lipid A, Monophosphoryl lipid A (MPL) or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen (Thoelen et al. Vaccine (1998) 16:708-14; EP 689454-B1).

AS01 is an Adjuvant System containing MPL (3-O-desacyl-4'-monophosphoryl lipid A), QS21 ((Quillaja saponaria Molina, fraction 21) Antigenics, New York, N.Y., USA) and liposomes. AS01B is an Adjuvant System containing MPL, QS21 and liposomes (50 μg MPL and 50 μg QS21). AS01E is an Adjuvant System containing MPL, QS21 and liposomes (25 μg MPL and 25 μg QS21). In one embodiment, the immunogenic composition or vaccine comprises AS01. In another embodiment, the immunogenic composition or vaccine comprises AS01B or AS01E. In a particular embodiment, the immunogenic composition or vaccine comprises AS01E.

AS02 is an Adjuvant System containing MPL and QS21 in an oil/water emulsion. AS02V is an Adjuvant System containing MPL and QS21 in an oil/water emulsion (50 μg MPL and 50 μg QS21).

AS03 is an Adjuvant System containing α-Tocopherol and squalene in an oil/water (o/w) emulsion. AS03A is an Adjuvant System containing α-Tocopherol (11.86 mg tocopherol). AS03B is an Adjuvant System containing α-Tocopherol and squalene in an o/w emulsion (5.93 mg tocopherol). AS03C is an Adjuvant System containing α-Tocopherol and squalene in an o/w emulsion (2.97 mg tocopherol). In one embodiment, the immunogenic composition or vaccine comprises AS03.

AS04 is an Adjuvant System containing MPL (50 μg MPL) adsorbed on an aluminum salt (500 μg $Al^{3+}$). In one embodiment, the immunogenic composition or vaccine comprises AS04.

A system involving the use of QS21 and 3D-MPL is disclosed in WO 94/00153. A composition wherein the QS21 is quenched with cholesterol is disclosed in WO 96/33739. An additional adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO 0226757 and WO 03507822) are also preferential inducers of a TH1 response and are suitable for use in the present invention.

Additional adjuvants are those selected from the group of metal salts, oil in water emulsions, Toll like receptor agonists, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

Possible excipients include arginine, pluronic acid and/or polysorbate. In a preferred embodiment, polysorbate 80 (for example, TWEEN (a US registered trademark) 80) is used. In a further embodiment, a final concentration of about 0.03% to about 0.06% is used. Specifically, a final concentration of about 0.03%, 0.04%, 0.05% or 0.06% polysorbate 80 (w/v) may be used.

Formulations comprising the immunogenic compositions of the invention may be adapted for administration by an appropriate route, for example, by the intramuscular, sublingual, transcutaneous, intradermal or intranasal route. Such formulations may be prepared by any method known in the art.

Kits

The invention further provides kits for use in the methods of the invention comprising a first container comprising a lyophilised immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof and a second container comprising a liquid comprising AS01E. In certain particular embodiments, the kit further comprises a buffer. In certain other embodiments, the kit further comprises instructions for use.

General

The term "comprising" encompasses "including" e.g. a composition "comprising" X may include something additional e.g. X+Y. The word "substantially" does not exclude "completely" e.g. a composition which is "substantially free" from Y may be completely free from Y. In some implementations, the term "comprising" refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), for example antigens, however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising". The term "consisting of" and variations thereof means limited to" unless expressly specified otherwise. In certain territories, the term "comprising an active ingredient consisting of" may be used in place of "consisting essentially". The term "about" in relation to a numerical value x means, for example, x±10%, x±5%, x±4%, x±3%, x±2%, x±1%. The word "substantially" does not exclude "completely" e.g. a composition which is "substantially free" from Y may be completely free from Y. Where necessary, the word "substantially" may be omitted from the definition of the invention. Where methods refer to steps of administration, for example as (a), (b), (c), etc., these are intended to be sequential, i.e., step (c) follows step (b) which is preceded by step (a). Antibodies will generally be specific for their target, i.e., they will have a higher affinity for the target than for an irrelevant control protein, such as bovine serum albumin.

Identity between polypeptides may be calculated by various algorithms. For example, the Needle program, from the EMBOSS package (Free software; EMBOSS: The European Molecular Biology Open Software Suite (2000). Trends in Genetics 16(6): 276-277) and the Gap program from the GCG® package (Accelrys Inc.) may be used. This Gap program is an implementation of the Needleman-Wunsch algorithm described in: Needleman, S. B. and Wunsch, C. D. (1970) J. Mol. Biol. 48, 443-453. The BLOSUM62 scoring matrix has been used, and the gap open and extension penalties were respectively 8 and 2.

Looking at the computed alignment, identical residues between two compared sequences can be observed. A percentage of identity can be computed by (1) calculating the number of identities divided by the length of the alignment, multiplied by 100 (for example, for the Needle program analysis), (2) calculating the number of identities divided by the length of the longest sequence, multiplied by 100, (3) calculating the number of identities divided by the length of the shortest sequence, multiplied by 100, or (4) calculating the number of identities divided by the number of aligned residues, multiplied by 100 (a residue is aligned if it is in front of another) (for example, for the Gap program analysis).

Generally, sequence identity is calculated over the entire length of the reference sequence, for example the full-length or wild-type sequence. Amino acid substitution may be conservative or non-conservative. In some embodiments, amino acid substitution is conservative. Substitutions, deletions, additions or any combination thereof may be combined in a single variant so long as the variant is an immunogenic polypeptide. Embodiments herein relating to "vaccine compositions" of the invention are also applicable to embodiments relating to "immunogenic compositions" of the invention, and vice versa.

All references or patent applications cited within this patent specification are incorporated by reference herein.

Aspects of the Invention

The following clauses describe additional embodiments of the invention:

Embodiment 1

An immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus influenza* (PilA) or a fragment thereof and (iv) Ubiquitous surface protein A2 from *Moraxella catarrhalis* (UspA2) or a fragment thereof, for use in a method of boosting a pre-existing immune response against non-typeable *Haemophilus influenzae* (NTHi) and *Moraxella catarrhalis* (Mcat) in a subject, wherein the pre-existing immune response has been elicited by previous administration of at least two doses of a vaccine comprising PD, PE, PilA and UspA2, the method comprising the step of administering the immunogenic composition to the subject in an amount sufficient to elicit an immune response in the subject against PD, PE, PilA and UspA2, particularly in an amount sufficient to elicit a further or additional, immune response against PD, PE, PilA and UspA2 relative to the pre-existing immune response.

Embodiment 2

The immunogenic composition for use of Embodiment 1, wherein the subject has a previous history of Chronic Obstructive Pulmonary Disease (COPD).

Embodiment 3

The immunogenic composition for use of Embodiment 2, wherein the subject has a previous history of moderate and severe Acute Exacerbation of Chronic Obstructive Pulmonary Disease (AECOPD).

Embodiment 4

The immunogenic composition for use of Embodiment 2 or 3 wherein the immunogenic composition is administered six to 12 months after administration of the first of the at least two doses of vaccine.

Embodiment 5

The immunogenic composition for use of Embodiment 4 wherein the immunogenic composition is subsequently administered every 12 months on the anniversary of administration of the first of the at least two doses of vaccine.

Embodiment 6

The immunogenic composition for use of any preceding Embodiment, wherein the immune response against PD, PE, PilA and UspA2 is sufficient to induce protective or therapeutic immunity against non-typeable *Haemophilus influenzae* (NTHi) and *Moraxella catarrhalis* (Mcat).

Embodiment 7

The immunogenic composition for use of any preceding Embodiment, wherein the immune response against PD, PE, PilA and UspA2 is sufficient to reduce the frequency of AECOPD.

Embodiment 8

The immunogenic composition for use of Embodiment 6 or 7, wherein the subject is a human.

Embodiment 9

The immunogenic composition for use of Embodiment 8, wherein the subject is an adult human aged between 18 and 40 or between 50 and 70 or between 40 and 80 years of age.

Embodiment 10

The immunogenic composition for use of Embodiment 9, wherein the subject has a smoking history of at least ten pack years.

Embodiment 11

The immunogenic composition for use of any preceding Embodiment wherein the UspA2 is at least 63%, 66%, 70%, 72%, 74%, 75%, 77%, 80%, 84%, 85%, 90%, 95%, 96%, 97%, 98%, 99% or 100% identical, over the entire length, to SEQ ID NO: 13.

Embodiment 12

The immunogenic composition for use of any preceding Embodiment wherein the UspA2 consists essentially of an immunogenic fragment of UspA2 selected from the group consisting of amino acids 30-540 of SEQ ID NO. 13 (SEQ ID NO: 61, 62, 63 or 64), amino acids 31-540 of SEQ ID NO: 13 (SEQ ID NO: 71), amino acids 30-519 of SEQ ID NO: 13 (SEQ ID NO: 65 or 66), amino acids 30-564 of SEQ ID NO: 13 (SEQ ID NO: 67 or 68) and amino acids 31-564 of SEQ ID NO: 13 (SEQ ID NO: 69 or 70).

Embodiment 13

The immunogenic composition for use of any preceding Embodiment wherein PE and PilA are present as a fusion protein, particularly SEQ ID NO:72 or SEQ ID NO:73.

Embodiment 14

The immunogenic composition for use of any preceding Embodiment wherein the immunogenic composition comprises UspA2 (SEQ ID NO: 69), Protein D (SEQ ID NO:1) and a PE-PilA fusion protein (SEQ ID NO: 72).

Embodiment 15

The immunogenic composition for use of any preceding Embodiment further comprising an adjuvant, particularly the adjuvant AS01E.

Embodiment 16

The immunogenic composition for use of Embodiment 14, comprising (1) 10 μg of PD, (2) 10 μg of a PE-PilA fusion protein, (3) 10 μg of UspA2 and (4) adjuvant AS01E.

Embodiment 17

The immunogenic composition for use of Embodiment 14 comprising, (1) 10 μg of PD, (2) 10 μg of a PE-PilA fusion protein, (3) 3.3 μg of UspA2 and (4) adjuvant AS01E.

Embodiment 18

A vaccination protocol comprising administering a first, a second and a third immunologically effective dose of an immunogenic composition to a subject, wherein the third dose of the immunogenic composition is administered at least 6 months after administration of the first dose of the immunogenic composition, wherein the immunogenic composition comprises (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

The following clauses also describe additional embodiments of the invention:

Embodiment 1a

A method of boosting a pre-existing immune response against non-typeable *Haemophilus influenzae* and *Moraxella catarrhalis* in a subject, the method comprising the step of administering an immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof to the subject in an amount sufficient to elicit a further or additional, immune response relative to the pre-existing immune response.

Embodiment 2a

The method according to Embodiment 1a wherein the pre-existing immune response has been elicited by prior administration of at least two doses of the immunogenic composition comprising (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

Embodiment 3a

The method according to Embodiment 1a or 2a, wherein the subject has a previous history of Chronic Obstructive Pulmonary Disease (COPD).

Embodiment 4a

The method according to Embodiment 3a, wherein the subject has a previous history of moderate and severe Acute Exacerbation of Chronic Obstructive Pulmonary Disease (AECOPD).

Embodiment 5a

The method according to Embodiment 2a, 3a or 4a wherein the immunogenic composition is administered six to 13 months (e.g. administered between six and 12 months; administered at six months; or administered at 12 months) after administration of the first of the at least two doses of vaccine.

Embodiment 6a

The method according to Embodiment 5a wherein the immunogenic composition is subsequently administered every 12 months on the anniversary of administration of the first of the at least two doses of vaccine.

Embodiment 7a

The method according to any preceding Embodiment 1a to 6a, wherein the further or additional immune response is sufficient to induce protective or therapeutic immunity against non-typeable *Haemophilus influenzae* (NTHi) and *Moraxella catarrhalis* (Mcat).

Embodiment 8a

The method according to any preceding Embodiment 1a to 7a, wherein the immune response is against PD, PE, PilA and UspA2 and is sufficient to reduce the frequency of AECOPD.

Embodiment 9a

The method according to Embodiment 7a or 8a, wherein the subject is a human.

Embodiment 10a

The method according to Embodiment 9a, wherein the subject is an adult human aged between 18 and 40 or between 50 and 70 or between 40 and 80 years of age.

Embodiment 11a

The method according to Embodiment 9a, wherein the subject has a smoking history of at least ten pack years.

Embodiment 12a

The method according to any preceding Embodiment 1a to 11a wherein the UspA2 is at least 63%, 66%, 70%, 72%, 74%, 75%, 77%, 80%, 84%, 85%, 90%, 95%, 96%, 97%, 98%, 99% or 100% identical, over the entire length, to SEQ ID NO: 13.

Embodiment 13a

The method according to any preceding Embodiment 1a to 12a wherein the UspA2 consists essentially of an immunogenic fragment of UspA2 selected from the group consisting of amino acids 30-540 of SEQ ID NO. 13 (SEQ ID NO: 61, 62, 63 or 64), amino acids 31-540 of SEQ ID NO: 13 (SEQ ID NO: 71), amino acids 30-519 of SEQ ID NO: 13 (SEQ ID NO: 65 or 66), amino acids 30-564 of SEQ ID NO: 13 (SEQ ID NO: 67 or 68) and amino acids 31-564 of SEQ ID NO: 13 (SEQ ID NO: 69 or 70).

Embodiment 14a

The method according to any preceding Embodiment 1a to 13a wherein PE and PilA are present as a fusion protein, particularly SEQ ID NO:72 or SEQ ID NO:73.

Embodiment 15a

The method according to any preceding Embodiment 1a to 14a wherein the immunogenic composition comprises UspA2 (SEQ ID NO: 69), Protein D (SEQ ID NO:1) and a PE-PilA fusion protein (SEQ ID NO: 72).

Embodiment 16a

The method according to any preceding Embodiment 1a to 15a further comprising an adjuvant, particularly the adjuvant AS01E.

Embodiment 17a

The method according to Embodiment 15a wherein the immunogenic composition comprises (1) 10 µg of PD, (2) 10 µg of a PE-PilA fusion protein, (3) 10 µg of UspA2 and (4) adjuvant AS01E.

Embodiment 18a

The method according to Embodiment 15a wherein the immunogenic composition comprises (1) 10 µg of PD, (2) 10 µg of a PE-PilA fusion protein, (3) 3.3 µg of UspA2 and (4) adjuvant AS01E.

Embodiment 19a

A vaccination protocol comprising administering a first, a second and a third immunologically effective dose of an immunogenic composition to a subject, wherein the third dose of the immunogenic composition is administered at least 6 months after administration of the first dose of the immunogenic composition, wherein the immunogenic composition comprises (i) protein D from *Haemophilus influenzae* (PD) or a fragment thereof, (ii) Protein E from *Haemophilus influenzae* (PE) or a fragment thereof, (iii) pilin A from *Haemophilus* influenza (PilA) or a fragment thereof and (iv) Ubiquitous surface protein A2 from *Moraxella catarrhalis* (UspA2) or a fragment thereof.

Embodiment 20a

The vaccination protocol according to Embodiment 19a wherein the immunogenic composition comprises (1) 10 µg of PD, (2) 10 µg of a PE-PilA fusion protein, (3) 10 µg of UspA2 and (4) adjuvant AS01E.

Embodiment 21a

The vaccination protocol according to Embodiment 19a wherein the immunogenic composition comprises (1) 10 µg of PD, (2) 10 µg of a PE-PilA fusion protein, (3) 3.3 µg of UspA2 and (4) adjuvant AS01E.

Embodiment 22a

The vaccination protocol according to Embodiment 20a or 21a wherein the immune response against PD, PE, PilA and UspA2 is sufficient to induce protective or therapeutic immunity against non-typeable *Haemophilus influenzae* (NTHi) and *Moraxella catarrhalis* (Mcat).

Embodiment 23a

The vaccination protocol according to Embodiment 20a, 21a or 22a wherein the immune response against PD, PE, PilA and UspA2 is sufficient to reduce the frequency of AECOPD.

Embodiment 24a

The vaccination protocol according to Embodiment 23a wherein the subject is a human.

Embodiment 25a

The vaccination protocol according to Embodiment 24a wherein the subject is an adult human aged between 18 and 40 or between 50 and 70 or between 40 and 80 years of age.

Embodiment 26a

The vaccination protocol according to Embodiment 25a wherein the subject has a smoking history of at least ten pack years.

In order that this invention may be better understood, the following examples are set forth. These examples are for purposes of illustration only, and are not to be construed as limiting the scope of the invention in any manner.

EXAMPLES

Example 1: Immunogenicity of PD, PE and PilA in Human Adults

An NTHi multi-component investigational vaccine was prepared based on a combination of three selected conserved surface proteins from NTHi presented as two vaccine antigens: (1) a free recombinant protein D (PD) and (2) a recombinant fusion of protein E and Pilin A (PE-PilA). The vaccine was presented as a lyophilized cake to be reconstituted with AS01E. After preparation, the appropriate injection volume (0.5 mL) of each vaccine dose was administered intramuscularly in the deltoid muscle of the non-dominant arm. An isotonic saline solution (0.9% NaCl) was used as placebo. The study vaccine was adjuvanted with AS01E. AS01E is an Adjuvant System containing 25 µg each of 3-O-desacyl-4'-monophosphoryl lipid A (MPL; GSK Vaccines, Rixensart, Belgium), Quillaja *saponaria* Molina fraction 21 (QS-21; Licensed by GSK from Antigenics Inc, a wholly owned subsidiary of Agenus Inc., a Delaware, USA corporation) and liposome.

Figure 4A:
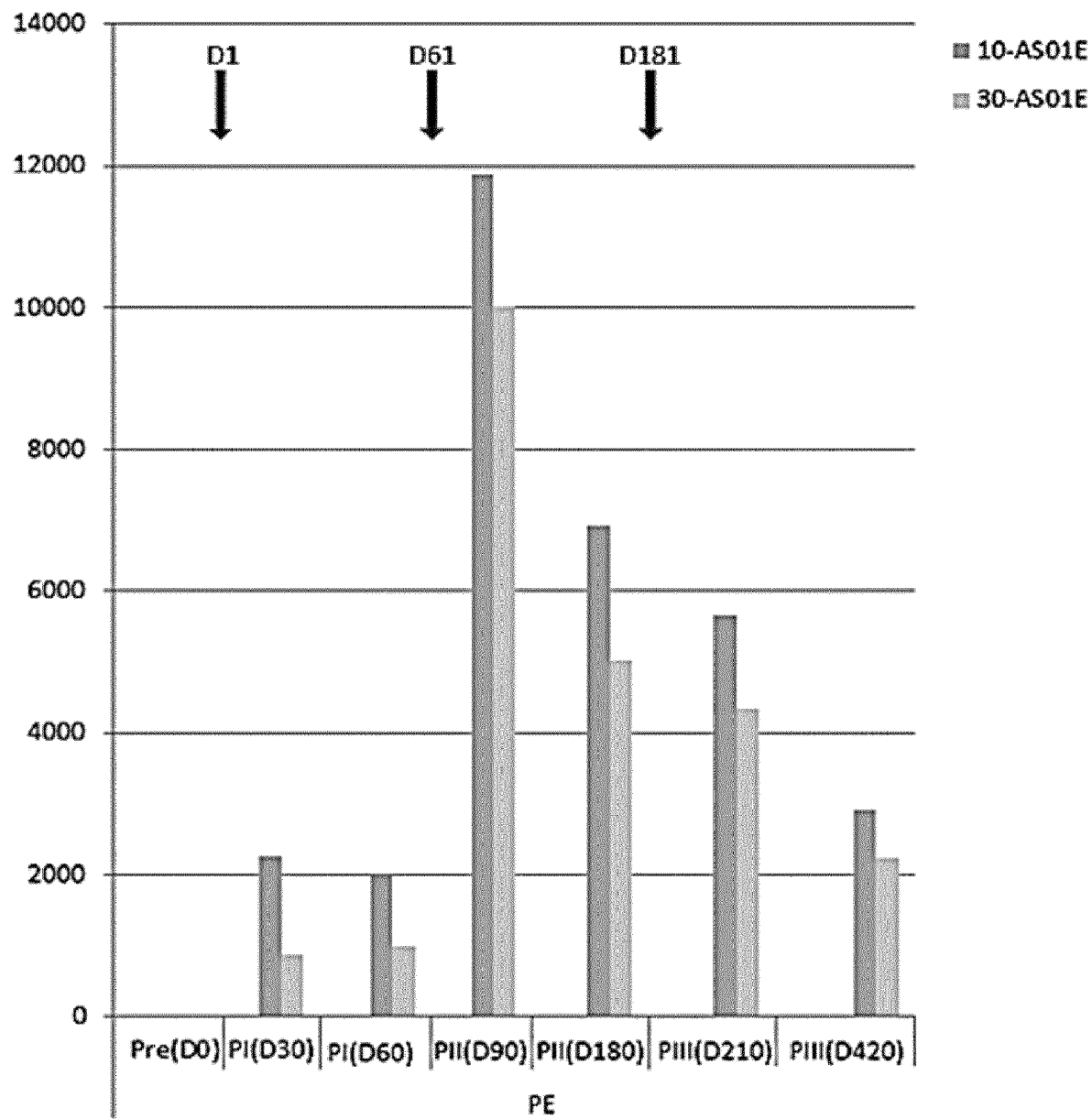
FIG. 4. Geometric mean concentrations of anti-PE (FIG. 4A), anti-PilA (FIG. 4B) and anti-PD (FIG. 4C) in participants who received 2 doses of NTHi vaccine (AS01E adjuvanted immunogenic composition comprising PD and PE-PilA fusion protein) at either 10 µg or 30 µg antigen/dose adjuvanted with AS01E; PRE, pre-Dose 1; PI(D30), 30 days post-Dose 1; PI(D60), pre-Dose 2; PII(D90), 30 days post-Dose 2; PII(D180), pre-Dose 3; PIII(D210), 30 days post-Dose 3; PIII(D420), 8 months post-Dose 3 in a Phase 1 clinical trial (NTHi-003) in current and former smokers (50-70 years old).
Figure 4B:
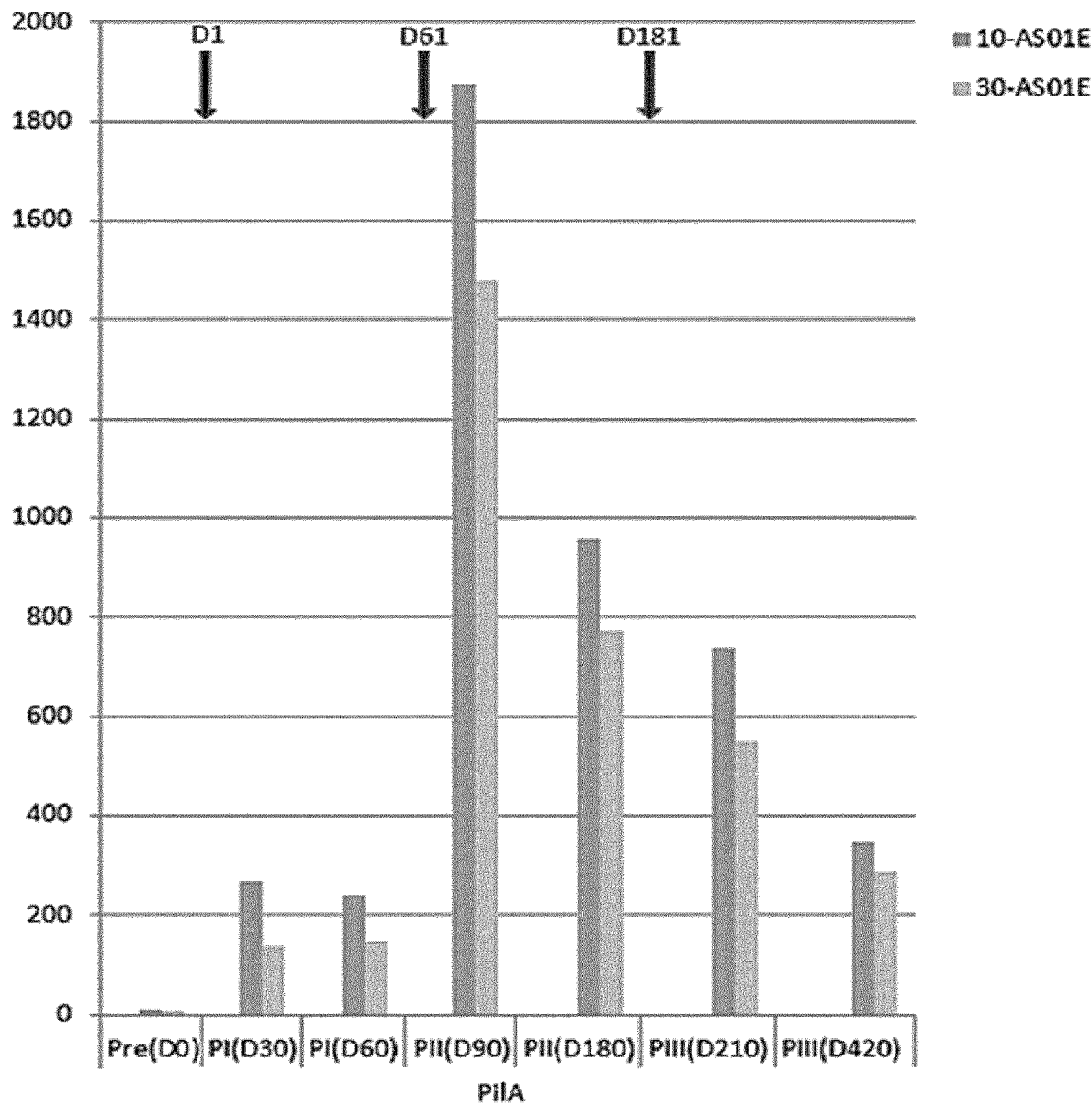
Figure 4C:
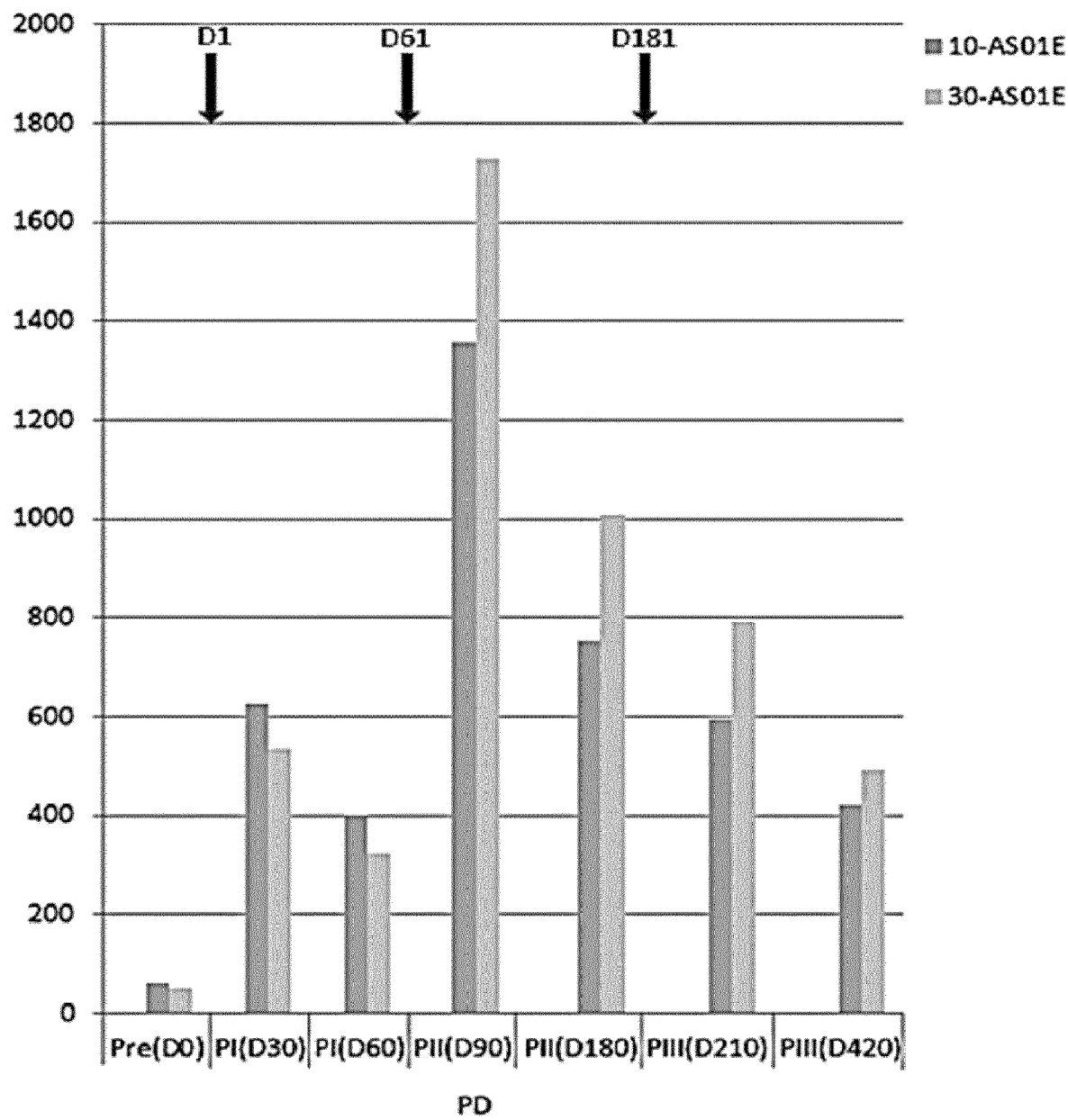
Figure 5A:
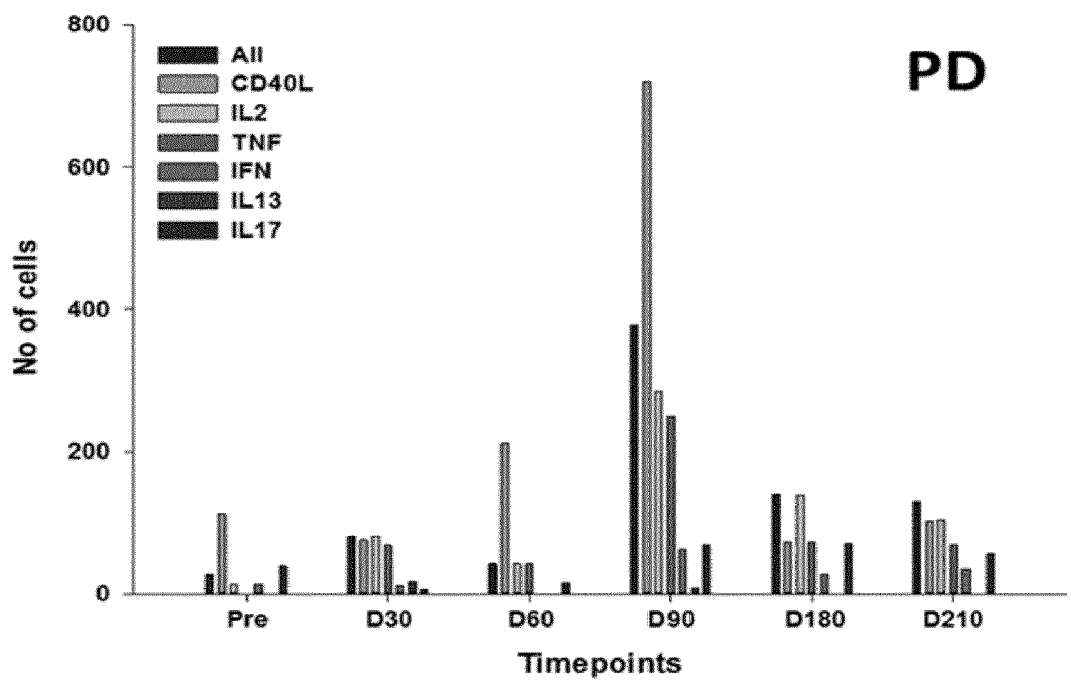
FIG. 5. Number of PD (FIG. 5A), PE (FIG. 5B) and PilA (FIG. 5C) specific CD4+ T-cells expressing the following markers: All (1st bar), CD40L (2nd bar), IL-2 (3rd bar), TNF-α (4th bar), IFN-γ (5th bar), IL-13 (6th bar) and IL-17 (7th bar) prior and after each vaccination with the 10-AS01E-adjuvanted formulations in a Phase 1 clinical trial (NTHi-003) in current and former smokers (50-70 years old).
Figure 5B:
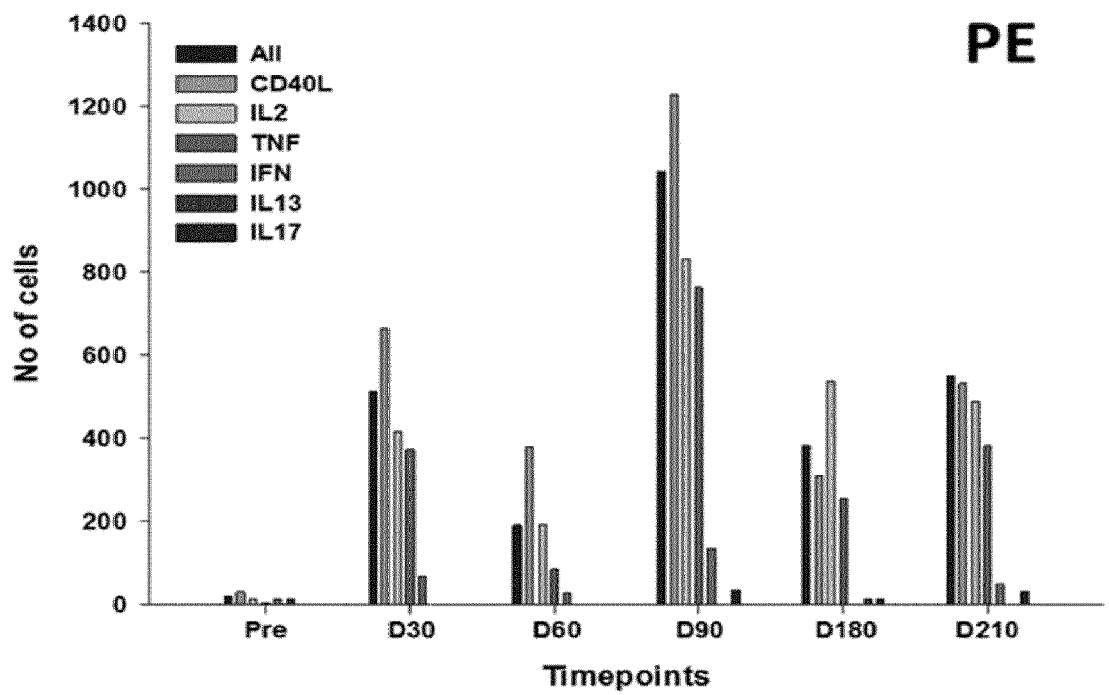
Figure 5C:
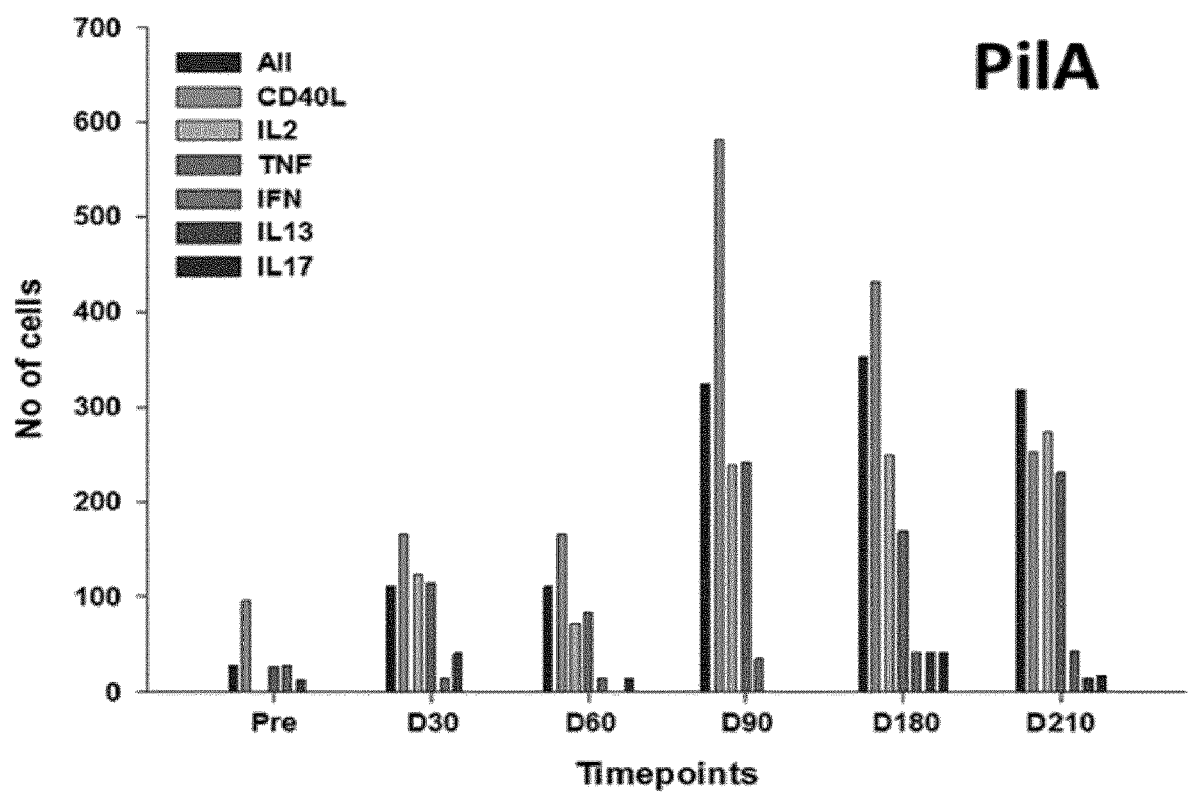
Figure 6A:
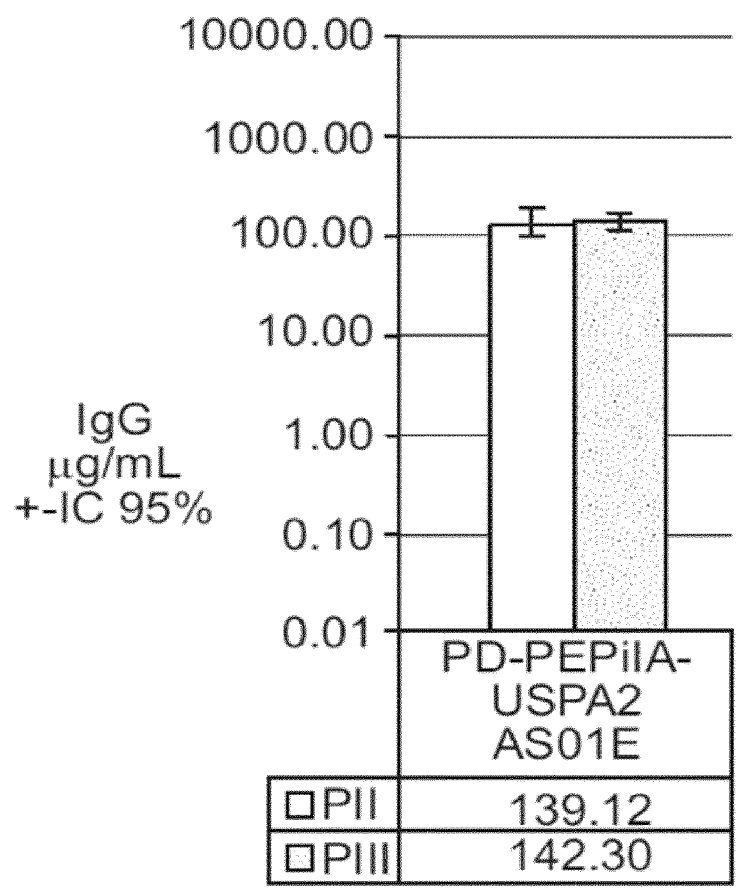
FIG. 6. The IgG responses induced against UspA2, PD, PE and PilA in mice by tetravalent NTHi-Mcat (PD-PEPilA-UspA2) vaccine are shown in FIG. 6A (UspA2), FIG. 6B (PD, protein D), FIG. 6C (PE, protein E), FIG. 6D (PilA) and FIG. 6E (PE, PilA and PD) respectively. No major impact of the addition of UspA2 on PD and PEPilA immunogenicity in AS01E was observed.
Figure 6B:
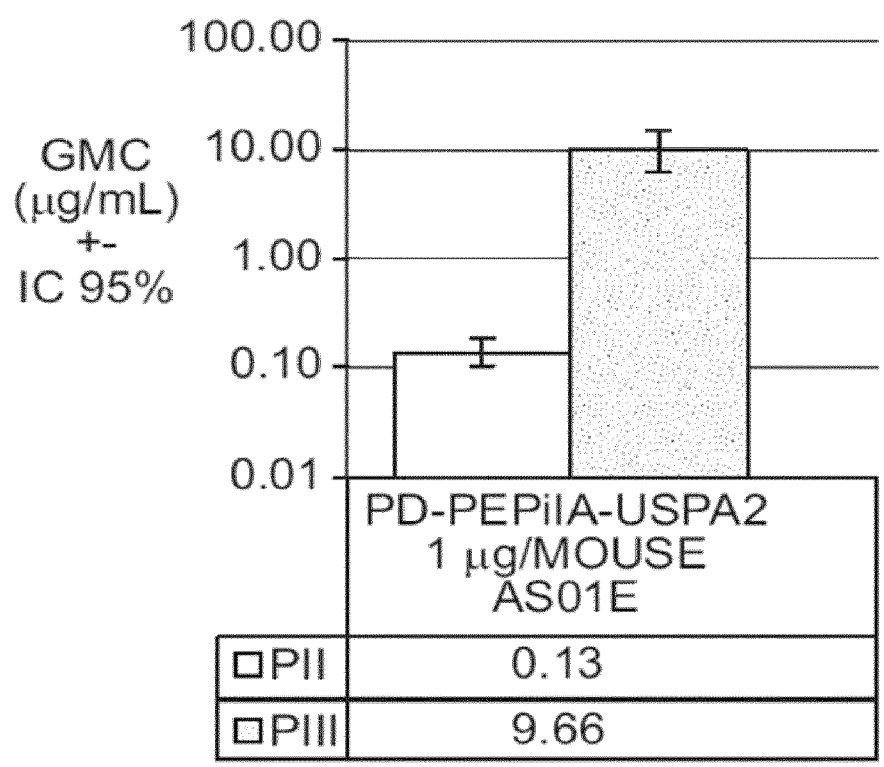
Figure 6C:
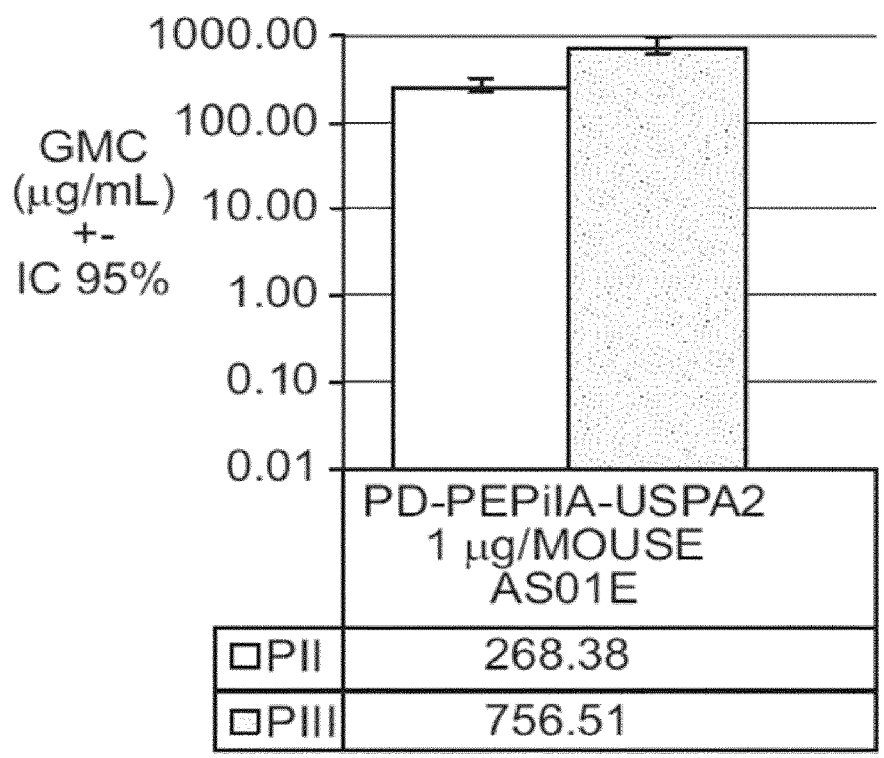
Figure 6D:
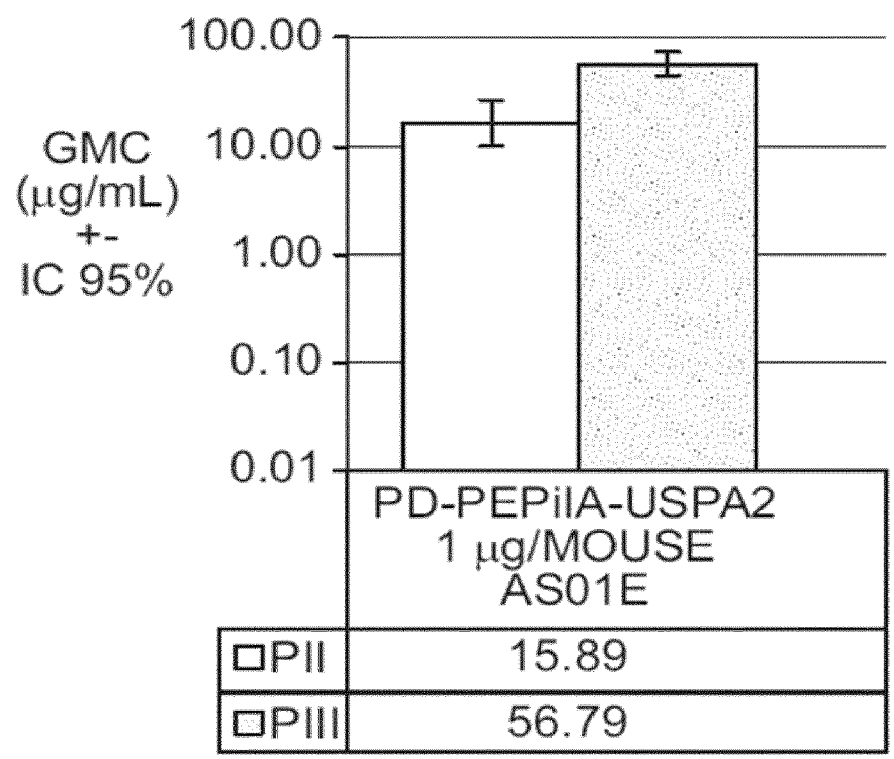
Figure 6E:
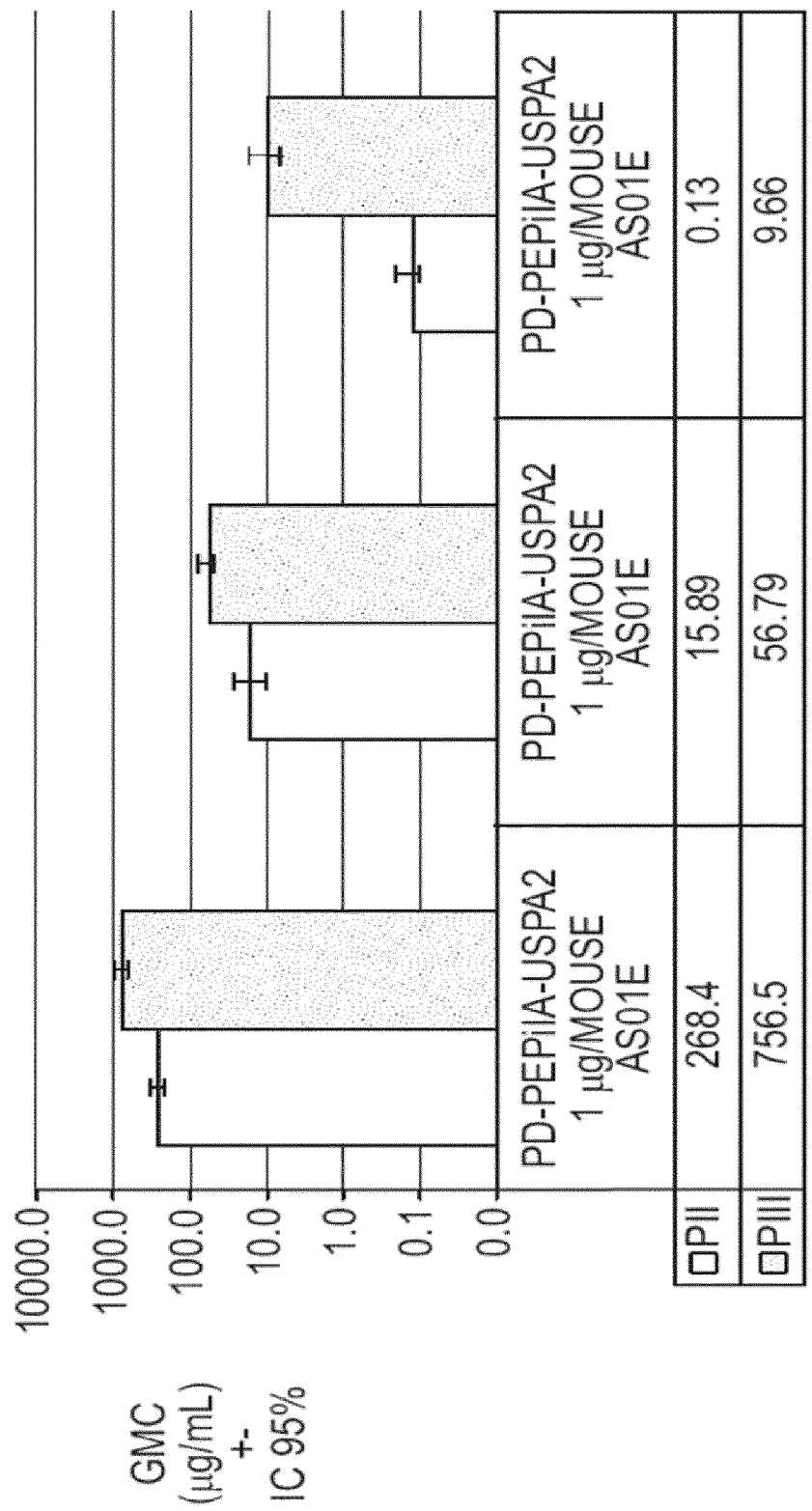

Current and former smokers aged from 50-70 years old were enrolled in a Phase I study (NTHi-003) and received two doses of the NTHi vaccine (10 µg or 30 µg of each antigen) at Day 1 and Day 61 (according to a 0, 2-month schedule). The antibody and cell mediated immune responses (CMI) to PD, PE and PilA induced by the vaccine formulation was evaluated prior to vaccination and at 30 days after each vaccination. Blood samples were taken for immunogenicity testing at 30 days after each vaccination (i.e. Days 0, 30, 60, 90, 180, 210 and 420). The anti-PD, anti-PE and anti-PilA antibody concentrations were measured by ELISA, using standardized procedures. The cut-off of the assays was 100 ELISA units (EU)/mL, 8 EU/mL and 7 EU/mL for anti-PD, anti-PE and anti-PilA, respectively (FIGS. 4A, 4B and 4C). Note: The anti-PD ELISA used in this study had been validated in 2001 (cut-off=100 EU/mL) and did not meet the latest validation standards. Therefore, sera samples were retested with the validated 2014 anti-PD ELISA (cut-off=153 EU/mL). CMI responses (antigen-specific CD4+ and CD8+ T-cells) were measured by flow cytometry using intracellular cytokine staining (ICS) on frozen peripheral blood mononuclear cells (PBMCs), following an adaptation of previously described methods [Moris P, van der Most R, Leroux-Roels I, Clement F, Drame M, Hanon E, et al. H5N1 influenza vaccine formulated with AS03 A induces strong cross-reactive and polyfunctional CD4 T-cell responses. J Clin Immunol 2011; 31:443-54.]. After PBMC stimulation with the relevant antigens, the frequency of CD4+ and/or CD8+ T-cells expressing a selected set of cytokines (IL-2, IL-13, IL-17, IFN-γ, TNF-α and CD40L) or a selected combination of cytokines was evaluated (FIGS. 5A, 5B and 5C).

Example 2: Immunogenicity of UspA2 in Combination with PD and PE-PilA NTHi Antigens in Balb/c Mice Immunization Protocol Groups of 25 female Balb/c mice were immunized by the intramuscular (IM) route at days 0, 14 and 28 with 50 µl of the following formulations: 1 µg of UspA2 construct MC-009, 1 µg of PD, 1 µg PEPilA construct LVL-735 adjuvanted with AS01E (50/50 per ml QS21/MPL).

ELISA to Measure Anti-UspA2 Antibodies

Anti-UspA2, anti-PE, anti-PilA and anti-PD IgG levels were determined in individual sera collected at days 28 and 42 as follows: Plates were coated overnight at 4° C. with 100 µl per well of either (1) UspA2 construct MC-009 at 4 µg/ml in carbonate buffer pH 9.6, (2) 2 µg/ml of PE in carbonate buffer pH 9.6, (3) 4 µg/ml of PilA in carbonate buffer pH 9.6 or (4) 8 µg/ml of PD in carbonate buffer pH 9.6.

The plates were washed three times with 0.09% NaCl, 0.05% polysorbate 20 (TWEEN-20; TWEEN is a trademark of Croda International PLC). After washing, serial two fold dilutions of sera were added to micro-wells in PBS TWEEN-20 0.05%. The plates were placed at room temperature for 30 minutes with shaking. After washing, anti-mouse IgG antibodies (Jackson 115-035-003) conjugated to peroxidase (100 µl per well) were added, and the plates were placed at room temperature for 30 minutes with shaking. Plates were washed as above and a solution of 4 mg of o-Phenylenediamine dihydrochloride (OPDA, Sigma P8787) and 5 µl of $H_2O_2$ in 10 ml of citrate 0.1 M PH (pH) 4.5) was added to each well (100 µl/well) for 15 minutes in darkness. The reaction was stopped by addition of 50 µl of HCl 1N and the absorbance was read at 490 nm (620 nm for the reference filter). The titers were calculated by the 4-parameters method using the SOFTMAX Pro software.

Bactericidal Assay

Figure 7:
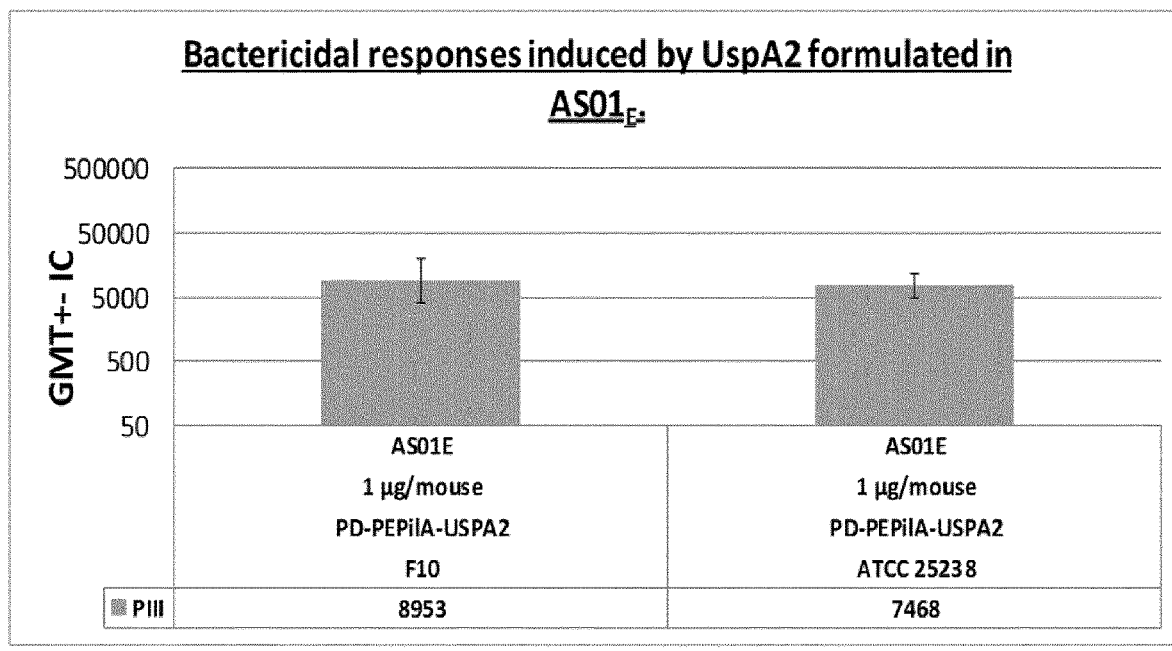
FIG. 7. Bactericidal responses induced by UspA2. The anti-*Moraxella catarrhalis* bactericidal assay was performed against strains expressing a homologous (25238) or a heterologous (F10) UspA2. UspA2 induced high bactericidal titres against both strains.
Figure 8A:
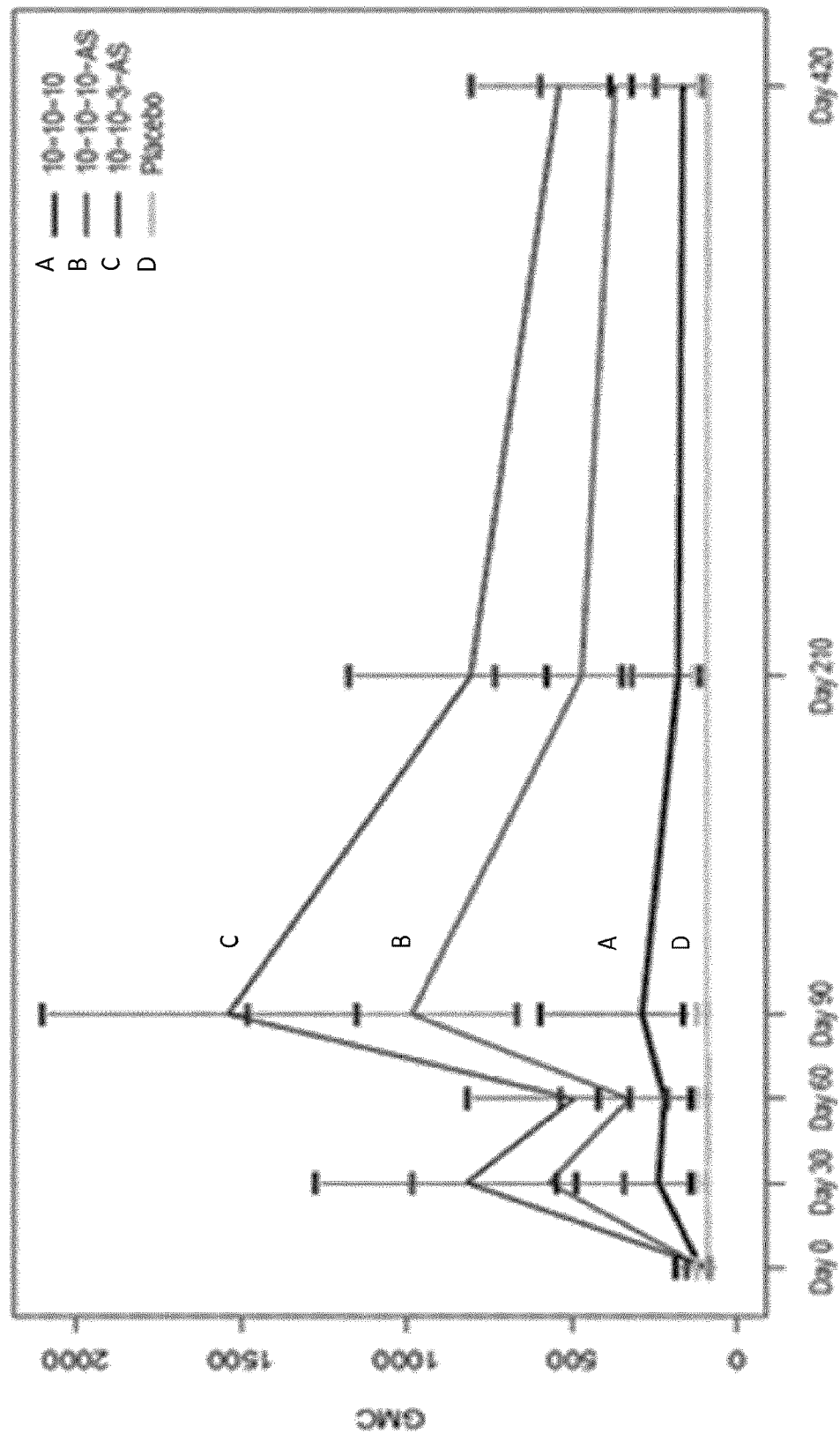
FIG. 8. The IgG responses induced against UspA2, PD, PE and PilA in mice by NTHi-Mcat vaccine (PD-PEPilA-UspA2) are shown in FIG. 8A (PD, protein D), FIG. 8B (PE, protein E), FIG. 8C (PilA) and FIG. 8D (UspA2) respectively in the Phase 1 study in healthy adults aged 18-40 years and in current and former smokers aged 50-70 years (NTHI MCAT-001).
Figure 8B:
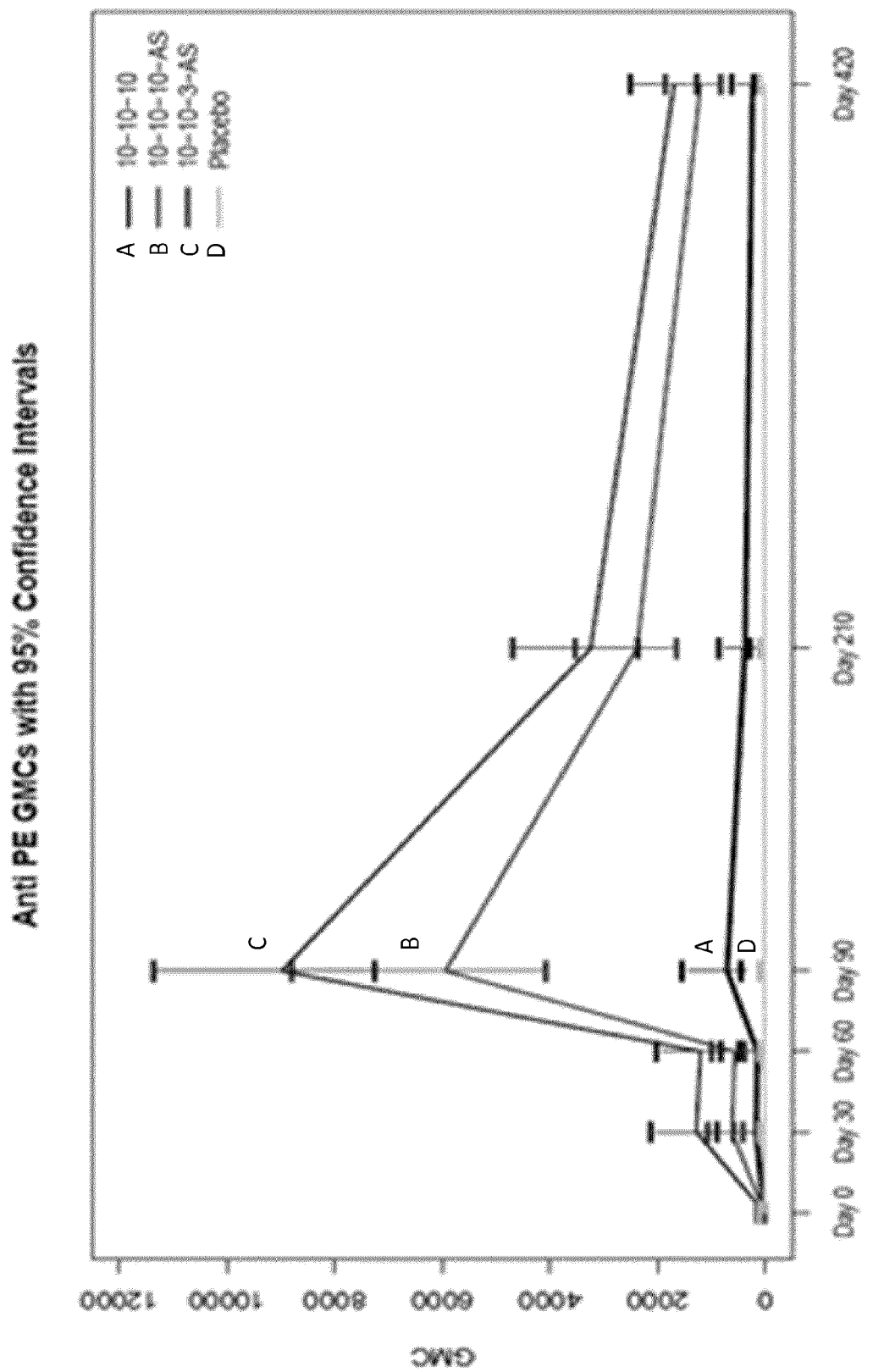
Figure 8C:
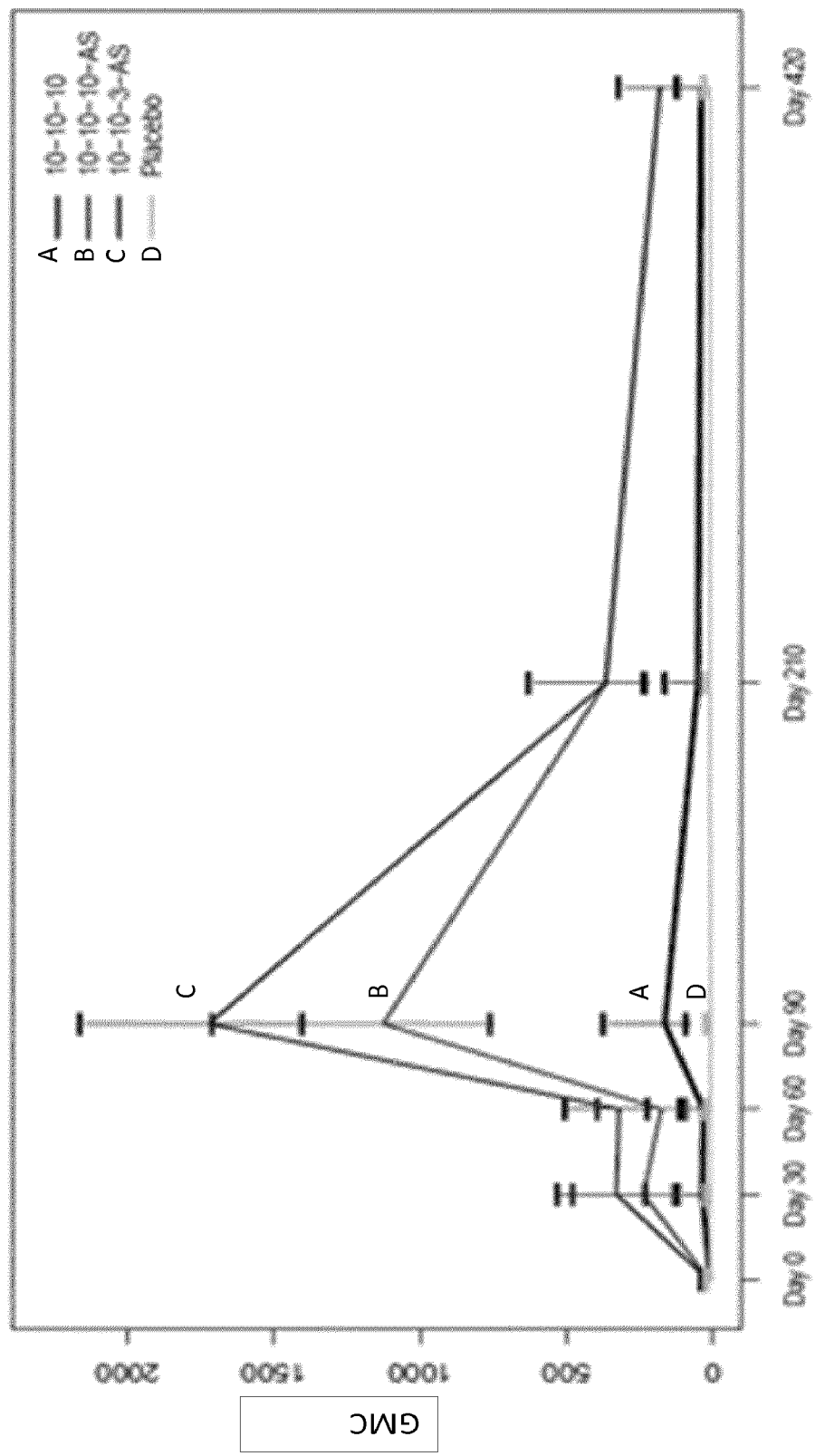
Figure 8D:
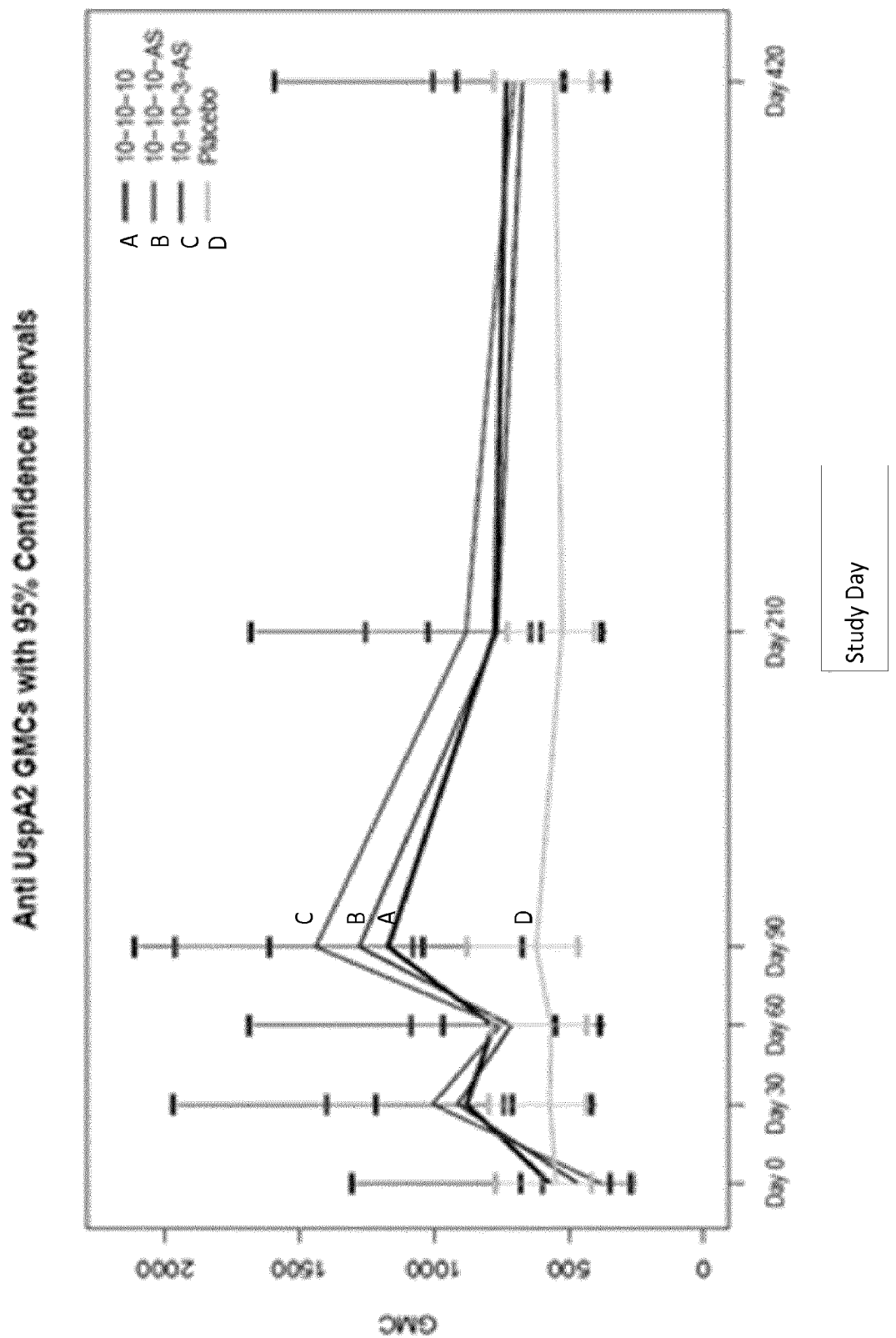

Bactericidal titres were measured in pooled sera (5 pools/group) collected at day 42 using the following protocol: *Moraxella catarrhalis* was cultivated overnight on Petri dish at 37° C.+5% CO2. Bacteria were transferred in 10 ml BHi (broth heart infusion) medium in order to get an OD 620 of 0.650. Serum samples were heated for 45 minutes at 56° C. to inactivate the endogenous complement. Serial two-fold dilutions of sera in SBA buffer (HBSS-BSA 0.1%) were added on a 96-well round bottom microtitre plate (25 µl/well). Subsequently, 50 µl of SBA buffer was added to each well. Then 25 µl of *Moraxella catarrhalis* strain 25238 at 4×10^3 cfu/ml was added to the wells containing sera and incubated for 15 minutes at room temperature. Finally, 25 µl of freshly thawed baby rabbit complement diluted 1/8 in HBSS-BSA 0.1% was added to reach a final volume of 125 µl. Plates were incubated for 1 hour at 37° C. with orbital shaking (210 rpm). The reaction was stopped by laying the microplate on ice for at least 5 minutes. A 20 µl aliquot from each well of the plate was transferred into the corresponding well of a 96-well flat bottom microplate and 50 µl of Mueller Hinton Broth-0.9% agar was added to each well. 50 µl of PBS 0.9% agar was added as a second layer. After 3 hours at 37° C. with 5% $CO_2$, plates were incubated overnight at 25° C. *Moraxella* colonies were counted using an automated image analysis system (KS 400, Zeiss, Oberkochen, Germany). Eight wells without serum sample were used as bacterial controls to determine the number of *Moraxella* per well. The mean number of colony forming units (CFU) of the control wells was determined and used for the calculation of the killing activity for each serum sample. Anti-*Moraxella catarrhalis* bactericidal titres were measured in pooled sera (5 pools/group post-III) collected at day 42. The bactericidal titers were expressed at the reciprocal dilution of serum inducing 50% of killing. The bactericidal assay was performed against *Moraxella catarrhalis* strain ATCC25238™, expressing a homologous UspA2 or a heterologous (F10) UspA2. UspA2 induced high bactericidal titers against both strains as (FIG. 7).

The IgG responses induced against UspA2, PD, PE and PilA in mice by PE-PEPilA-UspA2 vaccine are shown in FIGS. 6A, 6B, 6C, 6D and 6E respectively. No major impact of the addition of UspA2 on PD and PEPilA immunogenicity in AS01E was observed.

Example 3—Phase II Study of Investigational NTHi-Mcat Vaccine

An $AS01_E$-adjuvanted formulation containing 10 µg of PD, 10 µg of the PE-PilA fusion protein and 3.3 µg of UspA2 is evaluated. The antigens and formulation may be prepared and tested as described in WO2015/125118.

Experimental Design

Phase II, observer-blind, randomised, multi-centric study with two parallel groups.

Study Groups

Adults aged 40 to 80 years with a smoking history of at least 10 pack-years, will receive 2 doses of the NTHi-Mcat investigational vaccine, at 0 and 2 months, followed by either a third, booster, dose of the investigational NTHi-Mcat vaccine at 6 or 12 months or placebo control at 6 or 12 months. The study evaluates the safety and reactogenicity profile of the NTHi-Mcat vaccine administered according to two schedules and provides additional data relating to the humoral and cellular immunogenicity of the NTHi-Mcat investigational vaccine.

Schedule 1: Approximately 100 subjects receive three doses of the AS01E-adjuvanted NTHi-Mcat investigational vaccine containing 10 µg of PD, 10 µg of PE-PilA, and 3.3 µg of UspA2 at Day 1, Day 61, Day 181 and one dose of placebo at Day 361.

Schedule 2: Approximately 100 subjects receive three doses of the AS01E-adjuvanted NTHi-Mcat investigational vaccine containing 10 µg of PD, 10 µg of PE-PilA, and 3.3 µg of UspA2 at Day 1, Day 61, Day 361 and one dose of placebo at Day 181.

Subjects are allocated to a study group using a centralised randomisation system on internet (SBIR). The randomisation algorithm uses a minimisation procedure accounting for age (40 59 years or 60 80 years), for smoking status (current or former smokers), for centre and for forced expiratory volume in 1 second (FEV1)/forced vital capacity (FVC) (≥0.7 or <0.7).

TABLE 2

Study vaccines

| Treatment name | Vaccine/product name | Formulation | Presentation | Volume to be administered | Number of doses |
|---|---|---|---|---|---|
| 10-10-3/$AS01_E$ | NTHi-Mcat/10-10-3.3 | PD = 10 µg; PE-PilA = 10 µg; UspA2 = 3.3 µg | Freeze-dried antigens in monodose vial | 0.5 ml | 3 |
|  | AS01E | MPL = 25 µg; QS21 = 25 µg; Liposomes | Liquid in monodose vial |  |  |
| Placebo | Formulation buffer S9b | $Na_2HPO_4$ = 0.4 mg; $KH_2PO_4$ = 56 µg; NaCl = 1.16 mg; KCl = 30 µg; $MgCl_2$ = 15 µg | Liquid in monodose vial | 0.5 ml | 1 |

MPL = 3-O-desacyl-4'-monophosphoryl lipid A; QS-21 = Quillaja saponaria Molina, fraction 21 (Licensed by GSK from Antigenics Inc, a wholly owned subsidiary of Agenus Inc., a Delaware, USA corporation).

TABLE 3

Dosage and administration

| Type of contact and timepoint | Study group | Treatment name | Volume to be administered | Route [1] | Site Location | Directionality[2] | Laterality[3] |
|---|---|---|---|---|---|---|---|
| Visit 1 (Day 1) | Schedule 1 Schedule 2 | 10-10-3/AS01E | 0.5 ml | IM | Deltoid | Upper | Non-dominant |
| Visit 3 (Day 61) | Schedule 1 Schedule 2 | 10-10-3/AS01E | 0.5 ml | IM | Deltoid | Upper | Non-dominant |
| Visit 6 (Day 181) | Schedule 1 Schedule 2 | 10-10-3/AS01E Placebo | 0.5 ml | IM | Deltoid | Upper | Non-dominant |
| Visit 8 (Day 361) | Schedule 1 Schedule 2 | Placebo 10-10-3/AS01E | 0.5 ml | IM | Deltoid | Upper | Non-dominant |

[1] Intramuscular (IM)
[2] Directionality is a qualifier for further detailing the location of the vaccine administration (e.g. Upper, Lower)
[3] The non-dominant arm is the preferred arm of injection. In case it is not possible to administer the vaccine in the non-dominant arm, an injection in the dominant arm may be performed.

Sampling Schedule

Blood samples for assessment of humoral immunogenicity are collected from all subjects at Visit 1 (Day 1), Visit 2 (Day 31), Visit 3 (Day 61), Visit 4 (Day 91), Visit 5 (Day 181), Visit 6 (Day 211), Visit 7 (Day 361), Visit 8 (Day 391) and Visit 9 (Day 451).

Blood samples for assessment of cell-mediated immunogenicity (CMI) are collected from a sub-cohort at Visit 1 (Day 1), Visit 6 (Day 211) and at Visit 8 (Day 391).

Laboratory Assays

Total IgG concentrations are measured by ELISA using qualified procedures.

TABLE 4

Humoral Immunity (Antibody determination)

| System | Component | Method | Unit | Cut-off |
|---|---|---|---|---|
| SERUM | anti-PD antibody | ELISA | EU/ml | 153 |
| | anti-PE antibody | | | 8 |
| | anti-PilA antibody | | | 7 |
| | anti-UspA2 IgG antibody | | | 18 |

EU/ml = ELISA unit per milliliter
Cell-mediated immune assays are performed using qualified procedures including ELISpot and Flow Cytometry.
Note:
assay cut-off may be updated after qualification.

TABLE 5

Cell-mediated Immunity (CMI) using flow cytometry

| System | Component Family | Scale | Method | Unit |
|---|---|---|---|---|
| PBMCs | Specific $CD4^+/CD8^+$ T-cells | Quantitative | Flow cytometry ICS | Number of specific $CD4^+/CD8^+$ T-cells/$10^6$ |

Additional testing on peripheral blood mononuclear cells (PBMCs), such as, but not limited to, evaluation of NTHi and/or Mcat-specific memory B-cells, intracellular cytokine staining (ICS) testing using other bacterial antigens, may be performed.

TABLE 6

Immunological read-outs

| Type of contact and time point | Blood sampling time point Sampling time point | Sub-cohort Name | No. subjects | Component |
|---|---|---|---|---|
| Visit 1 (Day 1) | Pre-Vacc I | All subjects | ~200 | Anti-PD, Anti-PE, Anti-PilA and Anti-UspA2 |
| | | CMI sub-cohort* | ~40 | Specific $CD4^+/CD8^+$ T-cells |
| Visit 2 (Day 31) | Post-Vacc I | All subjects | ~200 | Anti-PD, Anti-PE, Anti-PilA and Anti-UspA2 |
| Visit 3 (Day 61) | Pre-Vacc II | All subjects | ~200 | Anti-PD, Anti-PE, Anti-PilA and Anti-UspA2 |
| Visit 4 (Day 91) | Post-Vacc II | All subjects | ~200 | Anti-PD, Anti-PE, Anti-PilA and Anti-UspA2 |
| Visit 5 (Day 181) | Pre-Vacc III | All subjects | ~120 | Anti-PD, Anti-PE, Anti-PilA and Anti-UspA2 |
| Visit 6 (Day 211) | Post-Vacc III | All subjects | ~120 | Anti-PD, Anti-PE, Anti-PilA and Anti-UspA2 |
| | | CMI sub-cohort* | ~40 | Specific $CD4^+/CD8^+$ T-cells |
| Visit 7 (Day 361) | Pre-Vacc IV | All subjects | ~200 | Anti-PD, Anti-PE, Anti-PilA and Anti-UspA2 |
| Visit 8 (Day 391) | Post-Vacc IV | All subjects | ~200 | Anti-PD, Anti-PE, Anti-PilA and Anti-UspA2 |
| | | CMI sub-cohort* | ~40 | Specific $CD4^+/CD8^+$ T-cells |
| Day 9 (Day 451) | Post-Vacc IV | All subjects | ~200 | Anti-PD, Anti-PE, Anti-PilA and Anti-UspA2 |

*Approximately 20% of the subjects in each group will be part of a sub-cohort for CMI analysis.

Immunogenicity
  Humoral immune response to the components of the NTHi-Mcat investigational vaccine formulations, on Day 1, Day 31, Day 61, Day 91, Day 181, Day 211, Day 361, Day 391 and Day 451 in all subjects, is measured in all groups:
    Anti-PD, anti-PE, anti-PilA and anti-UspA2 antibody concentrations.
  Cell-mediated immune response to components of the NTHi-Mcat investigational vaccine formulations on Day 1, Day 211 and Day 391, in a sub-cohort of subjects, is measured in all groups:
    Frequency of specific CD4+/CD8+ T-cells measured on cryopreserved PBMCs and identified by ICS expressing two or more markers (such as IL-2, IL-13, IL-17, IFN-γ, TNF-α and CD40L).

Example 4—Phase I Study of Investigational NTHi-Mcat Vaccine in Healthy Adults Aged 18-40 Years and in Current and Former Smokers Aged 50-70 Years Three investigational NTHi-Mcat vaccine formulations were evaluated according to a 0, 2 months schedule administered in a staggered design in a Phase 1 study (NTHi-MCAT-001). Firstly (Step 1), healthy adults aged 18-40 years were enrolled and vaccinated with non-adjuvanted (plain) vaccine containing 10 µg of PD, 10 µg of PE-PilA and 10 µg of UspA2 or a placebo control, and secondly (Step 2), current/former smokers aged 50-70 years were vaccinated with either a placebo control, or one of two AS01E-adjuvanted formulations, i.e. 10 µg of PD, 10 µg of PE-PilA and 10 µg of UspA2 (Group 10-10-10-AS) or 10 µg of PD, 10 µg of PE-PilA and 3.3 µg of UspA2 (Group 10-10-3-AS). The placebo used as control was an isotonic saline solution. A total of 76 subjects received at least 1 dose of any NTHi-Mcat formulation and 44 received the placebo.

The vaccine formulations were delivered by intramuscular injection of 0.5 ml volume into the deltoid of the non-dominant arm. If it was not possible to inject in the non-dominant arm, an injection into the dominant arm was performed.

Duration of the study: For each subject, the study lasted approximately 15 months, from screening to study end.

Epoch 001: Primary started at Screening Visit and ended at, and including Visit 6 (Day 90).

Epoch 002: Follow-up started at Visit 7 (Day 210) and ended at Visit 8 (Day 420).

Study Groups:
  (F1 Group) 10-10-10: Subjects received two doses at Day 0 and Day 60 of the non-adjuvanted GSK Biologicals' NTHi-Mcat investigational vaccine containing 10 µg of PD, PE-PilA and UspA2 during Step 1 of the study.
  PLACEBO 1: Subjects received two doses at Day 0 and Day 60 of placebo (saline solution) during Step 1 of the study.
  (F2 Group) 10-10-10-AS: Subjects received two doses at Day 0 and Day 60 of the AS01E-adjuvanted GSK Biologicals' NTHi-Mcat investigational vaccine containing 10 µg of PD, PE-PilA and UspA2 during Step 2 of the study.
  (F3 Group) 10-10-3-AS: Subjects received two doses at Day 0 and Day 60 of the AS01E-adjuvanted GSK Biologicals' NTHi-Mcat investigational vaccine containing 10 µg of PD, 10 µg of PE-PilA, and 3.3 µg of UspA2 during Step 2 of the study.
  PLACEBO 2: Subjects received two doses at Day 0 and Day 60 of placebo (saline solution) during Step 2 of the study.

Sampling Schedule:
  Blood samples for safety (haematology/biochemistry) were collected from all subjects at Screening Visit (pre-Day 0), at Visit 1 (Day 0), Visit 2 (Day 7), Visit 4 (Day 60), Visit 5 (Day 67), Visit 7 (Day 210) and at Visit 8 (Day 420).
  Blood samples for immunogenicity were collected from all subjects for humoral immunity at Visit 1 (Day 0), Visit 3 (Day 30), Visit 4 (Day 60), Visit 6 (Day 90), Visit 7 (Day 210) and at Visit 8 (Day 420), and from a sub-cohort of subjects for cell-mediated immunity (CMI) at Visit 1 (Day 0), Visit 4 (Day 60), Visit 6 (Day 90), Visit 7 (Day 210) and at Visit 8 (Day 420).

Laboratory Assays
Humoral Immunogenicity:
  Humoral immunogenicity was assessed. Serological assays for the quantification of antibodies were performed by ELISA.

TABLE 7

Humoral Immunogenicity

| System | Component | Method | Unit | Cut-off |
|---|---|---|---|---|
| NTHi specific | | | | |
| Serum | Anti-PD | ELISA | EL.U/mL | 153 |
| Serum | Anti-PE | ELISA | EL.U/mL | 25 |
| Serum | Anti-PilA | ELISA | EL.U/mL | 7 (Visit, Day 0; Visit 3, Day 30; Visit 4, Day 60; Visit 6, Day 90) 16 (Visit 7, Day 210; Visit 8, Day 420) |
| NTHi-Mcat specific | | | | |
| Serum | Anti-UspA2 | ELISA | EL.U/mL | 38 |

EL.U/mL = ELISA unit per milliliter
Antibody concentrations are measured by enzyme-linked immunosorbent assay (ELISA) and expressed as geometric mean concentrations (GMCs) in ELISA units per milliliter (EL.U/mL).

TABLE 8

Cell-mediated immunogenicity

| System | Component | Scale | Method | Unit |
|---|---|---|---|---|
| CMI | Specific CD4+/CD8+ T-cells | Quantitative | Flow cytometry | Number of specific CD4+/CD8+ T cells/$10^6$ |

CMI = cell-mediated immunogenicity;

Frequency of specific CD4+ T-cells were measured by flow cytometry intracellular cytokine staining (ICS) expressing two or more markers (such as Interleukin [IL]-2, IL-13, IL-17, Interferon gamma [FN-γ], Tumour necrosis factor alpha [TNF-α] and CD40L). The frequency of specific CD4+ T-cells are summarised [descriptive statistics: Mean and standard deviation (SD)] against each antigen (PD, PE, PilA and UspA2), by group in Step 2 at each time point during which blood samples were collected for CMI.

Frequency of specific CD8+ T-cells were measured by flow cytometry intracellular cytokine staining (ICS) expressing two or more markers (such as IL-2, IL-13, IL-17, IFN-γ, TNF-α and CD40L). The frequency of specific CD8+ T-cells are summarised [descriptive statistics: Mean and standard deviation (SD)] against each antigen (PD, PE, PilA and UspA2), by group in Step 2 at each time point during which blood samples were collected for CMI.

Results

Results are provided in Table 9 and in FIG. 8.

TABLE 9

| | Measured Values | | | |
|---|---|---|---|---|
| | F1 Group | F2 Group | F3 Group | PLACEBO Group |
| Concentration of antibodies against the NTHi-Mcat anti-PD (protein D of *Haemophilus influenzae*) vaccine component | | | | |
| Number of Participants Analyzed | 14 | 31 | 29 | 43 |
| Units: EL.U/mL Geometric Mean (95% Confidence Interval) | | | | |
| Anti-PD antibody, Day 0 | 109.7 (71.2 to 169.1) | 102.8 (77.5 to 136.4) | 88.1 (72.4 to 107.1) | 89 (75 to 105.7) |
| Number of Participants Analyzed | 14 | 30 | 29 | 43 |
| Anti-PD antibody, Day 30 | 239.8 (123 to 467.6) | 569.4 (335.9 to 965.3) | 818 (532 to 1257.8) | 90.8 (76.5 to 107.8) |
| Number of Participants Analyzed | 14 | 31 | 29 | 43 |
| Anti-PD antibody, Day 60 | 220.9 (121.1 to 402.9) | 327.1 (207.4 to 515.6) | 495 (307.2 to 797.5) | 88.6 (75.2 to 104.3) |
| Number of Participants Analyzed | 14 | 30 | 29 | 43 |
| Anti-PD antibody, Day 90 | 289.2 (144.6 to 578.5) | 984.4 (662.3 to 1463.2) | 1538.5 (1134.6 to 2086.2) | 91.8 (77.8 to 108.3) |
| Number of Participants Analyzed | 14 | 31 | 29 | 43 |
| Anti-PD antibody, Day 210 | 179.5 (96.7 to 333.5) | 471.8 (310.2 to 717.5) | 806.1 (560.2 to 1159.9) | 92.9 (79 to 109.2) |
| Number of Participants Analyzed | 14 | 31 | 29 | 43 |
| Anti-PD antibody, Day 420 | 165.1 (89.7 to 303.8) | 370.2 (238.2 to 575.3) | 538.1 (369.1 to 784.5) | 88.8 (77.3 to 102.1) |
| Number of Participants Analyzed | 14 | 31 | 29 | 43 |
| Concentration of antibodies against the NTHi-Mcat anti-PE (protein E of *Haemophilus influenzae*) vaccine component | | | | |
| Number of Participants Analyzed | 14 | 31 | 29 | 43 |
| Units: EL.U/mL Geometric Mean (95% Confidence Interval) | | | | |
| Anti-PE antibody, Day 0 | 31.3 (16.4 to 59.7) | 20.6 (15.7 to 27) | 19.7 (14.8 to 26.2) | 21.9 (17 to 28.1) |
| Number of Participants Analyzed | 14 | 31 | 29 | 43 |
| Anti-PE antibody, Day 30 | 178.3 (64.6 to 491.9) | 627.2 (401 to 980.9) | 1287.8 (816.2 to 2032) | 21.3 (16.7 to 27.1) |
| Number of Participants Analyzed | 13 | 31 | 29 | 43 |
| Anti-PE antibody, Day 60 | 151.9 (58 to 397.6) | 573.1 (360.1 to 912.1) | 1207.1 (753.8 to 1932.9) | 20.3 (15.9 to 25.9) |
| Number of Participants Analyzed | 14 | 31 | 29 | 43 |
| Anti-PE antibody, Day 90 | 719.1 (357.4 to 1446.8) | 5945.2 (4069.5 to 8685.5) | 8983.9 (7150.4 to 11287.5) | 21.8 (17.1 to 27.8) |
| Number of Participants Analyzed | 14 | 31 | 29 | 43 |
| Anti-PE antibody, Day 210 | 385.8 (191.2 to 778.4) | 2390.9 (1655.4 to 3453.1) | 3247.6 (2285.2 to 4615.3) | 20.7 (16.5 to 26) |
| Number of Participants Analyzed | 14 | 31 | 29 | 43 |

TABLE 9-continued

| | Measured Values | | | |
|---|---|---|---|---|
| Anti-PE antibody, Day 420 | 244.1 (112.4 to 529.9) | 1206.6 (817.5 to 1781) | 1701 (1192.1 to 2427.1) | 22.8 (17.5 to 29.7) |
| Number of Participants Analyzed | 14 | 31 | 29 | 43 |

Concentration of antibodies against the NTHi-Mcat anti-PilA (type IV pili subunit of non-typeable *Haemophilus influenzae*) vaccine component

| | | | | |
|---|---|---|---|---|
| Number of Participants Analyzed | 14 | 31 | 29 | 43 |
| Units: EL.U/mL Geometric Mean (95% Confidence Interval) | | | | |
| Anti-PilA antibody, Day 0 | 11.6 (5.3 to 25.2) | 13.5 (8 to 22.6) | 17.1 (11 to 26.5) | 8.8 (6.1 to 12.6) |
| Number of Participants Analyzed | 14 | 31 | 29 | 43 |
| Anti-PilA antibody, Day 30 | 37.2 (13.6 to 101.5) | 238.6 (123.1 to 462.5) | 330.9 (211.7 to 517.2) | 9.2 (6.4 to 13.3) |
| Number of Participants Analyzed | 14 | 29 | 29 | 42 |
| Anti-PilA antibody, Day 60 | 33.2 (11.3 to 97.9) | 177 (83.4 to 375.7) | 321.2 (210.1 to 491.2) | 9 (6.3 to 13) |
| Number of Participants Analyzed | 14 | 30 | 29 | 43 |
| Anti-PilA antibody, Day 90 | 165.8 (76.7 to 358.4) | 1127.5 (751 to 1692.8) | 1722.3 (1383.4 to 2144.2) | 8.6 (5.8 to 12.6) |
| Number of Participants Analyzed | 14 | 31 | 29 | 39 |
| Anti-PilA antibody, Day 210 | 52 (18.4 to 146.8) | 367.2 (220.2 to 612.3) | 671 (508.6 to 885.2) | 11.5 (9 to 14.8) |
| Number of Participants Analyzed | 14 | 31 | 29 | 43 |
| Anti-PilA antibody, Day 420 | 40.8 (16.5 to 100.7) | 181.8 (108 to 305.9) | 322.2 (233.4 to 444.9) | 11.9 (9.2 to 15.5) |
| Number of Participants Analyzed | 14 | 31 | 29 | 43 |

Concentration of antibodies against the NTHi-Mcat anti-UspA2 (ubiquitous surface protein A2 of *Moraxella catarrhalis*) vaccine component

| | | | | |
|---|---|---|---|---|
| Number of Participants Analyzed | 14 | 31 | 29 | 43 |
| Units: EL.U/mL Geometric Mean (95% Confidence Interval) | | | | |
| Anti-UspA2 IgG antibody, Day 0 | 572.5 (254.4 to 1288.6) | 384.1 (253 to 583.2) | 468.1 (330.6 to 662.8) | 548.3 (399.4 to 752.8) |
| Number of Participants Analyzed | 14 | 31 | 29 | 43 |
| Anti-UspA2 IgG antibody, Day 30 | 879.9 (396.6 to 1952.4) | 1006.7 (732.5 to 1383.6) | 913.5 (693.3 to 1203.7) | 571.5 (416.9 to 783.4) |
| Number of Participants Analyzed | 14 | 31 | 29 | 43 |
| Anti-UspA2 IgG antibody, Day 60 | 780.7 (365.4 to 1668.3) | 754.4 (533.1 to 1067.6) | 714.7 (538.9 to 947.8) | 567 (418 to 769.1) |
| Number of Participants Analyzed | 14 | 31 | 29 | 43 |
| Anti-UspA2 IgG antibody, Day 90 | 1172 (654.7 to 2097.9) | 1440.7 (1065.8 to 1947.5) | 1279 (1026.1 to 1594.4) | 621.5 (449.1 to 860) |
| Number of Participants Analyzed | 14 | 31 | 29 | 43 |
| Anti-UspA2 IgG antibody, Day 210 | 775.1 (361.3 to 1662.8) | 882.5 (629.8 to 1236.7) | 767.2 (584.8 to 1006.5) | 525.7 (386.8 to 714.5) |
| Number of Participants Analyzed | 14 | 31 | 29 | 43 |

TABLE 9-continued

| Measured Values | | | | |
|---|---|---|---|---|
| Anti-UspA2 IgG antibody, Day 420 | 732 (339.2 to 1579.5) | 703.6 (501.8 to 986.5) | 673.4 (504.3 to 899.2) | 552.9 (399.7 to 764.9) |
| Number of Participants Analyzed | 14 | 31 | 29 | 43 |

| | F2 Group | F3 Group | PLACEBO Group |
|---|---|---|---|
| Frequency of specific Cluster of differentiation (CD)4+ T-cells against NTHi-Mcat antigens collected for the evaluation of cell-mediated immune response | | | |
| Number of Participants Analyzed | 16 | 12 | 15 |
| Units: CD4+ T-cells/million cells Mean ± Standard Deviation | | | |
| CD4+.PD, Day 0 | 28.3 ± 42.1 | 81.8 ± 92.29 | 37.4 ± 46.29 |
| Number of Participants Analyzed | 12 | 12 | 13 |
| CD4+.PD, Day 60 | 105.4 ± 123.95 | 107.8 ± 117.92 | 55 ± 91.94 |
| Number of Participants Analyzed | 16 | 12 | 15 |
| CD4+.PD, Day 90 | 283.3 ± 236.93 | 349.9 ± 216.5 | 90.5 ± 117.41 |
| Number of Participants Analyzed | 16 | 11 | 13 |
| CD4+.PD, Day 210 | 120.4 ± 99.23 | 176.9 ± 101.39 | 78.7 ± 112.16 |
| Number of Participants Analyzed | 11 | 11 | 13 |
| CD4+.PD, Day 420 | 154.3 ± 165.98 | 164.8 ± 123.33 | 60.3 ± 82.01 |
| Number of Participants Analyzed | 13 | 9 | 14 |
| CD4+.PE, Day 0 | 89.2 ± 199.87 | 41.4 ± 48.55 | 47.1 ± 70.65 |
| Number of Participants Analyzed | 12 | 12 | 13 |
| CD4+.PE, Day 60 | 370.7 ± 372.5 | 176.9 ± 172.74 | 50.9 ± 47.91 |
| Number of Participants Analyzed | 16 | 12 | 15 |
| CD4+.PE, Day 90 | 1182.2 ± 1507.29 | 732.7 ± 804.67 | 52.4 ± 56.2 |
| Number of Participants Analyzed | 16 | 11 | 13 |
| CD4+.PE, Day 210 | 469.1 ± 381.87 | 337.4 ± 228.12 | 39.1 ± 65.14 |
| Number of Participants Analyzed | 12 | 11 | 14 |
| CD4+.PE, Day 420 | 545 ± 735.89 | 215.8 ± 137.79 | 26.6 ± 51.74 |
| Number of Participants Analyzed | 14 | 10 | 14 |
| CD4+.PilA, Day 0 | 32.8 ± 43.6 | 60.5 ± 92.87 | 32.6 ± 48.69 |
| Number of Participants Analyzed | 12 | 12 | 13 |
| CD4+.PilA, Day 60 | 169.1 ± 150.22 | 110.2 ± 67.81 | 57.1 ± 99.26 |
| Number of Participants Analyzed | 16 | 11 | 15 |
| CD4+.PilA, Day 90 | 508.6 ± 474.31 | 330.5 ± 412.4 | 99 ± 152.45 |
| Number of Participants Analyzed | 16 | 11 | 13 |
| CD4+.PilA, Day 210 | 326 ± 208.31 | 220.8 ± 148.59 | 43.7 ± 69.03 |
| Number of Participants Analyzed | 7 | 9 | 11 |
| CD4+.PilA, Day 420 | 348.8 ± 376.87 | 131.1 ± 75.89 | 59.1 ± 53.4 |
| Number of Participants Analyzed | 10 | 8 | 12 |
| CD4+.UspA2, Day 0 | 115.4 ± 154.96 | 126.3 ± 97.92 | 131.1 ± 182.97 |
| Number of Participants Analyzed | 11 | 12 | 13 |
| CD4+.UspA2, Day 60 | 383.9 ± 326.2 | 253 ± 202.76 | 278.7 ± 672.84 |
| Number of Participants Analyzed | 16 | 12 | 15 |
| CD4+.UspA2, Day 90 | 1392.6 ± 1145.48 | 979.2 ± 807.03 | 143.5 ± 237.29 |
| Number of Participants Analyzed | 16 | 11 | 13 |
| CD4+.UspA2, Day 210 | 582.9 ± 376.54 | 322.8 ± 273.5 | 143.9 ± 242.72 |
| Number of Participants Analyzed | 13 | 11 | 15 |
| CD4+.UspA2, Day 420 | 723.2 ± 763.51 | 385.4 ± 174.08 | 126.6 ± 187.52 |
| Number of Participants Analyzed | 14 | 10 | 14 |

TABLE 9-continued

| Measured Values | | | |
|---|---|---|---|
| Frequency of specific CD8+ T-cells against NTHi-Mcat antigens collected for the evaluation of cell-mediated immune response | | | |
| Number of Participants Analyzed | 15 | 12 | 13 |
| Units: CD8+ T-cells/million cells | | | |
| Mean ± Standard Deviation | | | |
| CD8+.PD, Day 0 | 66 ± 88.69 | 27.9 ± 80.68 | 46.9 ± 73.28 |
| Number of Participants Analyzed | 11 | 12 | 13 |
| CD8+.PD, Day 60 | 29.4 ± 49.67 | 1 ± 0 | 20.5 ± 55.1 |
| Number of Participants Analyzed | 15 | 11 | 12 |
| CD8+.PD, Day 90 | 66.5 ± 97.16 | 7.7 ± 21.19 | 49 ± 64.89 |
| Number of Participants Analyzed | 14 | 10 | 12 |
| CD8+.PD, Day 210 | 66.4 ± 101.79 | 16.8 ± 42.84 | 17.7 ± 33.01 |
| Number of Participants Analyzed | 11 | 12 | 11 |
| CD8+.PD, Day 420 | 43.2 ± 51.32 | 10.6 ± 17.98 | 37.3 ± 70.58 |
| Number of Participants Analyzed | 13 | 8 | 12 |
| CD8+.PE, Day 0 | 42.4 ± 52.5 | 33.3 ± 59.32 | 74.4 ± 175.42 |
| Number of Participants Analyzed | 11 | 12 | 12 |
| CD8+.PE, Day 60 | 27.8 ± 46.77 | 26.1 ± 40.81 | 42.7 ± 107.03 |
| Number of Participants Analyzed | 15 | 11 | 12 |
| CD8+.PE, Day 90 | 30.4 ± 52.48 | 19.8 ± 43.69 | 45.4 ± 82.76 |
| Number of Participants Analyzed | 14 | 10 | 12 |
| CD8+.PE, Day 210 | 31.8 ± 52.08 | 30.6 ± 62.25 | 44.2 ± 85.37 |
| Number of Participants Analyzed | 12 | 12 | 12 |
| CD8+.PE, Day 420 | 5.7 ± 10.89 | 27 ± 58.46 | 19.4 ± 44.74 |
| Number of Participants Analyzed | 15 | 10 | 12 |
| CD8+.PilA, Day 0 | 34.6 ± 57.02 | 16 ± 40.27 | 44.7 ± 58.58 |
| Number of Participants Analyzed | 11 | 12 | 13 |
| CD8+.PilA, Day 60 | 26 ± 82.07 | 35.1 ± 39.81 | 28.7 ± 72.65 |
| Number of Participants Analyzed | 15 | 11 | 12 |
| CD8+.PilA, Day 90 | 50.8 ± 82.01 | 27.9 ± 43.03 | 28.3 ± 45.69 |
| Number of Participants Analyzed | 14 | 10 | 11 |
| CD8+.PilA, Day 210 | 11.3 ± 19.17 | 30.9 ± 70.04 | 21.4 ± 35.86 |
| Number of Participants Analyzed | 8 | 9 | 9 |
| CD8+.PilA, Day 420 | 28 ± 50.45 | 23 ± 37.7 | 28 ± 39.21 |
| Number of Participants Analyzed | 10 | 7 | 10 |
| CD8+.UspA2, Day 0 | 22.5 ± 35.07 | 34.9 ± 50.24 | 85.3 ± 140.42 |
| Number of Participants Analyzed | 10 | 12 | 13 |
| CD8+.UspA2, Day 60 | 29.3 ± 67.7 | 27.7 ± 50.12 | 21 ± 36.81 |
| Number of Participants Analyzed | 15 | 11 | 12 |
| CD8+.UspA2, Day 90 | 74.1 ± 99.92 | 20.6 ± 26.17 | 37.4 ± 76.73 |
| Number of Participants Analyzed | 14 | 10 | 11 |
| CD8+.UspA2, Day 210 | 61.5 ± 89.07 | 17.3 ± 26.54 | 48.1 ± 53.97 |
| Number of Participants Analyzed | 13 | 11 | 13 |
| CD8+.UspA2, Day 420 | 16.7 ± 24.45 | 25.3 ± 70.42 | 48.8 ± 86.71 |
| Number of Participants Analyzed | 15 | 10 | 12 |

REFERENCES

1. Global Initiative for Chronic Obstructive Lung Disease (GOLD). From the Global Strategy for the diagnosis, management, and prevention of Chronic Obstructive Pulmonary Disease, updated 2017; http://www.goldcopd.org/. Last accessed: 16 Mar. 2017.

2. Buist S, McBurnie M A, Vollmer W M, et al. International variation in the prevalence of COPD (The BOLD Study): a population-based prevalence study. *Lancet* 2007; 370: 741-50.

3. Mannino D M, Homa D M, Akinbami L J, et al. Chronic obstructive pulmonary disease surveillance-United States, 1971-2000. *MMWR Surveill Summ* 2002; 51:1-16.

4. Global, regional, and national life expectancy, all-cause mortality, and cause-specific mortality for 249 causes of death, 1980-2015: a systematic analysis for the Global Burden of Disease Study 2015. Lancet 2016; 388: 1459-544.
5. Sapey E, Stockley R A. COPD exacerbations 2: aetiology. *Thorax* 2006; 61:250-8.
6. Erb-Downward J R, Thompson D L, Han M K, et al. Analysis of the lung microbiome in the "healthy" smoker and in COPD. *PLoS One* 2011; 6:e16384.
7. Wilkinson™, Hurst J R, Perera W R, et al. Effect of interactions between lower airway bacterial and rhinoviral infection in exacerbations of COPD. *Chest* 2006; 129:317-24.
8. Sethi S, Evans N, Grant B J, et al. New strains of bacteria and exacerbations of chronic obstructive pulmonary disease. *N Engl J Med* 2002; 347:465-71.
9. Alamoudi O S. Bacterial infection and risk factors in outpatients with acute exacerbation of chronic obstructive pulmonary disease: a 2-year prospective study. *Respirology* 2007; 12:283-7.
10. Bandi V, Jakubowycz M, Kinyon C, et al. Infectious exacerbations of chronic obstructive pulmonary disease associated with respiratory viruses and non-typeable *Haemophilus influenzae*. *FEMS Immunol Med Microbiol.* 2003; 37:69-75.
11. Beasley V, Joshi P V, Singanayagam A, et al. Lung microbiology and exacerbations in COPD. *Int J Chron Obstruct Pulmon Dis.* 2012; 7:555-69.
12. Hutchinson A F, Ghimire A K, Thompson M A, et al. A community-based, time-matched, case-control study of respiratory viruses and exacerbations of COPD. *Respir Med* 2007; 101:2472-81.
13. Ko F W, Ip M, Chan P K, et al. A 1-year prospective study of the infectious etiology in patients hospitalized with acute exacerbations of COPD. *Chest* 2007; 131:44-52.
14. Larsen M V, Janner J H, Nielsen S D, et al. Bacteriology in acute exacerbation of chronic obstructive pulmonary disease in patients admitted to hospital. *Scand J Infect Dis* 2009; 41:26-32.
15. Murphy T F, Brauer A L, Grant B J, et al. *Moraxella catarrhalis* in chronic obstructive pulmonary disease: burden of disease and immune response. *Am J Respir Crit Care Med* 2005; 172:195-9.
16. Papi A, Bellettato C M, Braccioni F, et al. Infections and airway inflammation in chronic obstructive pulmonary disease severe exacerbations. *Am J Respir Crit Care Med* 2006; 173:1114-21.
17. Rosell A, Monsó E, Soler N, et al. Microbiologic determinants of exacerbation in chronic obstructive pulmonary disease. *Arch Intern Med* 2005; 165: 891-7.
18. Sethi S, Murphy T F. Infection in the pathogenesis and course of chronic obstructive pulmonary disease. *N Engl J Med* 2008; 359:2355-65.
18A. Wilkinson T M A, Aris E, Bourne S, et al A prospective, observational cohort study of the seasonal dynamics of airway pathogens in the aetiology of exacerbations in COPD Thorax Published Online First: 21 Apr. 2017. doi: 10.1136/thoraxjnl-2016-209023
19. Prymula et al Lancet 367; 740-748 (2006).
20. J. Immunology 183: 2593-2601 (2009).
21. The Journal of Infectious Diseases 199:522-531 (2009).
22. Microbes and Infection 10:87-96 (2008).
23. The Journal of Infectious Diseases 201:414-419 (2010).
24. Immunology 183: 2593-2601 (2009).
25. Infection and Immunity, 73: 1635-1643 (2005).
26. Molecular Microbiology 65: 1288-1299 (2007).
27. Hoiczyk et al. EMBO J. 19: 5989-5999 (2000).
28. Aebi et al., Infection & Immunity 65(11) 4367-4377 (1997).
29. Helminnen et al. J Infect Dis. 170(4): 867-72 (1994).
30. Tan et al., J Infect Dis. 192(6): 1029-38 (2005).
31. Tan et al., J Infect Dis. 194(4): 493-7 (2006).
32. Attia A S et al. Infect Immun 73(4): 2400-2410 (2005).
33. de Vries et al., Microbiol Mol Biol Rev. 73(3): 389-406 (2009)).

---

The invention claimed is:

1. A method of boosting a pre-existing immune response against non-typeable *Haemophilus influenzae* and *Moraxella catarrhalis* in a subject, the method comprising the step of administering an immunogenic composition comprising
   (i) protein D from *Haemophilus influenzae* (PD) or a fragment thereof having at least 85% identity to SEQ ID NO: 1,
   (ii) Protein E from *Haemophilus influenzae* (PE) or a fragment thereof having at least 85% identity to SEQ ID NO: 59,
   (iii) pilin A from *Haemophilus* influenza (PilA) or a fragment thereof having at least 85% identity to SEQ ID NO: 60,
   (iv) Ubiquitous surface protein A2 from *Moraxella catarrhalis* (UspA2) or a fragment thereof having at least 450, 490, 511, 534 or 535 contiguous amino acids of SEQ ID NO: 13, and
   (v) adjuvant 3-O-desacyl-4'-monophosphoryl lipid A (MPL), and a saponin QS 21 to the subject in an amount sufficient to elicit a further or additional, immune response relative to the pre-existing immune response, wherein the pre-existing immune response has been elicited by prior administration of at least two doses of the immunogenic composition and wherein the immunogenic composition is administered at least 6 months after administration of the first of the at least two doses of the immunogenic composition comprising
   (i) protein D from *Haemophilus influenzae* (PD) or a fragment thereof having 85% identity to SEQ ID NO: 1,
   (ii) Protein E from *Haemophilus influenzae* (PE) or a fragment thereof having 85% identity to SEQ ID NO: 59,
   (iii) pilin A from *Haemophilus influenzae* (PilA) or a fragment thereof having 85% identity to SEQ ID NO: 60,
   (iv) Ubiquitous surface protein A2 from *Moraxella catarrhalis* (UspA2) or a fragment thereof having at least 450, 490, 511, 534 or 535 contiguous amino acids of SEQ ID NO: 13, and (vi) adjuvant 3-O-desacyl-4'-monophosphoryl lipid A (MPL), and a saponin QS 21.

2. The method according to claim 1, wherein the subject has a previous history of Chronic Obstructive Pulmonary Disease (COPD).

3. The method according to claim 2, wherein the subject has a previous history of moderate and severe Acute Exacerbation of Chronic Obstructive Pulmonary Disease (AECOPD).

4. The method according to claim 2 wherein the immunogenic composition is administered six to 13 months (e.g. administered between six and 12 months; administered at six months; or administered at 12 months) after administration of the first of the at least two doses of vaccine.

5. The method according to claim 4 wherein the immunogenic composition is subsequently administered every 12 months on the anniversary of administration of the first of the at least two doses of vaccine.

6. The method according to claim 2, wherein the immune response is against PD, PE, PilA and UspA2 and is sufficient to reduce the frequency of Acute Exacerbation of Chronic Obstructive Pulmonary Disease (AECOPD).

7. The method according to claim 6, wherein the subject is a human.

8. The method according to claim 6, wherein the subject is an adult human aged between 18 and 40 or between 50 and 70 or between 40 and 80 years of age.

9. The method according to claim 1 wherein the UspA2 is at least 63%, 66%, 70%, 72%, 74%, 75%, 77%, 80%, 84%, 85%, 90%, 95%, 96%, 97%, 98%, 99% or 100% identical, over the entire length, to SEQ ID NO: 13.

10. The method according to claim 1 wherein the UspA2 consists essentially of an immunogenic fragment of UspA2 selected from the group consisting of amino acids 30-540 of SEQ ID NO. 13 (SEQ ID NO: 61, 62, 63 or 64), amino acids 31-540 of SEQ ID NO: 13 (SEQ ID NO: 71), amino acids 30-519 of SEQ ID NO: 13 (SEQ ID NO: 65 or 66), amino acids 30-564 of SEQ ID NO: 13 (SEQ ID NO: 67 or 68) and amino acids 31-564 of SEQ ID NO: 13 (SEQ ID NO: 69 or 70).

11. The method according to claim 2 wherein PE and PilA are present as a fusion protein, particularly SEQ ID NO:72 or SEQ ID NO:73.

12. The method according to claim 2 wherein the immunogenic composition comprises UspA2 (SEQ ID NO: 69), Protein D (SEQ ID NO:1) and a PE-PilA fusion protein (SEQ ID NO: 72).

13. The method according to claim 1 wherein the immunogenic composition comprises (1) 10 μg of PD, (2) 10 pg of a PE-PilA fusion protein, (3) 3.3 pg of UspA2 and (4) adjuvant ASO1E comprising 25 ug MPL and 25 ug of QS21.

* * * * *

UNITED STATES PATENT AND TRADEMARK OFFICE
CERTIFICATE OF CORRECTION

| | | |
|---|---|---|
| PATENT NO. | : 11,723,966 B2 | Page 1 of 1 |
| APPLICATION NO. | : 16/638595 | |
| DATED | : August 15, 2023 | |
| INVENTOR(S) | : Arora et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this
Twelfth Day of November, 2024

*Katherine Kelly Vidal*

Katherine Kelly Vidal
*Director of the United States Patent and Trademark Office*